US012766156B2

(12) United States Patent
Stamets

(10) Patent No.: US 12,766,156 B2
(45) **Date of Patent: *Oct. 20, 2026**

(54) TRYPTAMINE COMPOSITIONS FOR ENHANCING NEURITE OUTGROWTH

(71) Applicant: TURTLE BEAR HOLDINGS, LLC, Shelton, WA (US)

(72) Inventor: Paul Edward Stamets, Shelton, WA (US)

(73) Assignee: TURTLE BEAR HOLDINGS, LLC, Shelton, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/048,753

(22) Filed: Feb. 7, 2025

(65) Prior Publication Data

US 2026/0108544 A1 Apr. 23, 2026

Related U.S. Application Data

(63) Continuation of application No. 18/475,724, filed on Sep. 27, 2023, now Pat. No. 12,257,258, which is a continuation of application No. 17/570,054, filed on Jan. 6, 2022, now Pat. No. 11,911,401, which is a continuation of application No. 16/951,009, filed on Nov. 18, 2020, now Pat. No. 11,660,305.

(60) Provisional application No. 63/007,482, filed on Apr. 9, 2020, provisional application No. 62/937,536, filed on Nov. 19, 2019.

(51) Int. Cl.

| | |
|---|---|
| ***A61K 31/661*** | (2006.01) |
| ***A61K 9/08*** | (2006.01) |
| ***A61K 31/00*** | (2006.01) |
| ***A61K 31/05*** | (2006.01) |
| ***A61K 31/352*** | (2006.01) |
| ***A61K 31/4045*** | (2006.01) |
| ***A61K 31/455*** | (2006.01) |
| ***A61K 36/06*** | (2006.01) |
| ***A61K 36/066*** | (2006.01) |
| ***A61K 36/07*** | (2006.01) |
| ***A61K 36/185*** | (2006.01) |
| ***A61K 36/73*** | (2006.01) |
| ***A61P 25/24*** | (2006.01) |

(52) U.S. Cl.

CPC .............. *A61K 31/661* (2013.01); *A61K 9/08* (2013.01); *A61K 31/05* (2013.01); *A61K 31/352* (2013.01); *A61K 31/4045* (2013.01); *A61K 31/455* (2013.01); *A61K 31/658* (2023.05); *A61K 36/06* (2013.01); *A61K 36/066* (2013.01); *A61K 36/07* (2013.01); *A61K 36/3482* (2024.05); *A61K 36/73* (2013.01); *A61P 25/24* (2018.01)

(58) Field of Classification Search

CPC .................................................... A61K 31/661

See application file for complete search history.

(56) References Cited

U.S. PATENT DOCUMENTS

| | | | |
|---|---|---|---|
| 3,075,992 | A | 1/1963 | Hofmann et al. |
| 3,078,214 | A | 2/1963 | Hofmann et al. |
| 3,192,111 | A | 6/1965 | Hofmann et al. |
| 11,660,305 | B2 | 5/2023 | Stamets |
| 2001/0008641 | A1 | 7/2001 | Krotzer |
| 2005/0276815 | A1 | 12/2005 | Stamets |
| 2008/0194553 | A1 | 8/2008 | Gillessen |
| 2010/0028469 | A1 | 2/2010 | Alberte et al. |
| 2011/0038958 | A1 | 2/2011 | Kikuchi et al. |
| 2011/0206721 | A1 | 8/2011 | Nair |
| 2013/0156872 | A1 | 6/2013 | Giuliano et al. |
| 2014/0220150 | A1 | 8/2014 | Stamets |
| 2015/0209306 | A1 | 7/2015 | Bredesen et al. |
| 2015/0335689 | A1 | 11/2015 | Stamets |
| 2016/0000754 | A1 | 1/2016 | Stamets |
| 2016/0206670 | A1 | 7/2016 | Wieser et al. |
| 2017/0035820 | A1 | 2/2017 | Stamets |
| 2018/0021326 | A1 | 1/2018 | Stamets |

(Continued)

FOREIGN PATENT DOCUMENTS

| | | | |
|---|---|---|---|
| CA | 3151154 | A1 | 3/2021 |
| WO | 2005039546 | A2 | 5/2005 |

(Continued)

OTHER PUBLICATIONS

Feldman, Understanding 'Evergreening' : Making Minor Modifications Of Existing Medications To Extend Protections, Health Affairs Jun. 2022 41:6, 801-804.*

(Continued)

*Primary Examiner* — Nizal S Chandrakumar

(74) *Attorney, Agent, or Firm* — Michael Best & Friedrich LLP

(57) ABSTRACT

Described herein are neurotrophic and nootropic compositions and methods for treating subjects with such compositions. In one aspect the composition comprises one or more tryptamines or in pure form or extracts from psilocybin containing mushrooms, or combinations thereof optionally combined with one or more phenethylamines or amphetamines in pure form or extracts from a plant or mushroom, or combinations thereof, optionally one or more erinacines or hericenones in pure form, extracts from Hericium mushroom species (e.g., H. *erinaceus, H. coralloides, H. ramosum*) or combinations thereof, optionally one or more cannabinoids in pure form or extracts from *Cannabis sativa, Cannabis sativa, Cannabis indica*, or *Cannabis ruderalis*, optionally, one or more adversive compounds, and optionally one or more pharmaceutically acceptable excipients.

20 Claims, 19 Drawing Sheets

(56) References Cited

U.S. PATENT DOCUMENTS

| | | | |
|---|---|---|---|
| 2018/0021405 | A1 | 1/2018 | Hausman |
| 2018/0200224 | A1 | 7/2018 | Stamets |
| 2018/0221396 | A1 | 8/2018 | Chadeayne |
| 2018/0311499 | A1 | 11/2018 | Yun et al. |
| 2019/0105313 | A1 | 4/2019 | Stamets |
| 2019/0142851 | A1 | 5/2019 | Chadeayne |
| 2019/0192498 | A1 | 6/2019 | Stamets |
| 2019/0240293 | A1 | 8/2019 | Weinstein |
| 2021/0069170 | A1 | 3/2021 | Stamets |
| 2021/0251976 | A1 | 8/2021 | Stamets |
| 2021/0308201 | A1 | 10/2021 | Stamets |
| 2022/0304980 | A1 | 9/2022 | Arnold et al. |
| 2023/0026731 | A1 | 1/2023 | Kochinke |

FOREIGN PATENT DOCUMENTS

| | | | |
|---|---|---|---|
| WO | 2006091988 | A1 | 8/2006 |
| WO | 2008062983 | A1 | 5/2008 |
| WO | 2014205250 | A1 | 6/2014 |
| WO | 2016001922 | A1 | 1/2016 |
| WO | 2016009021 | A1 | 1/2016 |
| WO | 2018135943 | A1 | 7/2018 |
| WO | 2020181194 | A1 | 9/2020 |
| WO | 2021041407 | A1 | 3/2021 |
| WO | 2021188812 | A1 | 9/2021 |
| WO | 2022187973 | A1 | 9/2022 |

OTHER PUBLICATIONS

Dwivedi, Evergreening: A deceptive device in patent rights, Technology in Society 32 (2010) 324-330.*

Examination Report No. 2 issued by the Australian Government for Application No. 2020386445 dated Oct. 22, 2025 (5 pages).

Canadian Patent Office Examination Report for Application No. 3, 158,059 dated Nov. 14, 2025 (4 pages).

Zheng et al., "Psilocybin for the treatment of Alzheimer's disease," Frontiers in Neuroscience, 2024, 18: 1420601 (20 pages).

Australian Patent Office. Examination Report No. 1 for Application No. 2020386445, dated Sep. 8, 2025 (6 pages).

Souza, L.C., et al. "Flavonoid Chrysin prevents age-related cognitive decline via attenuation of oxidative stress and modulation of BDNF levels in aged mouse brain." Pharmacology Biochemistry and Behavior 134 (2015): 22-30.

Stamets, "Paul Statemts: Psilocybin Mushrooms and The Mycology of Consciousness", M.A.P.S., Apr. 23, 2017, speech given, viewable on YouTube <https://www.youtube.com/watch?v=vFWxWqOFvOU>, 3 pages.

Stn Registry/Zregistry (CAS Registrysm) Sep. 2016 2 pages.

Szigeti et al., "Self-blinding citizen science to explore psychedelic microdosing," eLife, 2021, vol. 10, e62878.

Teng, F., et al. "Vitamin B12 [c-lactone], a biologically inactive corrinoid compound, occurs in cultured and dried lion's mane mushroom (Hericium erinaceus) fruiting bodies." Journal of agricultural and food chemistry 62.7 (2014): 1726-1732.

Third Party Submission in U.S. Appl. No. 17/669,845, dated Dec. 14, 2022 (30 pages).

Third Party Submission in U.S. Appl. No. 18/114,381 dated Sep. 20, 2023 (35 pages).

Third Party Submission in U.S. Appl. No. 18/115,966, dated Aug. 3, 2023 (27 pages).

Third Party Submission in U.S. Appl. No. 18/115,966, dated Aug. 3, 2023 (38 pages).

Third Party Submission in U.S. Appl. No. 18/498,563, dated Sep. 6, 2024 (57 pages).

Third Party Submission in U.S. Appl. No. 18/531,052, dated Dec. 6, 2023 (49 pages).

Third Party Submission in U.S. Appl. No. 18/531,407, dated Dec. 6, 2023 (54 pages).

Tsai-Teng et al., "Erinacine A-enriched Hericium erinaceus mycelium ameliorates Alzheimer's disease-related pathologies in APPswe/PS1dE9 transgenic mice", J Biomed Sci, 2016, vol. 23, No. 49, 12 pages.

Tsujikawa et al., "Analysis of hallucinogenic constituents in Amanita mushrooms circulated in Japan", Forensic Science International, 2006, vol. 164(2-3), pp. 172-178.

U.S. Environmental Protection Agency (EPA harmine) (Comptox Chemicals Dashboard. https://comptox.epa.gov/dashboard/chemical/details/DTXSI D30196066, Harmine, accessed Jul. 2023). (Year: 2023).

U.S. Environmental Protection Agency (EPA Norharmine) (Comptox Chemicals Dashboard. https://comptox.epa.gov/dashboard/ chemical/details/DTXSI D30431161, 7-Methoxy-9H-pyrido[3,4-b]indole) (Year: 2023).

Walpole, S.C. et al. The weight of nations: an estimation of adult human biomass. BMC Public Health (2012), 12, 439.

West, Solid State Chemistry and Its Applications, John Wiley & Sons, 1984 (3 pages).

Wieczorek (2015) "Chapter 5—Bioactive Alkaloids of Hallucinogenic Mushrooms" Studies in Natural Products Chemistry. 46: 133-168.

Wilcox (2014) "Psilocybin and Obsessive Compulsive Disorder" Journal of Psychoactive Drugs. 46:5(393-395).

Wolff, Burger's Medicinal Chemistry and Drug Discovery, vol. 1, Principles and Practice, John Wiley & Sons, New York, 1997 (4 pages).

Wronska et al., "Harman and norharman, metabolites of entomopathogenic fungus Conidiobolus coronatus (Entomophthorales), disorganized development of Galleria mellonella (Lepidoptera) and affect serotonin-regulating enzymes", PLoS One, 2018, vol. 13, No. 10, e0204828.

Yang et al., "Anti-inflammatory principles from Cordyceps sinensis", Journal of Natural Products, 2011, vol. 74, No. 9, pp. 1996-2000.

Yang et al., "Hericium erinaceus Mycelium Exerts Neuroprotective Effect in Parkinson's Disease-in vitro and in vivo Models", J Drug Res Dev, 2020, vol. 6, Issue 1, pp. 1-6.

Zhang et al., "Erinacerins, Novel Glioma Inhibitors from Hericium erinaceus, Induce Apoptosis of U87 Cells through Bax/Capase-2 Pathway," Anticancer Agents Med. Chem., 2020, 20(17): 2082-2088 (preprint).

Zhang, C., et al. "Somatostatin-positive GABAergic interneuron: new targets for depression." Molecular Psychiatry 22.6 (2017): 790-791.

Zhang, C.-C., et al. "Chemical constituents from Hericium erinaceus promote neuronal survival and potentiate neurite outgrowth via the TrkA/Erk1/2 pathway." International journal of molecular sciences 18.8 (2017): 1659.

Kasture et al., Mucuna pruriens seeds in treatment of Parkinson's disease: pharmacological review Orient Pharm Exp Med (2013) 13:165-174 (Year: 2013).

Kempuraj, D., et al. "COVID-19, mast cells, cytokine storm, psychological stress, and neuroinflammation." The Neuroscientist 26.5-6 (2020): 402-414.

Khalil and Elkheir, "Dimethyltryptamine from the leaves of certain Acacia species of northern Sudan" Lloydia 38(2): 176-177 (1975).

Kim "PubChem in 2021: new data content and improved web interfaces" Nucleic Acids Research, 2021, vol. 49, Database issue Published online Nov. 5, 2020 (8 pages).

Kim et al., "Hericium erinaceus (Lion's Mane) mushroom extracts inhibit metastasis of cancer cells to the lung in CT-26 colon cancer-transplanted mice", J. Agr. Food Chem., 2013, vol. 1, No. 20, pp. 4898-4904.

Klein, R. et al. The trkB Tyrosine Protein Kinase Is a Receptor for Brain-Derived Neurotrophic Factor and Neurotrophin-3. Cell (2009) 66 (2): 395-403.

Klein, R. et al. trkB, a novel tyrosine protein kinase receptor expressed during mouse neural development. EMBO J. (1989) 8(12); 3701-3709.

Koebler, A Brief History of Microdosing. Published Nov. 24, 2015, publisher Vice, URL: https://www.vice.com/en/article/begv5p5y/a-brief-history-of-microdosing (6 pages).

Kraehenmann et al., "Psilocybin-Induced Decrease in Amygdala Reactivity Correlates with Enhanced Positive Mood in Health Volunteers", Biological Psychiatry, vol. 78, 2015, pp. 572-581.

(56) References Cited

OTHER PUBLICATIONS

Kuypers et al., "Microdosing psychedelics: More questions than answers? An overview and suggestions for future research", J. Psychopharmacol., 2019, vol. 33, No. 9, pp. 1039-1057.
Lake, Some Vitamins and Minerals May Reduce Alcohol Toxicity: Promising findings for certain B vitamins, vitamin C, magnesium and zinc, Jan. 29, 2019, retrieved from Psychology Today, Jan. 29, 2019, https://www.psychologytoday.com/us/blog/integrative-mental-health-care/201901/some-vitamins-and-minerals-may-reduce-alcohol-toxicity.
Latham et al., "Development of Halogenase Enzymes for Use in Synthesis", Chemical Reviews, vol. 118, 2018, pp. 232-269.
Lenz et al., "Identification of omega-Methyl-4-hydroxytryptamine (norpsilocin) as a Psilocybe natural product", J. Nat. Prod, vol. 80, No. 10, 2017, pp. 2835-2838.
Leung, A. Y., et al. "Baeocystin and norbaeocystin: new analogs of psilocybin from Psilocybe baeocystis." Journal of Pharmaceutical Sciences 57.10 (1968): 1667-1671.
Licht et al., "Simultaneous polysubstance use among Danish 3,4-methylenedioxymethamphetamine and hallucinogen users: combination patterns and proposed biological bases", Hum. Psychopharmacol. Clin. Exp., 2012, vol. 27, pp. 352-363.
Liu, Y.-H., et al. "Group A streptococcus subcutaneous infection-induced central nervous system inflammation is attenuated by blocking peripheral TNF." Frontiers in Microbiology 10 (2019): 265.
Ly et al., "Psychedelics Promote Structural and Functional Neural Plasticity," Cell Rep., 2018, 23: 3170-3182.
Ma, et al. "Hericenones and erinacines: stimulators of nerve growth factor (NGF) biosynthesis in Hericium erinaceus," Mycology, 2010, 1:2, 92-98.
Machado Thesis: The Frontiers of Psychedelic Therapy—Psilocybin as a New T. Universidade de Aveiro Ano 2014-2015 https://ria.ua.pt/bitstream/10773/14878/z/As%20fronteiras%20da%20pscioterapia%20psicad%C3%A9lica/pdf (Year: 2015) (72 pages).
Mahmood, Z.A. "Bioactive alkaloids from fungi: Psilocybin." Natural products: phytochemistry, botany and metabolism of alkaloids, phenolics and terpenes. Springer-Verlag, Berlin Heidelberg (2013): 523-552.
Mattila (2001) "Contents of vitamins, mineral elements, and some phenolic compounds in cultivated mushrooms" Journal of Agricultural and Food Chemistry. 49(5): 2343-2348.
Mccandless, Goodbye ecstasy, hello 5-Meo-DMT: new designer drugs are just a click away Psychedelics legal in US but banned in UK are openly available on the internet. The Guardian, Society, Feb. 15, 2004. https://www.theguardian.com/society/2004/feb/16/drugsandalcohol.drugs?CM P=share_btn_link (Year: 2004) (4 pages).
Mckenna et al., "Monoamine Oxidase Inhibitors in South American Hallucinogenic Plants Parts 2: Constituents of Orally-Active Myristicaceous Hallucinogens", Journal of Ethnopharmacology, vol. 12, 1984, pp. 179-211.
Moir, A. T. B., et al. "The effects of precursor loading in the cerebral metabolism of 5-hydroxyindoles." Journal of Neurochemistry 15.10 (1968): 1093-1108 (16 pages).
Moreno, F. A., et al. "Safety, tolerability, and efficacy of psilocybin in 9 patients with obsessive-compulsive disorder." Journal of clinical Psychiatry 67.11 (2006): 1735-1740.
Mori et al., "Improving effects of the mushroom yamabushitake (Hericium erinaceus) on mild cognitive impairment: A double-blind placebo-controlled clinical trial", Phytotherapy Research, 2009, vol. 23, pp. 367-372.
Mori et al., "Nerve growth factor-inducing activity of Hericium erinaceus in 1321N1 human astrocytoma cells", Biological & pharmaceutical bulletin, 2008, vol. 31, No. 9, pp. 1727-1732.
Nagano et al., "Reduction of depression and anxiety by 4 weeks Hericium erinaceus intake", Biomedical Research, 2010, vol. 31, No. 4, pp. 231-237.
O'Mahony Carey, Report, Health Service Executive (HSE) South, Psychoactive substances: a guide to ethnobotanical plants and herbs, synthetic chemicals, compounds and products , http://hdl.handle.net/10147/112933 Issue date Jul. 2010 (Year: 2010) (6 pages).
Passie et al., "The Pharmacology of Psilocybin," Addiction Biol., 2002, 7:357-364.
Patel, "Recent Developments in mushrooms as anti-cancer therapeutics: a review", Biotech, 2012, vol. 3, No. 2, pp. 1-15.
Phan et al., "Edible and Medicinal Mushrooms: Emerging Brain Food for the Mitigation of Neurodegenerative Diseases," J. Medicinal Foods, 2017, 20(1):1-10.
Phan, C.-W., et al. "Hericium erinaceus (Bull.: Fr) Pers. cultivated under tropical conditions: isolation of hericenones and demonstration of NGF-mediated neurite outgrowth in PC12 cells via MEK/ERK and PI3K-Akt signaling pathways." Food & Function 5.12 (2014): 3160-3169.
Piechowska et al., "Bioactive β-carbolines in food: A review", Nutrients, 2019, vol. 11, No. 4, pp. 814.
Polito et al., A systematic study of microdosing psychedelics, 2019, PLoS One, vol. 14, No. 2, e0211023.
Prencipe, G., et al. "Nerve growth factor downregulates inflammatory response in human monocytes through TrkA." The Journal of Immunology 192.7 (2014): 3345-3354.
Prousky, "Vitamin B3 for Depression: Case Report and Review of the Literature", JOM, 2010, vol. 25, No. 3, pp. 137-147.
Psilocybin, Wikepedia, The Free Encyclopedia, 2018.
Psilolover333, "Virgin Beauty Blossoming Consciousness Mushrooms—P. cubensis" Jan. 13, 2016; retrieved from Erowid Experience Vaults. Https://erowid.org/experiences/exp.php?ID=107678, retrieved Jan. 13, 2016 (1 page).
PSOOD0NYM, "4-Ho-NMT" 2007; retrieved from Bluelight.org comment. https://bluelight.org/xf/threads/4-ho-nmt.321417/, retrieved Jun. 18, 2007.
Rambousek et al., "The effect of psilocin on memory acquisition, retrieval, and consolidation in the rat," Frontiers in Behavioral Neuroscience, 2014, 8:1-7.
Reynolds, H. et al., "Horizontal gene cluster transfer increased hallucinogenic mushroom diversity," Evolution Letters, 2018, 2-2:88-101.
Riba et al., "Metabolism and disposition of N, N-dimethyltryptamine and harmala alkaloids after oral administration of ayahuasca", Drug Test Anal., 2012, vol. 4, pp. 610-616.
Sabaratnam, V., et al. "Neuronal health-can culinary and medicinal mushrooms help?." Journal of traditional and complementary medicine 3.1 (2013): 62-68.
Samoylenko, V., et al. "Banisteriopsis caapi, a unique combination of MAO inhibitory and antioxidative constituents for the activities relevant to neurodegenerative disorders and Parkinson's disease." Journal of ethnopharmacology 127.2 (2010): 357-367.
Sarris et al., "Plant-Based Medicines for Anxiety Disorders, Part 2: A Reivew of Clinical Studies with Supporting Preclinical Evidence", CNS Drugs, 2013, vol. 27, pp. 301-319.
Saul, "Treating ADHD with Vitamin B-3 (Niacinamide)" Oct. 30, 2013; retrieved from Orthomolecular.org. http://orthomolecular.org/resources/omns/v09n23.shtml, retrieved on Oct. 30, 2013.
Schartner et al., "Increased spontaneous MEG signal diversity for psychoactive doses of ketamine, LSD and psilocybin," Nature Sci Reports, 2017, 7:46421.
Sherwood et al. "Synthesis and Biological Evaluation of Tryptamines Found in Hallucinogenic Mushrooms: Norbaeocystin, Baeocystin, Norpsilocin, and Aeruginascin," J. Nat. Prod., 2020, 83 (2): 461-467.
Shroomery User, ILOVEMAGICMUSHROOMS, "Micro dosing for anxiety" Published Oct. 27, 2015, URL: https://www.shroomery.org/forums/showflat.php/Number/22441404 (8 pages).
European Patent Office, Extended European Search Report for Application No. 22799722.8, dated Mar. 20, 2025 (10 pages).
Diaz, P., et al. "Antioxidant and anti-inflammatory activities of selected medicinal plants and fungi containing phenolic and flavonoid compounds." Chinese medicine 7 (2012): 1-9.
Standiford, T. J. "Anti-inflammatory cytokines and cytokine antagonists." Current Pharmaceutical Design 6.6 (2000): 633-649.
Kamanna, V. S., et al. "Mechanism of action of niacin." The American journal of cardiology 101.8 (2008): S20-S26.

(56) References Cited

OTHER PUBLICATIONS

Ostadkarampour, M. et al. "Monoamine oxidase inhibitors: a review of their anti-inflammatory therapeutic potential and mechanisms of action." Frontiers in pharmacology 12 (2021): 676239.
Wang, L.-Y., et al. "Anti-inflammatory effect of erinacine C on NO production through down-regulation of NF-κB and activation of Nrf2-mediated HO-1 in BV2 microglial cells treated with LPS." Molecules 24.18 (2019): 3317.
European Patent Office. Office Action for Application No. 20890349.2, dated Jun. 3, 2025 (5 pages).
"Amount of niacin in mushrooms," <http://dietandfitnesstoday.com/niacin-in-mushrooms.php> May 28, 2019.
"Find ETDs Home > Thesis Resources> Find ETDs" Online: "https://ndltd.org/thesis-resources/find-etds/" Accessed Jan. 31, 2023 (7 pages).
"Comorbid." Mirriam-Webster.com Dictionary. Merriam-Webster. https://www.merriam-webster.com/dictionary/cobmorbid. Last updated Aug. 14, 2024 (6 pages).
"Human Body Weight." Wikipedia. https://en.wikipedia.org/wiki/Human_body_weight (17 pages).
Bartlett "Exploiting Chemical Diversity for Drug Discovery" Edited by Paul A Bartlett and Michael Entzeroth, The Royal Society of Chemistry, 2006, pp. 113-118.
Beug et al., "Psilocybin and psilocin levels in twenty species from seven genera of wild mushrooms in the Pacific Northwest, U.S.A.", J. Ethnopharmacology, 1982, vol. 5, No. 3, pp. 271-285.
Blei et al., "Simultaneous Production of Psilocybin and a Cocktail of β-Carboline Monoamine Oxidase Inhibitors in 'Magic' Mushrooms," Chem. Eur. J., 2020, 26:729-734.
Byock, I. "Taking psychedelics seriously." Journal of palliative medicine 21.4 (2018): 417-421.
Calabrese, F., et al. (2009). Neuronal plasticity: A link between stress and mood disorders. Psychoneuroendocrinology, 34 (Suppl 1), S208-S216.
Carhart-Harris et al., "Psilocybin with psychological support for treatment-resistant depression: an open-label feasibility study", Lancet Psychiatry, vol. 3, 2016, pp. 619-627.
Carhart-Harris, R. L., et al. "Implications for psychedelic-assisted psychotherapy: functional magnetic resonance imaging study with psilocybin." The British Journal of Psychiatry 200.3 (2012): 238-244.
Carod-Artal, Hallucinogens in Pre-Columbian Mesoamerican Cultures Neurology, 2015, vol. 30, Issue 1, Jan.-Feb. 2015, pp. 42-49.
Catlow et al., "Effects of psilocybin in hippocampal neurogenesis and extinction of trace fear conditioning," Exp. Brain Res., 2013, 228:481-491.
Chaiyasut et al., "Anti-hyperglycemic property of Hericium erinaceus—A Mini Review", Asian Pac. J. Trop. Biomed., vol. 7, No. 11, 2017, pp. 1036-1040.
Chong et al., "Therapeutic Potential of Hericium erinaceus for Depressive Disorder", International Journal of Molecular Sciences, 2020, vol. 21, No. 1, 163.
Chycho, "The Boundary Salvia divinorum, Fasting & Mushrooms—P. cubensis" Apr. 9, 2007; retrieved from Erowid; retrieved from Web Archives. https://web.archive.org/web/20220916125803/https:/www.erowid.org/experiences/exp.php?ID=5323 (2 pages).
Davis et al., "Differential Immune Activating, Anti-Inflammatory, and Regenerative Properties of the Aqueous, Ethanol, and Solid Fractions of a Medicinal Mushroom Blend", J. Inflammation Res., vol. 13, 2020, pp. 117-131.
De la Fuente Revenga et al., "Neurogenic potential assessment and pharmacological characterization of 6-Methoxy-1,2,3,4-tetrahydro-β-carboline (pinoline) and melatonin-pinoline hybrids", ACS Chemical Neuroscience, 2015, vol. 6, No. 5, pp. 800-810.
DMT-Nexus, "Known substance-interactions and their effects", <https://wiki.dmt-nexus.me/Known-substance-interactions_and_their_effects>, 2013, 1 page.
Drugs.com, "lovie . . . Taken for 1 to 6 months Jul. 12, 2018" Jul. 12, 2018; retrieved from Drugs.com comment. https://www.drugs.com/comments/niacin/for-depression.html, retrieved Jul. 12, 2018.
Dunst, J et al. "Cytokines and chemokines in cerebral malaria pathogenesis." Frontiers in cellular and infection microbiology 7 (2017): 324.
Erowid, "Psilocybin, Psilocin, and Magic Mushroom Dosage" Jan. 18, 2013; retrieved from Erowid; retrieved from Web Archives. https://web.archive.org/web/20130118160500/https:/erowid.org/plants/mushrooms/mushrooms dose.shtml, retrieved Jan. 18, 2013 (1 page).
European Patent Office, Extended European Search Report for Application No. 20890349.2, dated Mar. 18, 2024 (16 pages).
Fadiman, "Might Microdosing Psychedelics Be Safe and Beneficial? An Initial Exploration", J Psychoactive Drugs, 2019, vol. 51, No. 2, pp. 118-122.
Fadiman, J. "Microdose research: Without approvals, control groups, double-blinds, staff or funding." Psychedelic Press 15 (2016): 53-59.
Ferreira, et al., "Ketamine can be produced by Pochonia chlamydosporia: an old molecule and a new anthelmintic?," Parasites & Vectors, 2020, 13 (527): 1-9.
Fink, C.C. et al. Selective Regulation of Neurite Extension and Synapse Formation by the β but not the a Isoform of CaMKII. Neuron (2003)39 (2): 283-297.
Flannagan and Nichols, Psychedelics as anti-inflammatory agents, Int. Rev. Psychiatry, 2018, 30(4): 363-375.
Friedman et al., "Chemistry, Nutrition, and Health-Promoting Properties of Hericium ennaceus (Lion's Mane) Mushroom Fruiting Bodies and Mycelia and their Bioactive Compounds," J. Agricult. Food Chem., 2015, 63:7108-7123.
Gambaro et al., "DNA-based taxonomic identification of basidiospores in hallucinogenic mushrooms cultivated in "grow-kits" seized by the police: LC-UV quali-quantitative determination of psilocybin and psilocin", J. Pharmac. Biomed. Anal., 2016, vol. 125, pp. 427-432.
Garcia-Romeu (2015) "Psilocybin-occasioned Mystical Experiences in the Treatment of Tobacco Addiction" Current Drug Abuse Reviews. 7:3(157-164).
Gartz (1994) "Extraction and analysis of indole derivatives from fungal biomass" Journal of Basic Microbiology. 34(1): 17-22.
Gartz et al., "Analysis and Cultivation of Fruit Bodies and Mycelia of Psilocybe bohemica", Biochemie und Physiologie der Pflanzen, 1989, vol. 184, pp. 337-341.
Gartz et al., "Biotransformation of Tryptamine in Fruiting Mycelia of Psilocybe cubensis", Planta Med., 1989, vol. 55, No. 3, pp. 249-250.
Gartz, "Further Investigations on Pyschoactive Mushrooms of the Genera Psilocybe, Gymnopilus and Conocybe", Ann Mus Civ Rovereto, 1992, vol. 7, pp. 265-274.
Griffiths et al., "Psilocybin produces sbstantial and sustained decreases in depression and anxiety in patients with life- threatening cancer: A randomized double-blind trial", Journal of Psychopharmacology, vol. 30, No. 12, 2016, pp. 1181-1197.
Griffiths, R. R., et al. "Psilocybin occasioned mystical-type experiences: immediate and persisting dose-related effects." Psychopharmacology 218 (2011): 649-665.
Grob et al., "Pilot Study of Psilocybin Treatment for Anxiety in Patients With Advanced-Stage Cancer", Arch Gen Psychiatry, 2011, vol. 68, No. 1, pp. 71-78.
Gupta, V.K., et al. TrkB Receptor Signaling: Implications in Neurodegenerative, Psychiatric, and Proliferative Disorders, Int. J. Mol. Sci. (2013) 14(5): 10122-10142.
Halberstadt, A.L. Recent Advances in the Neuropharmacology of Serotonergic Hallucinogens. Behav. Brain Res. (2015) 277, 99-120.
Han, J. et al. "An overview of mammalian p38 mitogen-activated protein kinases, central regulators of cell stress and receptor signaling." F1000Research 9 (2020).
Herraiz et al., "β-Carboline alkaloids in Peganum harmala and inhibition of human monoamine oxidase (MAO)", Food and Chemical Toxicology, 2010, vol. 48, No. 3, pp. 839-845.
Hutten et al., "Self-Rated Effectiveness of Microdosing With Psychedelics for Mental and Physical Health Problems Among Microdosers", Front. Psychiatry, 2019, vol. 10, Article 672, 9 pages.
International Search Report and Written Opinion for Application No. PCT/US20/60947 dated Mar. 17, 2021 (17 pages).

(56) References Cited

OTHER PUBLICATIONS

International Search Report and Written Opinion for Application No. PCT/US2022/028181 dated Sep. 23, 2022 (15 pages).
Irwin "ZINC—A Free Database of Commercially Available Compounds for Virtual Screening" J. Chem. Inf. Model. 2005, 45, 177-182.
J, "My Cognition Improves Tremendously: Mushrooms & Amphetamines (Adderall XR)" Aug. 11, 2018; retrieved from Erowid. https://erowid.org/experiences/exp.php?ID=I 11984, retrieved Aug. 11, 2018.
Jackowski, "Neural injury repair: hope for the future as barriers to effective CNS regeneration become clearer," Brittish J. of Neurosurgery, 1995, 9:303-317.
Julson, "16 Foods That Are High in Niacin (Vitamin B3)" Oct. 5, 2018; retrieved from WaybackMachine Internet Archive, Healthline. https://web.archive.org/web/20 I 90507 II 3644/https://www.healthline.com/nutrition/food ··high-in-niacin, retrieved May 7, 2019.
Kaertner et al., "Positive expectations predict improved mental-health outcomes linked to psychedelic microdosing," Nature Sci. Rep., 2021, vol. 11, 1941.
European Patent Office. Office Action for Application No. 20890349.2, dated Feb. 10, 2026 (6 pages).

* cited by examiner

FIG. 6

| | 1 | 2 | 3 | 4 | 5 | 6 | 7 | 8 | 9 | 10 | 11 | 12 |
|---|---|---|---|---|---|---|---|---|---|---|---|---|
| A | HE Myc 62.5 µg/mL | HE Myc 62.5 µg/mL | HE Myc 62.5 µg/mL | Norpsilocin 1 µg/mL | Norpsilocin 1 µg/mL | Norpsilocin 1 µg/mL | He/Baeo 31.25/0.25 µg/mL | He/Baeo 31.25/0.25 µg/mL | He/Baeo 31.25/0.25 µg/mL | He/Norbaeo 62.5/0.5 µg/mL | He/Norbaeo 62.5/0.5 µg/mL | He/Norbaeo 62.5/0.5 µg/mL |
| B | HE Myc 31.25 µg/mL | HE Myc 31.25 µg/mL | HE Myc 31.25 µg/mL | Norpsilocin 0.5 µg/mL | Norpsilocin 0.5 µg/mL | Norpsilocin 0.5 µg/mL | He/Norpsilo 62.5/1 µg/mL | He/Norpsilo 62.5/1 µg/mL | He/Norpsilo 62.5/1 µg/mL | He/Norbaeo 62.5/0.25 µg/mL | He/Norbaeo 62.5/0.25 µg/mL | He/Norbaeo 62.5/0.25 µg/mL |
| C | Baeocystin 1 µg/mL | Baeocystin 1 µg/mL | Baeocystin 1 µg/mL | Norpsilocin 0.25 µg/mL | Norpsilocin 0.25 µg/mL | Norpsilocin 0.25 µg/mL | HE/Norpsilo 62.5/0.5 µg/mL | HE/Norpsilo 62.5/0.5 µg/mL | HE/Norpsilo 62.5/0.5 µg/mL | He/Norbaeo 31.25/1 µg/mL | He/Norbaeo 31.25/1 µg/mL | He/Norbaeo 31.25/1 µg/mL |
| D | Baeocystin 0.5 µg/mL | Baeocystin 0.5 µg/mL | Baeocystin 0.5 µg/mL | He/Baeo 62.5/1 µg/mL | He/Baeo 62.5/1 µg/mL | He/Baeo 62.5/1 µg/mL | HE/Norpsilo 62.5/0.25 µg/mL | HE/Norpsilo 62.5/0.25 µg/mL | HE/Norpsilo 62.5/0.25 µg/mL | He/Norbaeo 31.25/0.5 µg/mL | He/Norbaeo 31.25/0.5 µg/mL | He/Norbaeo 31.25/0.5 µg/mL |
| E | Baeocystin 0.25 µg/mL | Baeocystin 0.25 µg/mL | Baeocystin 0.25 µg/mL | HE/Baeo 62.5/0.5 µg/mL | HE/Baeo 62.5/0.5 µg/mL | HE/Baeo 62.5/0.5 µg/mL | He/Norpsilo 31.25/1 µg/mL | He/Norpsilo 31.25/1 µg/mL | He/Norpsilo 31.25/1 µg/mL | He/Norbaeo 31.25/0.25 µg/mL | He/Norbaeo 31.25/0.25 µg/mL | He/Norbaeo 31.25/0.25 µg/mL |
| F | Norbaeocysti n 1 µg/mL | Norbaeocysti n 1 µg/mL | Norbaeocysti n 1 µg/mL | HE/Baeo 62.5/0.25 µg/mL | HE/Baeo 62.5/0.25 µg/mL | HE/Baeo 62.5/0.25 µg/mL | He/Norpsilo 31.25/0.5 µg/mL | He/Norpsilo 31.25/0.5 µg/mL | He/Norpsilo 31.25/0.5 µg/mL | Negative Control | Negative Control | NGF 50 ng/mL |
| G | Norbaeocysti n 0.5 µg/mL | Norbaeocysti n 0.5 µg/mL | Norbaeocysti n 0.5 µg/mL | He/Baeo 31.25/1 µg/mL | He/Baeo 31.25/1 µg/mL | He/Baeo 31.25/1 µg/mL | He/Norpsilo 31.25/0.25 µg/mL | He/Norpsilo 31.25/0.25 µg/mL | He/Norpsilo 31.25/0.25 µg/mL | Negative Control | Negative Control | NGF 50 ng/mL |
| H | Norbaeocysti n 0.25 µg/mL | Norbaeocysti n 0.25 µg/mL | Norbaeocysti n 0.25 µg/mL | He/Baeo 31.25/0.5 µg/mL | He/Baeo 31.25/0.5 µg/mL | He/Baeo 31.25/0.5 µg/mL | He/Norbaeo 62.5/1 µg/mL | He/Norbaeo 62.5/1 µg/mL | He/Norbaeo 62.5/1 µg/mL | Negative Control | NGF 50 ng/mL | NGF 50 ng/mL |

MAP Kinase Binding of HE Extracts and Powder

TRYPTAMINE COMPOSITIONS FOR ENHANCING NEURITE OUTGROWTH

CROSS-REFERENCE TO RELATED APPLICATIONS

This application is a continuation of U.S. patent application Ser. No. 18/475,724, filed Sep. 27, 2023, which is a continuation of U.S. patent application Ser. No. 17/570,054, filed Jan. 6, 2022, which is a continuation of U.S. patent application Ser. No. 16/951,009, filed Nov. 18, 2020, which claims priority to U.S. Provisional Patent Application No. 62/937,536, filed on Nov. 19, 2019, and U.S. Provisional No. 63/007,482, filed Apr. 9, 2020, each of which are incorporated by reference herein in its entirety.

TECHNICAL FIELD

Described herein are neurotrophic and nootropic compositions and methods for treating subjects with such compositions. In one aspect the composition comprises one or more tryptamines or in pure form or extracts from psilocybin containing mushrooms, or combinations thereof optionally combined with one or more phenethylamines or amphetamines in pure form or extracts from a plant or mushroom, or combinations thereof, optionally one or more erinacines or hericenones in pure form, extracts from Hericium mushroom species (e.g., H. *erinaceus, H. coralloides, H. ramosum*) or combinations thereof, optionally one or more cannabinoids in pure form or extracts from *Cannabis sativa, Cannabis sativa, Cannabis indica*, or *Cannabis ruderalis*, optionally, one or more adversive compounds, and optionally one or more pharmaceutically acceptable excipients.

BACKGROUND

Serotonin (5-hydroxytryptamine, 5-HT) plays a significant role in influencing many central and peripheral processes. 5-HT-selective pharmacotherapies have been developed to treat a wide variety of medical problems including depression, anxiety, schizophrenia, migraine, emesis, and appetite control. 5-HT exerts its influence through activation of fourteen distinct receptor subtypes in seven separate families. There is interest in the three receptor subtypes of the 5-$HT_2$ family, 5-$HT_{2A}$, 5-$HT_{2B}$, and 5-$HT_{2C}$. Modulation of the 5-$HT_{2C}$ receptor subtype has been shown to play a role in numerous human diseases including obesity, obsessive-compulsive disorder (OCD), sexual dysfunction, epilepsy, schizophrenia, anxiety disorders, among a variety of other psychiatric disorders.

Psilocybin (4-phosphoryloxy-N,N-dimethyltryptamine) is an agonist at the 5-$HT_{2A}$ and 5-$HT_{2C}$ receptors. Psilocybin's binding potency at 5-$HT_{2A}$ correlates with its activity as a hallucinogen in humans. More than 40 years ago, derivatives of psilocybin were reported by workers at Sandoz. See Hofmann and Troxler, U.S. Pat. Nos. 3,075,992; 3,078,214. Recent studies have shown that psilocybin has neurogenerative properties. See Catlow et al., "Effects of psilocybin on hippocampal neurogenesis and extinction of trace fear conditioning," *Expt. Brain Res.* 228: 481-491 (2013); Phan et al. "*Edible and Medicinal Mushrooms*: Emerging Brain Food for the Mitigation of Neurodegenerative Diseases," *J. Medic. Foods* 20(1): 1-10 (2017). Schartner et al. reported substantial increased global neural signal diversity in a psilocybin-human clinical study. See *Nature Scientific Reports,* 7:46421 (2017). And, Ly et al. showed that dimethyltryptamine, 2,5-dimethoxy-4-iodoamphetamine (DOI), and LSD promoted neurogenesis. See Ly et al., "Psychedelics Promote Structural and Functional Neural Plasticity," *Cell Rep.* 23: 3170-3182 (2018). Recent studies have shown that monoamine oxidase (MAO) inhibitors increase the pharmacological effects of tryptamines. See Blei et al., "Simultaneous Production of Psilocybin and a Cocktail of β-Carboline Monoamine Oxidase Inhibitors in '*Magic' Mushrooms," Chem. Eur. J.* 26(3): 729-734 (2020).

Lion's Mane (Hericium *erinaceus*), Bear's Head (H. *coralloides*), or Comb Tooth (H. *ramosum*) mushrooms and mycelium are reported to influence myelin regeneration myelin on the axons of nerves. Two cyanthane terpenes the erinacines and hericenones are thought to promote NGF (nerve growth factor) synthesis. See Friedman, "*Chemistry, Nutrition, and Health-Promoting Properties of Hericium erinaceus* (Lion's Mane) Mushroom Fruiting Bodies and Mycelia and Their Bioactive Compounds," J. Agricult. *Food Chem.* 63: 7108-7123 (2015). Recent studies have identified erinacines O and P as inhibitors of gliomas in human U87 cells. Zhang et al., "Erinacerins, Novel Glioma Inhibitors from Hericium *erinaceus*, Induce Apoptosis of U87 Cells through Bax/Capase-2 Pathway," *Anticancer Agents Med. Chem.* Aug. 3, 2020; doi: 10.2174/1871520620666200804104243.

The combination of sub-hallucinogenic "microdoses" of tryptamines, phenethylamines, or amphetamines with other neurogenic compounds such as the erinacines and hericenones, cannabinoids and other neurogenic or nootropic natural products can be used to treat a variety of neuronal disorders or enhance cognition and sensory motor neuron functioning. There is a need for such neurogenic and nootropic compositions.

SUMMARY

One embodiment described herein is a composition comprising norpsilocin or a salt or hydrate thereof or combinations thereof combined with one or more erinacines or hericenones in pure form, extracts or isolates from Hericium mushroom species, or combinations thereof. In one aspect, the erinacines or hericenones comprise Erinacine A, Erinacine B, Erinacine C, Erinacine D, Erinacine E, Erinacine F, Erinacine G, Erinacine H, Erinacine I, Erinacine J, Erinacine K, Erinacine O, Erinacine P, Erinacine Q, Erinacine R, Erinacol, other Erinacines Hericenone A, Hericenone B, Hericenone C, Hericenone D, Hericenone E, Hericenone F, Hericenone G, Hericenone H, other hericenones, or pharmaceutically acceptable salts, hydrates, solvates, prodrugs, stereoisomers, or tautomers thereof. In another aspect, the composition comprises an extract of extracts or isolates from Hericium *erinaceus*. In another aspect, the composition further comprises baeocystin or a salt or hydrate thereof. In another aspect, the composition comprises norbaeocystin and a purified erinacine, hericenone, salts thereof, hydrates thereof, or combination thereof. In another aspect, the composition further comprises one or more cannabinoids in pure form or extracts or isolates from *Cannabis sativa, Cannabis sativa, Cannabis indica*, or *Cannabis ruderalis*. In another aspect, the cannabinoids comprise one or more of Δ8-tetrahydrocannabinol (THC), Δ9-tetrahydrocannabinol, tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), among others, or pharmaceutically acceptable salts, hydrates, solvates, prodrugs, stereoisomers, or tautomers thereof. In another aspect, the composition further comprises one or more phenethylamines or amphetamines in pure form or extracts or isolates from plants comprising thereof. In another aspect, the phenethylamines or amphetamines comprises 3,4,5-trimethoxyphenethylamine (Mescaline), 2,5-dimethoxy-4-methylamphetamine (DOM), 2,5-dimethoxy-4-bromophenethylamine (2C-B), 2,5-dimethoxy-4-ethylphenethylamine (2C-E), 2,5-dimethoxy-4-ethylthiophenethylamine (2C-T-2), 2,5-dimethoxy-4-propylthiophenethylamine (2C-T-7), p-methoxy-amphetamine (PMA), 2,4-dimethoxy-amphetamine (2,4-DMA), 3,4-dimethoxy-amphetamine (3,4-DMA), 3,4-methylenedioxy-amphetamine (MDA), 3-methoxy-4,5-methylendioxy-amphetamine (MMDA), 2-methoxy-3,4-methylendioxyamphetamine (MMDA-3a), 2-methoxy-4,5-methylendioxyamphetamine (MMDA-2), 3,4,5-trimethoxyamphetamine (TMA), 2,4,5-trimethoxyamphetamine (TMA-2), 2,5-dimethoxy-3,4-methylenedioxyamphetamine (DMMDA), 2,3-dimethoxy-4,5-methylenedioxyamphetamine (DMMDA-2), 2,3,4,5-tetramethoxyamphetamine (TeMA), (R)-2,5-dimethoxy-4-iodoamphetamine, inter alia, pharmaceutically acceptable salts, hydrates, solvates, prodrugs, stereoisomers, or tautomers thereof. In another aspect, the composition further comprises one or more adversive compounds comprising niacin, ipecac, apomorphine, bittering agents (e.g., denatonium benzoate), capsaicin, capsacutin dihydrocapsaicin, nordihydrocapsaicin, homocapsaicin, homodihydrocapsaicin, capsaicinoids, gingerol, piperine, isopiperine, zingerone, shogaol, vanillylamide derivatives, or combinations thereof. In another aspect, the adversive is niacin. In another aspect, the composition comprises an extract of extracts or isolates from Hericium *erinaceus* and niacin. In another aspect, the composition comprises an extract of extracts or isolates from Pochonia chlamydosporia. In another aspect, the composition comprises ketamine, pharmaceutically acceptable salts, hydrates, solvates, prodrugs, stereoisomers, or tautomers thereof. In another aspect, the composition comprises 0.001 mg to 0.01 mg, 0.01 mg to 0.1 mg, 0.01 mg to 1 mg, 0.1 mg to 5 mg, 0.1 mg to 1 mg, 0.5 mg to 1 mg, 0.5 mg to 5 mg, 0.25 mg to 1 mg, 0.2 mg to 2 mg, or 0.2 mg to 5 mg of norpsilocin or an amount of a mushroom extract or mushroom to provide an equivalent dose. In another aspect, the composition comprises 1 μg to 5 μg, 1 μg to 10 μg, 5 μg to 10 μg, 10 μg to 5 mg, 10 μg to 100 μg, 100 μg to 1 mg, 500 μg to 1 mg, 500 μg to 5 mg, 1 mg to 5 mg, 100 μg to 1 mg, 100 μg to 500 μg, 100 μg to 250 μg; 250 μg to 1 mg; 750 μg to 1 mg, or 250 μg to 750 μg of one or more erinacines or hericenones or an amount of a mushroom extract or mushroom to provide an equivalent dose. In another aspect, the composition comprises 0.01 mg to 0.1 mg, 0.01 mg to 1 mg, 0.1 mg to 10 mg, 0.1 mg to 1 mg, 0.5 mg to 1 mg, 0.5 mg to 5 mg, 0.25 mg to 1 mg, 0.2 mg to 2 mg, 0.2 mg to 5 mg, or 1 mg to 10 mg of one or more cannabinoids or an amount of a plant extract or plant to provide an equivalent dose. In another aspect, the composition comprises 0.1 mg to 1 mg, 1 mg to 10 mg, 10 mg to 100 mg, 10 mg to 50 mg, 50 mg to 100 mg, 20 mg to 80 mg, 20 mg to 50 mg, 50 mg to 100 mg, 50 mg to 80 mg, or 10 mg to 80 mg of one or more phenethylamines or amphetamines or an amount of a plant or mushroom extract or plant or mushroom to provide an equivalent dose. In another aspect, the composition comprises 0.1 mg to 10 mg, 1 mg to 500 mg, 1 mg to 100 mg, 200 mg to 500 mg, 50 mg to 200 mg, 10 mg to 50 mg, 50 mg to 200 mg, 1 mg to 200 mg, or 1 mg to 50 mg of one or more adversives. In another aspect, the composition comprises one or more pharmaceutically acceptable excipients. In another aspect, the composition is a powder admixture, liquid, suspension, or emulsion. In another aspect, the composition further comprises one or more extracts or pure chemicals from other fungi comprising one or more of, Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof; a mycelium extract of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof; or a fruiting body extract of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof, or combinations thereof. In another aspect, the composition further comprises one or more extracts or pure chemicals from other plant species comprising Bacopa species (Bacopa monnien), Gotu kola (Centella *asiatica*), and Gingko (Gingko *biloba*, Ginger (*Zingiber officinale*), Holy Basil (*Ocimum* sanctum), Hu Zhang (*Polygonum cuspidatum*), Oregano (*Origanum vulgare, Origanum* onites), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula* spica and related species in the genus *Lavandula*), skullcap (Scutellaria lateriflora) oat straw (*Avena sativa, Avena byzantina*), *Salvia* divinorum, aka Diviner's Sage, Banisteriopsis caapi and Psychotria species, plants containing ibogaine (Tabemanthe iboga, Voacanga *africana* and Tabemaemontana undulate), peyote (Lophophora williamsil), the seeds of morning glory (*Ipomoea tricolor* and related species) and Hawaiian baby wood rose (Argyreia nervosa), Acacia *confusa, Acacia obtusifolia, Acacia simplicifolia*, Desmanthus Illinoensis, or *Cannabis* (*Cannabis sativa, C. indica* and *C. ruderalis*) or combinations thereof. In another aspect, the composition is effective to treat, alleviate, prevent or ameliorate psychiatric and mood disorders comprising serotonin (5-hydroxytryptamine, 5-HT) receptor disorders, depression, anxiety, major depressive disorder, treatment resistant depression, persistent depression, manic depression or bipolar disorder, depressive psychosis, perinatal depression, premenstrual dysphoric disorder, seasonal depressions, situational depression, panic disorder, obsessive compulsive disorder, post-traumatic stress disorder, attention deficit/hyperactivity disorder, sleep disorders, eating disorders, schizophrenia, personality disorders, substance abuse disorders (drug abuse, addiction, alcoholism); neuronal injuries or physical neurodegeneration (e.g., physical injury, head trauma, spinal cord trauma, concussion, peripheral neuron trauma, paralysis, ischemia, hypoxia, stroke; organophosphates, lead, heavy metals, nerve agents, other toxic compounds, prions, amyloid plaque, neurotoxic viruses, stress); neurodegenerative diseases (e.g., Alzheimer's disease, Parkinson's disease, amyotrophic lateral sclerosis, multiple sclerosis, frontotemporal dementia, Huntington's disease, adrenal leukodystrophy, Alexander's disease, Alper's disease, Alzheimer's disease, amyotrophic lateral sclerosis, balo concentric sclerosis, Canavan disease, Charcot-Marie-Tooth disease, childhood ataxia with central nervous system hypomyelination, chronic idiopathic peripheral neuropathy, frontotemporal dementia, Huntington's disease, Krabbe disease, monomelic amyotrophy, multiple sclerosis (MS), neurodegeneration, neuromyelitis optica, neuropathic pain, neurosarcoidosis, Parkinson's disease, Pelizaeus-Merzbacher disease, primary lateral sclerosis, progressive supranuclear palsy, radicular pain, radiculopathic pain, Schilder's disease, sciatic pain, sciatica, subacute necrotizing myelopathy, transverse myelitis, or Zellweger syndrome); congenital or organic cognitive impairment, learning disabilities, autism spectrum disorder; cognitive enhancement, intelligence enhancement, creativity enhancement, memory improvement, learning enhancement and improvement, spiritual enhancement, "mind expansion," IQ improvement, EQ improvement, balance enhancement, athleticism, motor skill enhancement, special navigation, clairvoyance, psychic enhancement, or general improvement of mental health.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising one or more tryptamines or in pure form or pharmaceutically acceptable salts, hydrates, solvates, prodrugs, stereoisomers, or tautomers thereof, or extracts or isolates from psilocybin containing mushrooms, or combinations thereof combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof and one or more pharmaceutically acceptable excipients. In one aspect, the composition further comprises one or more adversive compounds comprising niacin, ipecac, apomorphine, bittering agents (e.g., denatonium benzoate), capsaicin, capsacutin dihydrocapsaicin, nordihydrocapsaicin, homocapsaicin, homodihydrocapsaicin, capsaicinoids, gingerol, piperine, isopiperine, zingerone, shogaol, vanillylamide derivatives, or combinations thereof.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising one or more tryptamines or in pure form or pharmaceutically acceptable salts, hydrates, solvates, prodrugs, stereoisomers, tautomers thereof or combinations thereof, or extracts or isolates from psilocybin containing mushrooms, or combinations thereof combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof; one or more cannabinoids in pure form or pharmaceutically acceptable salts, hydrates, solvates, prodrugs, stereoisomers, tautomers thereof, or combinations thereof, or extracts or isolates from *Cannabis sativa, Cannabis sativa, Cannabis indica*, or *Cannabis ruderalis*; and one or more pharmaceutically acceptable excipients.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising norpsilocin, norbaeocystin, baeocystin, or psilocybin, combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof and one or more pharmaceutically acceptable excipients.

Another embodiment described herein is the use of a pharmaceutical composition comprising one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients, in the manufacture of a medicament for treatment of serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment described herein is the use of a pharmaceutical composition comprising an effective amount of one or more tryptamines or pharmaceutically acceptable salts, hydrates, solvates, prodrugs, stereoisomers, or tautomers thereof, or combinations thereof and one or more pharmaceutically acceptable excipients, in the manufacture of a medicament for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment described herein is the use of a pharmaceutical composition comprising an effective amount of one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients in the manufacture of a medicament for treating serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment described herein is the use of a pharmaceutical composition comprising an effective amount of one or more tryptamines, erinacines, hericenones, cannabinoids, or pharmaceutically acceptable salts, hydrates, solvates, prodrugs, stereoisomers, or tautomers thereof, or combinations thereof and one or more pharmaceutically acceptable excipients for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment described herein is a means for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof in in a subject in need thereof comprising administering a composition comprising an effective amount of one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients to the subject.

Another embodiment described herein is a means for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof in in a subject in need thereof comprising administering a composition comprising an effective amount of one or more tryptamines, erinacines, hericenones, cannabinoids, or pharmaceutically acceptable salts, hydrates, solvates, prodrugs, stereoisomers, or tautomers thereof, or combinations thereof and one or more pharmaceutically acceptable excipients to the subject.

Another embodiment described herein is a method for inducing neurite growth and neurite lengthening comprising administering an effective an effective amount of one or more tryptamines or in pure form or extracts or isolates from psilocybin containing mushrooms, or combinations thereof combined with one or more erinacines or hericenones in pure form, extracts or isolates from Hericium mushroom species, or combinations thereof and one or more pharmaceutically acceptable excipients to the subject.

Another embodiment described herein is a method for inducing neurite growth and neurite lengthening comprising administering an effective an effective amount of one or more or norpsilocin, norbaeocystin, baeocystin, or psilocybin combined with one or more erinacines or hericenones in pure form, extracts or isolates from Hericium mushroom species, or combinations thereof and one or more pharmaceutically acceptable excipients to the subject.

Another embodiment described herein is a process for producing a composition comprising norpsilocin in pure form or extracts or isolates from psilocybin containing mushrooms, or combinations thereof combined with one or more erinacines or hericenones in pure form, extracts or isolates from Hericium mushroom species, or combinations thereof, comprising: growing a mushroom on a substrate; separating mushroom mycelium from a fruitbody and the substrate; extracting the mushroom mycelium in a solvent, forming a solution; and lyophilizing the extract. In one aspect, the substrate comprises one or more of rice, oat, straw, or sawdust. In another aspect, the solvent is ethanol.

Another embodiment described herein is a composition comprising one or more tryptamines or in pure form or extracts or isolates from psilocybin containing mushrooms, or combinations thereof combined with one or more erinacines or hericenones in pure form, extracts or isolates from Hericium mushroom species, or combinations thereof. In one aspect, the tryptamine comprises, one or more of psilocybin, baeocystin, norbaeocystin, psilocin, norpsilocin, aeruginascin, 4-hydroxytryptamine, N,N-dimethyltryptamine, or N-methyltryptamine; other tryptamines, or pharmaceutically acceptable salts, hydrates, solvates, prodrugs, stereoisomers, or tautomers thereof. In another aspect, the erinacines or hericenones comprise Erinacine A, Erinacine B, Erinacine C, Erinacine D, Erinacine E, Erinacine F, Erinacine G, Erinacine H, Erinacine I, Erinacine J, Erinacine K, Erinacine P, Erinacine Q, Erinacine R, Erinacol, other Erinacines Hericenone A, Hericenone B, Hericenone C, Hericenone D, Hericenone E, Hericenone F, Hericenone G, Hericenone H, other hericenones, or pharmaceutically acceptable salts, hydrates, solvates, prodrugs, stereoisomers, or tautomers thereof. In another aspect, the composition further comprises one or more cannabinoids in pure form or extracts or isolates from *Cannabis sativa, Cannabis sativa, Cannabis indica*, or *Cannabis ruderalis*. In another aspect, the cannabinoids comprise one or more of Δ8-tetrahydrocannabinol (THC), Δ9-tetrahydrocannabinol, tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), among others, or pharmaceutically acceptable salts, hydrates, solvates, prodrugs, stereoisomers, or tautomers thereof. In another aspect, the composition further comprises one or more phenethylamines or amphetamines in pure form or extracts or isolates from plants comprising thereof. In another aspect, the phenethylamines or amphetamines comprises 3,4,5-trimethoxyphenethylamine (Mescaline), 2,5-dimethoxy-4-methylamphetamine (DOM), 2,5-dimethoxy-4-bromophenethylamine (2C-B), 2,5-dimethoxy-4-ethylphenethylamine (2C-E), 2,5-dimethoxy-4-ethylthiophenethylamine (2C-T-2), 2,5-dimethoxy-4-propylthiophenethylamine (2C-T-7), p-methoxyamphetamine (PMA), 2,4-dimethoxyamphetamine (2,4-DMA), 3,4-dimethoxy-amphetamine (3,4-DMA), 3,4-methylenedioxy-amphetamine (MDA), 3-methoxy-4,5-methylendioxy-amphetamine (MMDA), 2-methoxy-3,4-methylendioxyamphetamine (MMDA-3a), 2-methoxy-4,5-methylendioxyamphetamine (MMDA-2), 3,4,5-trimethoxyamphetamine (TMA), 2,4,5-trimethoxyamphetamine (TMA-2), 2,5-dimethoxy-3,4-methylenedioxyamphetamine (DMMDA), 2,3-dimethoxy-4,5-methylenedioxyamphetamine (DMMDA-2), 2,3,4,5-tetramethoxyamphetamine (TeMA), inter alia, pharmaceutically acceptable salts, hydrates, solvates, prodrugs, stereoisomers, or tautomers thereof. In another aspect, the composition further comprises one or more adversive compounds comprising niacin, ipecac, apomorphine, bittering agents (e.g., denatonium benzoate), capsaicin, capsacutin dihydrocapsaicin, nordihydrocapsaicin, homocapsaicin, homodihydrocapsaicin, capsaicinoids, gingerol, piperine, isopiperine, zingerone, shogaol, vanillylamide derivatives, or combinations thereof. In another aspect, the composition comprises 0.001 mg to 0.01 mg, 0.01 mg to 0.1 mg, 0.01 mg to 1 mg, 0.1 mg to 5 mg, 0.1 mg to 1 mg, 0.5 mg to 1 mg, 0.5 mg to 5 mg, 0.25 mg to 1 mg, 0.2 mg to 2 mg, or 0.2 mg to 5 mg of one or more tryptamines or an amount of a plant or mushroom extract or plant or mushroom to provide an equivalent dose. In another aspect, the composition comprises 1 μg to 5 μg, 1 μg to 10 μg, 5 μg to 10 μg, 10 μg to 5 mg, 10 μg to 100 μg, 100 μg to 1 mg, 500 μg to 1 mg, 500

μg to 5 mg, 1 mg to 5 mg, 100 μg to 1 mg, 100 μg to 500 μg, 100 μg to 250 μg; 250 μg to 1 mg; 750 μg to 1 mg, or 250 μg to 750 μg of one or more erinacines or hericenones or an amount of a plant or mushroom extract or plant or mushroom to provide an equivalent dose. In another aspect, the composition comprises 0.01 mg to 0.1 mg, 0.01 mg to 1 mg, 0.1 mg to 10 mg, 0.1 mg to 1 mg, 0.5 mg to 1 mg, 0.5 mg to 5 mg, 0.25 mg to 1 mg, 0.2 mg to 2 mg, 0.2 mg to 5 mg, or 1 mg to 10 mg of one or more cannabinoids or an amount of a plant extract or plant or mushroom to provide an equivalent dose. In another aspect, the composition comprises 0.1 mg to 1 mg, 1 mg to 10 mg, 10 mg to 100 mg, 10 mg to 50 mg, 50 mg to 100 mg, 20 mg to 80 mg, 20 mg to 50 mg, 50 mg to 100 mg, 50 mg to 80 mg, or 10 mg to 80 mg of one or more phenethylamines or amphetamines or an amount of a plant or mushroom extract or plant or mushroom to provide an equivalent dose. In another aspect, the composition comprises 0.1 mg to 10 mg, 1 mg to 500 mg, 1 mg to 100 mg, 200 mg to 500 mg, 50 mg to 200 mg, 10 mg to 50 mg, 50 mg to 200 mg, 1 mg to 200 mg, or 1 mg to 50 mg of one or more adversives. In another aspect, the composition comprises one or more pharmaceutically acceptable excipients. In another aspect, the composition is a powder admixture, liquid, suspension, or emulsion. In another aspect, the composition further comprises one or more extracts or pure chemicals from other fungi comprising one or more of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof; a mycelium extract of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof; or a fruitbody extract of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species or combinations thereof. In another aspect, the composition further comprises one or more extracts or pure chemicals from plant species comprising one or more of Bacopa species (Bacopa monnien), Gotu kola (Centella *asiatica*), and Gingko (Gingko *biloba*, Ginger (*Zingiber officinale*), Holy Basil (*Ocimum* sanctum), Hu Zhang (*Polygonum cuspidatum*), Oregano (*Origanum vulgare, Origanum* onites), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula* spica and related species in the genus *Lavandula*), skullcap (Scutellaria lateriflora) oat straw (*Avena sativa, Avena byzantina*), *Salvia* divinorum, aka Diviner's Sage, Banisteriopsis caapi and Psychotria species, plants containing ibogaine (Tabemanthe iboga, Voacanga *africana* and Tabemaemontana undulate), peyote (Lophophora williamsii), the seeds of morning glory (*Ipomoea tricolor* and related species) and Hawaiian baby wood rose (Argyreia nervosa), Acacia *confusa, Acacia obtusifolia, Acacia simplicifolia*, Desmanthus Illinoensis, or *Cannabis* (*Cannabis sativa, C. indica* and *C. ruderalis*), or combinations thereof. In another aspect, the composition is effective to treat, alleviate, prevent or ameliorate serotonin (5-hydroxytryptamine, 5-HT) receptor disorders, psychiatric and mood disorders, e.g., depression, anxiety, major depressive disorder, treatment resistant depression, persistent depression, manic depression or bipolar disorder, depressive psychosis, perinatal depression, premenstrual dysphoric disorder, seasonal depressions, situational depression, panic disorder, obsessive compulsive disorder, post-traumatic stress disorder, attention deficit/hyperactivity disorder, sleep disorders, eating disorders, schizophrenia, personality disorders, substance abuse disorders (drug abuse, addiction, alcoholism); neuronal injuries or physical neurodegeneration (e.g., physical injury, head trauma, spinal cord trauma, concussion, peripheral neuron trauma, paralysis, ischemia, hypoxia, stroke; organophosphates, lead, heavy metals, nerve agents, other toxic compounds, prions, amyloid plaque, neurotoxic viruses, stress); neurodegenerative diseases (e.g., Alzheimer's disease, Parkinson's disease, amyotrophic lateral sclerosis, multiple sclerosis, frontotemporal dementia, Huntington's disease, adrenal leukodystrophy, Alexander's disease, Alper's disease, Alzheimer's disease, amyotrophic lateral sclerosis, balo concentric sclerosis, Canavan disease, Charcot-Marie-Tooth disease, childhood ataxia with central nervous system hypomyelination, chronic idiopathic peripheral neuropathy, frontotemporal dementia, Huntington's disease, Krabbe disease, monomelic amyotrophy, multiple sclerosis (MS), neurodegeneration, neuromyelitis optica, neuropathic pain, neurosarcoidosis, Parkinson's disease, Pelizaeus-Merzbacher disease, primary lateral sclerosis, progressive supranuclear palsy, radicular pain, radiculopathic pain, Schilder's disease, sciatic pain, sciatica, subacute necrotizing myelopathy, transverse myelitis, or Zellweger syndrome); congenital or organic cognitive impairment, learning disabilities, autism spectrum disorder; cognitive enhancement, intelligence enhancement, creativity enhancement, memory improvement, learning enhancement and improvement, spiritual enhancement, "mind expansion," IQ improvement, EQ improvement, balance enhancement, athleticism, motor skill enhancement, special navigation, clairvoyance, psychic enhancement, or general improvement of mental health. In another aspect, the composition comprises norpsilocin and an extract of extracts or isolates rom Hericium *erinaceus. In another aspect, the composition comprises baeocystin and an extract of extracts or isolates rom Hericium erinaceus*. In another aspect, the composition comprises norbaeocystin and an extract of extracts or isolates rom Hericium *erinaceus*.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising one or more tryptamines or in pure form or pharmaceutically acceptable salts, hydrates, solvates, prodrugs, stereoisomers, or tautomers thereof, or extracts or isolates from psilocybin containing mushrooms, or combinations thereof combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof and one or more pharmaceutically acceptable excipients. In one aspect, the composition further comprises one or more adversive compounds comprising niacin, ipecac, apomorphine, bittering agents (e.g., denatonium benzoate), capsaicin, capsacutin dihydrocapsaicin, nordihydrocapsaicin, homocapsaicin, homodihydrocapsaicin, capsaicinoids, gingerol, piperine, isopiperine, zingerone, shogaol, vanillylamide derivatives, or combinations thereof.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising one or more tryptamines or in pure form or pharmaceutically acceptable salts, hydrates, solvates, prodrugs, stereoisomers, tautomers thereof or combinations thereof, or extracts or isolates from psilocybin containing mushrooms, or combinations thereof combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof; one or more cannabinoids in pure form or pharmaceutically acceptable salts, hydrates, solvates, prodrugs, stereoisomers, tautomers thereof, or combinations thereof, or extracts or isolates from *Cannabis sativa, Cannabis sativa, Cannabis indica*, or *Cannabis ruderalis*; and one or more pharmaceutically acceptable excipients.

Another embodiment described herein is a method of treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a composition comprising norpsilocin, norbaeocystin, baeocystin, or psilocybin, combined with one or more erinacines or hericenones in pure form or pharmaceutically acceptable salts, hydrates, solvates, prodrugs, stereoisomers, or tautomer thereof, or combinations thereof, extracts or isolates from Hericium mushroom species, combinations thereof and one or more pharmaceutically acceptable excipients.

Another embodiment described herein is the use of a pharmaceutical composition comprising one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients, in the manufacture of a medicament for treatment of serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment described herein is the use of a pharmaceutical composition comprising an effective amount of one or more tryptamines or pharmaceutically acceptable salts, hydrates, solvates, prodrugs, stereoisomers, or tautomers thereof, or combinations thereof and one or more pharmaceutically acceptable excipients, in the manufacture of a medicament for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment described herein is the use of a pharmaceutical composition comprising an effective amount of one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients in the manufacture of a medicament for treating serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment described herein is the use of a pharmaceutical composition comprising an effective amount of one or more tryptamines, erinacines, hericenones, cannabinoids, or pharmaceutically acceptable salts, hydrates, solvates, prodrugs, stereoisomers, or tautomers thereof, or combinations thereof and one or more pharmaceutically acceptable excipients for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment described herein is a means for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof in in a subject in need thereof comprising administering a composition comprising an effective amount of one or more tryptamines, erinacines, hericenones, or pharmaceutically acceptable salts, hydrates, solvates, prodrugs, stereoisomers, or tautomers thereof, or combinations thereof and one or more pharmaceutically acceptable excipients to the subject.

Another embodiment described herein is a means for treating or preventing serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof in in a subject in need thereof comprising administering a composition comprising an effective amount of one or more tryptamines, erinacines, hericenones, cannabinoids, or pharmaceutically acceptable salts, hydrates, solvates, prodrugs, stereoisomers, or tautomers thereof, or combinations thereof and one or more pharmaceutically acceptable excipients to the subject.

Another embodiment described herein is a method for inducing neuronal growth and neuronal lengthening comprising administering an effective an effective amount of one or more tryptamines or in pure form or extracts or isolates from psilocybin containing mushrooms, or combinations thereof combined with one or more erinacines or hericenones in pure form, extracts or isolates from Hericium mushroom species, or combinations thereof and one or more pharmaceutically acceptable excipients to the subject.

Another embodiment described herein is a method for inducing neuronal growth and neuronal lengthening comprising administering an effective an effective amount of one or more or norpsilocin, norbaeocystin, baeocystin, or psilocybin combined with one or more erinacines or hericenones in pure form, extracts or isolates from Hericium mushroom species, or combinations thereof and one or more pharmaceutically acceptable excipients to the subject.

BRIEF DESCRIPTION OF THE DRAWINGS

FIG. 6 shows the plate layout for Neurite Outgrowth 5.

DETAILED DESCRIPTION

Figure 1:
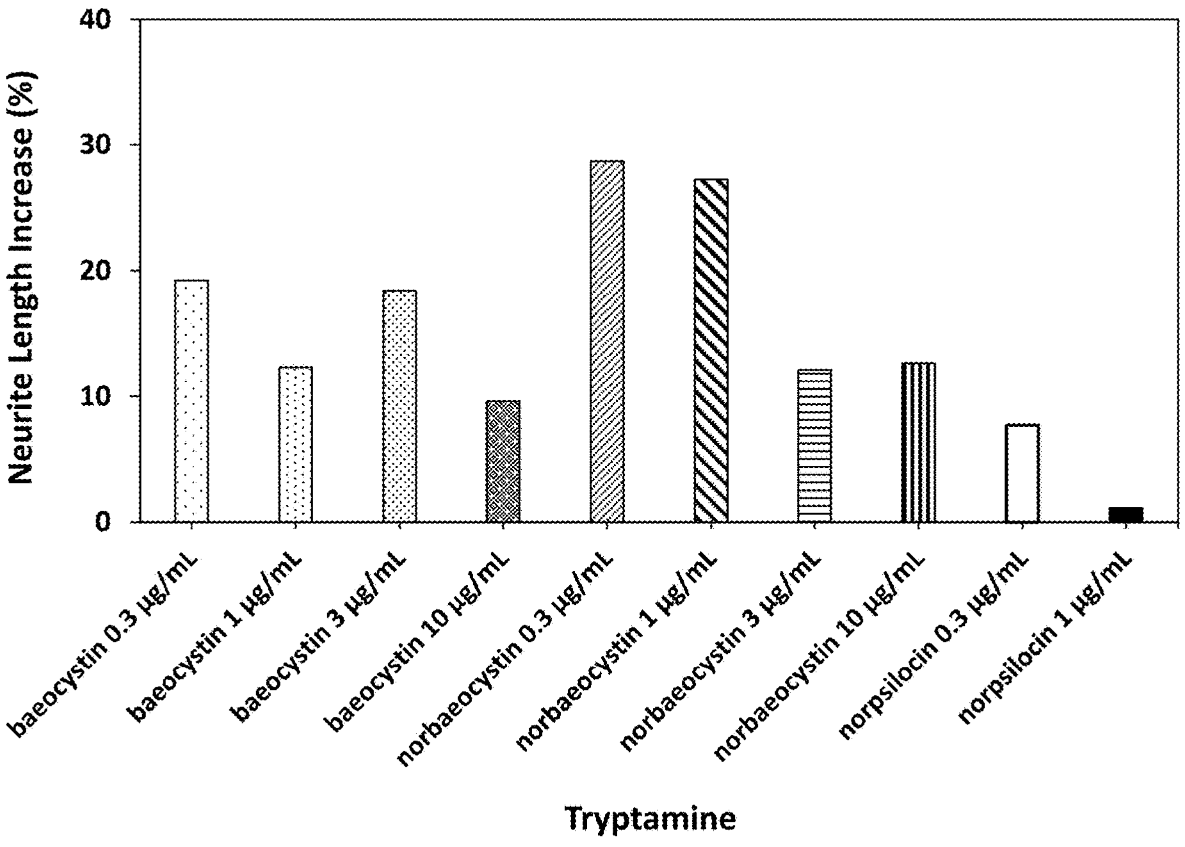
FIG. 1 shows the effect of four concentrations of the tryptamines baeocystin, norbaeocystin, and norpsilocin on neurite growth relative to the vehicle control. The norpsilocin 3 and 10 μg/mL experiments are not shown. Data is shown in Table 6.

Described herein are neurotrophic and nootropic compositions and methods for treating subjects with such compositions.

As used herein, the term "tryptamine" refers to any compound related to or derived from the monoamine alkaloid 2-(1 H-Indol-3-yl)ethanamine (tryptamine), a non-selective $5\text{-}HT_{2A}$ agonist and serotonin-norepinephrine-dopamine releasing agent (SNDRA). The tryptamine may be a natural product extracted from or isolated from a natural source, such as a Psilocybe mushroom, or synthesized synthetically. Exemplary tryptamines include psilocybin, baeocystin, norbaeocystin, psilocin, norpsilocin, 4-hydroxytryptamine, N,N-dimethyltryptamine, 5-hydroxytryptamine (serotonin), tryptamine, N-methyltryptamine, N-methyltryptamine, inter alia, pharmaceutically acceptable salts, hydrates, solvates, prodrugs, stereoisomers, or tautomers thereof. Tryptamines such as psilocybin, psilocin, and baeocystin when in mushrooms from nature are known to decay over time, especially quickly in suboptimal storage conditions. Repke et al., *J. Pharmac. Sci.* 66(1): 113-114 (1977). In another study, psilocybin content of *P. cubensis* ranged from 0.102% to 0.706%, while psilocin content ranged from 0.415% to 0.836% of dried mushroom tissue. Gambaro et al., *J. Pharmac. Biomed. Anal.* 125: 427-432 (2016). This variability is consistent with trends previously observed, where psilocybin content of mushroom tissue appeared to increase with subsequent flushes. Bigwood and Beug, *J. Ethnopharmacology* 5(3): 287-291 (1982); Beug amd Bigwood, *J. Ethnopharmacology* 5(3): 271-285 (1982). The growing substrate can affect the tryptamine concentration as well. Gartz found that growing Psilocybe *cubensis* on a cow dung-rice growing substrate increased psilocin content in Psilocybe *cubensis* from 0.09% to 3.3% of the dried mushroom weight. See Gartz, *Planta Med.* 55(3): 249-250 (1989). Also, different parts of a mushroom can have different quantities of these compounds. For example, one study found that psilocybin is highest in the caps of Panaeolus subalteatus as compared to the rest of the fruiting body. See Gartz, *Biochemie und Physiologie der Pflanzen.* 184(1-2): 171-178 (1989). In addition to psilocybin and psilocin, several other tryptamine alkaloid compounds can also be present in varying concentrations in mushrooms found in nature.

Generally, these compounds are part of the same biosynthetic pathway that yields psilocybin and can be distinguished from one another based on the presence or absence of one or more methyl or phosphate groups. This unique class of biochemicals is referred to as psilocybin analogs. Few reports of baeocystin consumption exist. In a 1997 book, Jochen Gartz reported that baeocystin was roughly akin to psilocybin in terms of its potency and psychotropic effects. The same author had previously published an anecdotal experience where he experienced a "gentle hallucinogenic experience" after consuming 4 mg of baeocystin. See Gartz, *Ann Mus civ Rovereto* 7: 265-74 (1991). Additional case studies of oral consumption of 10 mg and 20 mg baeocystin did not produce any hallucinogenic effects. Even less is understood about norpsilocin, baeocystin's dephosphorylated derivative, which was only recently identified. Lenz et al., *J. Nat. Prod.* 80(10): 2835-2838 (2017).

As used herein, the terms "phenethylamine" and "amphetamine" refers to any compound related to or derived from the monoamine alkaloids, which acts as a central nervous system stimulant. The phenethylamines and amphetamines may be natural products extracted from or isolated from natural sources or synthetically synthesized. Exemplary phenethylamines and amphetamines include 3,4,5-trimethoxyphenethylamine (Mescaline), 2,5-dimethoxy-4-methylamphetamine (DOM), 2,5-dimethoxy-4-bromophenethylamine (2C-B), 2,5-dimethoxy-4-ethylphenethylamine (2C-E), 2,5-dimethoxy-4-ethylthiophenethylamine (2C-T-2), 2,5-dimethoxy-4-propylthiophenethylamine (2C-T-7), p-methoxy-amphetamine (PMA), 2,4-dimethoxy-amphetamine (2,4-DMA), 3,4-dimethoxy-amphetamine (3,4-DMA), 3,4-methylenedioxy-amphetamine (MDA), 3-methoxy-4,5-methylendioxy-amphetamine (MMDA), 2-methoxy-3,4-methylendioxyamphetamine (MMDA-3a), 2-methoxy-4,5-methylendioxyamphetamine (MMDA-2), 3,4,5-trimethoxyamphetamine (TMA), 2,4,5-trimethoxyamphetamine (TMA-2), 2,5-dimethoxy-3,4-methylenedioxyamphetamine (DMMDA), 2,3-dimethoxy-4,5-methylenedioxyamphetamine (DMMDA-2), 2,3,4,5-tetramethoxyamphetamine (TeMA), (R)-2,5-dimethoxy-4-iodoamphetamine, inter alia, pharmaceutically acceptable salts, hydrates, solvates, prodrugs, stereoisomers, or tautomers thereof.

As used herein, the terms "erinacines" and "hericenones" refer to the cyathin diterpenoids erinacine, hericenone, and related compounds. The compounds may be synthetic or natural products isolated from or extracted from H. *erinaceus, H. coralloides, H. ramosum*. Exemplary compounds include Erinacine A, Erinacine B, Erinacine C, Erinacine D, Erinacine E, Erinacine F, Erinacine G, Erinacine H, Erinacine I, Erinacine J, Erinacine K, Erinacine P, Erinacine Q, Erinacine R, Erinacol, other Erinacines Hericenone A, Hericenone B, Hericenone C, Hericenone D, Hericenone E, Hericenone F, Hericenone G, Hericenone H, other hericenones, or pharmaceutically acceptable salts, hydrates, solvates, prodrugs, stereoisomers, or tautomers thereof. In contrast to psilocybin mushrooms which primarily grow on the ground in meadows and woods of the subtropics and tropics, usually in soils rich in humus and plant debris, Hericium *erinaceus* (Lion's Mane mushrooms) grow on the bark of trees in temperate forests of the Northern United States and Canada, where they are able to withstand cold temperatures and frost. Further, psilocybin mushrooms are terrestrial, whereas Lion's Mane mushrooms are non-terrestrial (i.e., they grow on trees). Therefore, Lion's Mane mushrooms and psilocybin mushrooms live in different habitats and neither is found cohabitating or combined in nature.

As used herein, the term "cannabinoids" refer to the phytocannabinoids from *Cannabis. The compounds may be synthetic or natural products isolated from or extracted from Cannabis sativa, Cannabis sativa, Cannabis indica*, or *Cannabis ruderalis*. Exemplary compounds include Δ8-tetrahydrocannabinol, Δ9-tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), among others, or pharmaceutically acceptable salts, hydrates, solvates, prodrugs, stereoisomers, or tautomers thereof.

The term "a therapeutically effective amount" of a compound described herein refers to an amount of the compound described herein that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound described herein that, when administered to a subject, is effective to at least partially alleviate, prevent and/or ameliorate a condition, or a disorder or serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health. In one embodiment, the term "a therapeutically effective amount" refers to the amount of the compound described herein that, when administered to a cell, or a tissue, or a non-cellular biological material, or a medium, is effective to treat or ameliorate serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

As used herein, the term "subject" refers to an animal. Typically, the animal is a mammal. A subject also refers to, for example, primates (e.g., humans, male or female; infant, adolescent, or adult), cows, sheep, goats, horses, dogs, cats, rabbits, rats, mice, fish, birds, and the like. In an embodiment, the subject is a primate. In one embodiment, the subject is a human.

As used herein, the terms "inhibit," "inhibition," or "inhibiting" refer to the reduction or suppression of a given condition, symptom, or disorder, or disease, or a significant decrease in the baseline activity of a biological activity or process.

As used herein, the terms "treat", "treating," or "treatment" of any disease or disorder refer In an embodiment, to ameliorating the disease or disorder (i.e., slowing or arresting or reducing the development of the disease or at least one of the clinical symptoms thereof). In an embodiment, "treat," "treating," or "treatment" refers to alleviating or ameliorating at least one physical or mental parameter including those which may not be discernible by the subject.

As used herein, the term "preventing" refers to a reduction in the frequency of, or delay in the onset of, symptoms of the condition or disease.

As used herein, a subject is "in need of" a treatment if such subject would benefit biologically, medically, or in quality of life from such treatment.

As used herein, "serotonin (5-hydroxytryptamine, 5-HT) receptor disorders" refers to any disorder or disease that affects serotonin receptors including neuronal injuries, organic abnormalities, depression, mood disorders, and the like. Serotonin receptors modulate the release of neurotransmitters such as glutamate, GABA, dopamine, epinephrine, norepinephrine, and acetylcholine, and hormones, including oxytocin, prolactin, vasopressin, cortisol, corticotropin, substance P, inter alia. Specifically, $5\text{-HT}_{2A/C}$ receptors influence various biological and neurological processes such as addiction, anxiety, appetite, locomotion, cognition, imagination, learning, memory, mood, perception, sexual behavior, sleep, thermoregulation, and vasoconstriction. In addition, $5\text{-HT}_{2C}$ is a heteroreceptor for norepinephrine and dopamine.

As used herein, "mental health" refers to a subject's emotional, psychological, and social well-being. Mental health disorders or problems refer to disorders affecting cognition, mood, behavior, and homeostasis. Mental health disorders may be caused by biological factors (genetic or neurochemistry), stress, trauma, or abuse, or associated with injury.

The term "alkyl" refers to a radical of a straight chain or branched saturated hydrocarbon group having from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl).

"Alkylene" refers to a divalent radical of an alkyl group, e.g., $—CH_2—$, $—CH_2CH_2—$, and $—CH_2CH_2CH_2—$.

"Heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and one or more heteroatoms within the parent chain ("hetero$C_{1-8}$alkyl"). In some embodiments, a heteroalkyl group is a saturated group having 1 to 7 carbon atoms and one or more heteroatoms within the parent chain ("hetero$C_{1-7}$alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("heteroC1 alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Heteroalkylene" refers to a divalent radical of a heteroalkyl group.

"Alkoxy" or "alkoxyl" refers to an —O-alkyl radical. In some embodiments, the alkoxy groups are methoxy, ethoxy, n-propoxy, isopropoxy, n-butoxy, tert-butoxy, sec-butoxy, n-pentoxy, n-hexoxy, and 1,2-dimethylbutoxy. In some embodiments, alkoxy groups are lower alkoxy, i.e., with between 1 and 6 carbon atoms. In some embodiments, alkoxy groups have between 1 and 4 carbon atoms.

As used herein, the term "aryl" refers to a stable, aromatic, mono- or bicyclic ring radical having the specified number of ring carbon atoms. Examples of aryl groups include, but are not limited to, phenyl, 1-naphthyl, 2-naphthyl, and the like. The related term "aryl ring" likewise refers to a stable, aromatic, mono- or bicyclic ring having the specified number of ring carbon atoms.

As used herein, the term "heteroaryl" refers to a stable, aromatic, mono- or bicyclic ring radical having the specified number of ring atoms and comprising one or more heteroatoms individually selected from nitrogen, oxygen, and sulfur. The heteroaryl radical may be bonded via a carbon atom or heteroatom. Examples of heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl, pyridyl, quinolinyl, isoquinolinyl, indolyl, indazolyl, oxadiazolyl, benzothiazolyl, quinoxalinyl, and the like. The related term "heteroaryl ring" likewise refers to a stable, aromatic, mono- or bicyclic ring having the specified number of ring atoms and comprising one or more heteroatoms individually selected from nitrogen, oxygen, and sulfur.

As used herein, the term "carbocycle" refers to a stable, saturated, or unsaturated, non-aromatic, mono- or bicyclic (fused, bridged, or spiro) ring radical having the specified number of ring carbon atoms. Examples of carbocycle groups include, but are not limited to, the cycloalkyl groups identified above, cyclobutenyl, cyclopentenyl, cyclohexenyl, and the like. In an embodiment, the specified number is $C_3$-$C_{12}$ carbons. The related term "carbocyclic ring" likewise refers to a stable, saturated, or unsaturated, non-aromatic, mono- or bicyclic (fused, bridged, or spiro) ring having the specified number of ring carbon atoms.

As used herein, the term "heterocyclyl" refers to a stable, saturated or unsaturated, non-aromatic, mono- or bicyclic (fused, bridged, or spiro) ring radical having the specified number of ring atoms and comprising one or more heteroatoms individually selected from nitrogen, oxygen and sulfur. The heterocyclyl radical may be bonded via a carbon atom or heteroatom. In an embodiment, the specified number is $C_3$-$C_{12}$ carbons. Examples of heterocyclyl groups include, but are not limited to, azetidinyl, oxetanyl, pyrrolinyl, pyrrolidinyl, tetrahydrofuryl, tetrahydrothienyl, piperidyl, piperazinyl, tetrahydropyranyl, morpholinyl, perhydroazepinyl, tetrahydropyridinyl, tetrahydroazepinyl, octahydropyrrolopyrrolyl, and the like. The related term "heterocyclic ring" likewise refers to a stable, saturated or unsaturated, non-aromatic, mono- or bicyclic (fused, bridged, or spiro) ring having the specified number of ring atoms and comprising one or more heteroatoms individually selected from nitrogen, oxygen and sulfur.

As used herein, "spirocycloalkyl" or "spirocycle" means carbogenic bicyclic ring systems with both rings connected through a single atom. The rings can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. For example, a $(C_3-C_2)$spirocycloalkyl is a spirocycle containing between 3 and 12 carbon atoms.

As used herein, "spiroheterocycloalkyl" or "spiroheterocycle" means a spirocycle wherein at least one of the rings is a heterocycle wherein one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

As used herein, "halo" or "halogen" refers to fluorine (fluoro, —F), chlorine (chloro, —Cl), bromine (bromo, —Br), or iodine (iodo, –I).

As used herein, "haloalkyl" means an alkyl group substituted with one or more halogens. Examples of haloalkyl groups include, but are not limited to, trifluoromethyl, difluoromethyl, pentafluoroethyl, and trichloromethyl.

As used herein, "substituted," whether preceded by the term "optionally" or not, means that one or more hydrogens of the designated moiety are replaced with a suitable substituent.

As used herein, the definition of each expression, e.g., alkyl, m, n, etc., when it occurs more than once in any structure, is intended to be independent of its definition elsewhere in the same structure.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to mass (or weight, w/w) percent unless noted otherwise.

The term "about" as used herein refers to any values, including both integers and fractional components that are within a variation of up to ±10% of the value modified by the term "about." As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

Terms such as "include," "including," "contain," "containing," "having," and the like mean "comprising."

The term "or" can be conjunctive or disjunctive.

Definitions of specific functional groups and chemical terms are described in more detail herein. The chemical elements are identified in accordance with the Periodic Table of the Elements, CAS version, *Handbook of Chemistry and Physics,* $75^{th}$ ed., inside cover, and specific functional groups are generally defined as described therein. Additionally, general principles of organic chemistry, as well as specific functional moieties and reactivity, are described in Thomas Sorrell, *Organic Chemistry, University Science Books, Sausalito,* 1999; Smith and March, *March's Advanced Organic Chemistry,* $5^{th}$, John Wiley & Sons, Inc., New York, 2001; Larock, *Comprehensive Organic Transformations*, VCH Publishers, Inc., New York, 1989; and *Carruthers, Some Modern Methods of Organic Synthesis,* $3^{rd}$ ed, Cambridge University Press, Cambridge, 1987.

Certain compounds described herein may exist in particular geometric or stereoisomeric forms. A particular enantiomer of a compound described herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise stated, structures depicted herein are also meant to include geometric (or conformational) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the disclosed compounds are within the scope of the disclosure. Unless otherwise stated, all tautomeric forms of the compounds described herein are within the scope of the disclosure. Additionally, unless otherwise stated, structures depicted herein are also meant to include compounds that differ only in the presence of one or more isotopically enriched atoms. For example, compounds having the disclosed structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the disclosure.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer. ee=(90-10)/100×100=80%.

Thus, a composition containing 90% of one enantiomer and 10% of the other enantiomer is said to have an enantiomeric excess of 80%. The compounds or compositions described herein may contain an enantiomeric excess of at least 50%, 75%, 90%, 95%, or 99% of one form of the compound, e.g., the S-enantiomer. In other words, such compounds or compositions contain an enantiomeric excess of the S enantiomer over the R enantiomer.

Where a particular enantiomer is preferred, it may, in some embodiments be provided substantially free of the corresponding enantiomer and may also be referred to as "optically enriched." "Optically enriched," as used herein, means that the compound is made up of a significantly greater proportion of one enantiomer. In certain embodiments, the compound is made up of at least about 90% by weight of a preferred enantiomer. In other embodiments, the compound is made up of at least about 95%, 98%, or 99% by weight of a preferred enantiomer.

Preferred enantiomers may be isolated from racemic mixtures by any method known to those skilled in the art, including chiral high-pressure liquid chromatography (HPLC) and the formation and crystallization of chiral salts or prepared by asymmetric syntheses. See e.g., Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw Hill, NY, 1962); Wilen, S. H. *Tables of Resolving Agents and Optical Resolutions* p. 268 (E. L. Eliel, Ed., Univ. of Notre Dame Press, Notre Dame, IN 1972).

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

Any resulting mixtures of isomers can be separated based on the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds described herein into their optical antipodes, e.g., by fractional crystallization of a salt formed with an optically active acid, e.g., tartaric acid, dibenzoyl tartaric acid, diacetyl tartaric acid, di-O,O-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Various exemplary embodiments of the disclosure are described herein. It will be recognized that features specified in each embodiment may be combined, substituted, or replaced with other specified features disclosed elsewhere in the specification to provide further embodiments of the present disclosure. All analagous compounds may be substituted for each other in the same or similar amounts (mass, concentration, or dosages) as indicated for analagous compounds.

It is understood that in the following embodiments, combinations of substituents or variables of the depicted formulae are permissible only if such combinations result in stable compounds.

Pharmaceutically Acceptable Salts

Pharmaceutically acceptable salts of the compounds described herein are also contemplated for the uses described herein. As used herein, the terms "salt" or "salts" refer to an acid addition or base addition salt of a compound described herein. "Salts" include in particular "pharmaceutical acceptable salts." The term "pharmaceutically acceptable salts" refers to salts that retain the biological effectiveness and properties of the compounds disclosed herein and, which typically are not biologically or otherwise undesirable. In many cases, the compounds disclosed herein can form acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, and tromethamine.

Another embodiment is a tryptamine, phenethylamine, amphetamine, erinacine, hericenone, or cannabinoid as an acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate, or xinafoate salt form.

Pharmaceutical Compositions

Another embodiment is a pharmaceutical composition comprising one or more compounds described herein or a pharmaceutically acceptable salt, hydrate, solvate, prodrug, stereoisomer, or tautomer thereof, and one or more pharmaceutically acceptable carrier(s). The term "pharmaceutically acceptable carrier" refers to a pharmaceutically acceptable material, composition, or vehicle, such as a liquid or solid filler, diluent, excipient, solvent, or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally, or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween®, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions described herein may be orally administered in any orally acceptable dosage form including, but not limited to, capsules, tablets, aqueous suspensions, or solutions. In the case of tablets for oral use, carriers commonly used include lactose and com starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be administered using a rectal suppository formulation (see above) or a suitable enema formulation. Topically transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutically acceptable compositions of this disclosure may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons, or other conventional solubilizing or dispersing agents. The amount of the compounds of the present disclosure that may be combined with the carrier materials to produce a composition in a single dosage form will vary depending upon the host treated and the mode of administration. Preferably, the compositions should be formulated so that a dosage of between 0.01-100 mg/kg body weight/day of the inhibitor can be administered to a patient receiving these compositions.

Isotopically Labelled Compounds

A compound described herein or a pharmaceutically acceptable salt, hydrate, solvate, prodrug, stereoisomer, or tautomer thereof, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds described herein include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{123}$, $^{124}I$, $^{125}I$, respectively. The disclosure includes various isotopically labeled compounds as defined herein, for example, those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. An $^{18}F$ or labeled compound may be particularly desirable for PET or SPECT studies. Isotopically-labeled compounds described herein or a pharmaceutically acceptable salt, hydrate, solvate, prodrug, stereoisomer, or tautomer thereof, can generally be prepared by conventional techniques known to those skilled in the art or by processes analogous to those described herein using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example, increased in vivo half-life or reduced dosage requirements or an improvement in therapeutic index. It is understood that deuterium in this context is regarded as a substituent of a compound described herein or a pharmaceutically acceptable salt, hydrate, solvate, prodrug, stereoisomer, or tautomer thereof. The concentration of such a heavier isotope, specifically deuterium, may be defined by the isotopic enrichment factor. The term "isotopic enrichment factor" as used herein means the ratio between the isotopic abundance and the natural abundance of a specified isotope.

Dosages

Toxicity and therapeutic efficacy of compounds described herein, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and thereby reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Methods of Use

Another embodiment is a method of treating or preventing neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof, the method comprising administering to the subject a therapeutically effective amount of a compound disclosed herein, or a pharmaceutically acceptable salt, hydrate, solvate, prodrug, stereoisomer, or tautomer thereof.

Another embodiment is a composition comprising a tryptamine, an erinacine, a hericenone, a cannabinoid, or a pharmaceutically acceptable salt, hydrate, solvate, prodrug, stereoisomer, or tautomer thereof, or a combination thereof, and a pharmaceutically acceptable carrier, for use in treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment is a composition comprising a tryptamine, an erinacine, a hericenone, a cannabinoid, or a pharmaceutically acceptable salt, hydrate, solvate, prodrug, stereoisomer, or tautomer thereof, or a combination thereof, and a pharmaceutically acceptable carrier, for use in treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment is a pharmaceutical composition comprising a tryptamine, an erinacine, a hericenone, a cannabinoid, or a pharmaceutically acceptable salt, hydrate, solvate, prodrug, stereoisomer, or tautomer thereof, or a combination thereof, and a pharmaceutically acceptable carrier, for use in treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment is a composition comprising a tryptamine, an erinacine, a hericenone, a cannabinoid, or a pharmaceutically acceptable salt, hydrate, solvate, prodrug, stereoisomer, or tautomer thereof, or a combination thereof, for use in treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof. In another embodiment, the composition is useful for treating or preventing a neurological disorder, a respiratory disorder, a proliferative disorder, an autoimmune disorder, an autoinflammatory disorder, an inflammatory disorder, or an infectious disease or disorder.

Another embodiment is the use of a composition comprising a tryptamine, an erinacine, a hericenone, a cannabinoid, or a pharmaceutically acceptable salt, hydrate, solvate, prodrug, stereoisomer, or tautomer thereof, or a combination thereof, in the manufacture of a medicament for treatment of neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment is the use of a pharmaceutical composition comprising a tryptamine, an erinacine, a hericenone, a cannabinoid, or a pharmaceutically acceptable salt, hydrate, solvate, prodrug, stereoisomer, or tautomer thereof, or a combination thereof and a pharmaceutically acceptable carrier, in the manufacture of a medicament for treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment is a use of a pharmaceutical composition comprising a tryptamine, an erinacine, a hericenone, a cannabinoid, or a pharmaceutically acceptable salt, hydrate, solvate, prodrug, stereoisomer, or tautomer thereof, a combination thereof in the manufacture of a medicament for treating or preventing neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment is a method for treating or preventing neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof in in a subject in need thereof comprising administering a composition comprising a tryptamine, an erinacine, a hericenone, a cannabinoid, or a pharmaceutically acceptable salt, hydrate, solvate, prodrug, stereoisomer, or tautomer thereof, or a combination thereof to the subject.

Another embodiment is a use of a compound comprising a tryptamine, an erinacine, a hericenone, a cannabinoid, or a pharmaceutically acceptable salt, hydrate, solvate, prodrug, stereoisomer, or tautomer thereof, in the manufacture of a medicament for treating or preventing neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health.

Another embodiment is the addition of a monamine oxidase inhibitor, such as β-carbolines (e.g., harmane, harmine, nor harmine, perlolyrine, harmol, cordysinin, inter alia), to any of the above mentioned compositions or methods to enhance the pharmaceutical efficacy of the tryptamine(s).

Combination Therapies

Another embodiment is a pharmaceutical combination comprising one or more of a tryptamine, an erinacine, a hericenone, a cannabinoid, or a pharmaceutically acceptable salt, hydrate, solvate, prodrug, stereoisomer, or tautomer thereof, a combination thereof, and one or more additional therapeutic agent(s) for simultaneous, separate or sequential use in therapy for neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health. In one embodiment, the additional therapeutic agent is selected from the group consisting of: an antiproliferative agent, anticancer agent, immunomodulatory agent, an anti-inflammatory agent, a neurological treatment agent, an anti-viral agent, an anti-fungal agent, anti-parasitic agent, an antibiotic, and a general anti-infective agent.

One embodiment described herein is neurotrophic and nootropic compositions and methods for treating subjects with such compositions. In one aspect the composition comprises one or more tryptamines or in pure form or extracts from psilocybin containing mushrooms, or combinations thereof combined with one or more phenethylamines or amphetamines in pure form or extract from a plant or mushroom, or combinations thereof, one or more erinacines or hericenones in pure form, extracts from Hericium mushroom species (e.g., H. *erinaceus, H. coralloides, H. ramosum*) or combinations thereof, one or more cannabinoids in pure form or extracts from *Cannabis sativa, Cannabis sativa, Cannabis indica*, or *Cannabis ruderalis*, optionally, one or more adversive compounds such as niacin, capsaicin, ipecac, apomorphine, bittering agents (e.g., denatonium benzoate), inter alia, and one or more pharmaceutically acceptable excipients.

In one embodiment, the composition is described in Table 1. Compositions may contain one or more species or combinations of any of the species listed in Table 1.

TABLE 1

Exemplary neurotropic or nootropic compositions

| Component | Example | Dosage |
|---|---|---|
| Tryptamine neurotrophics, tryptamine derivatives, esters, or salts thereof, or extracts from fungi or plants; In addition to or alternatively, phenethylamines, amphetamines; derivatives thereof, extracts from fungi or plants | Psilocybin, baeocystin, norbaeocystin, psilocin, norpsilocin, 4-hydroxytryptamine, N,N-dimethyltryptamine, N-methyltryptamine, inter alia; In addition or alternatively, 3,4,5-trimethoxyphenethylamine (Mescaline), 2,4-dimethoxy-amphetamine (2,4-DMA), 3,4-dimethoxy-amphetamine (3,4-DMA), 3,4-methylenedioxy-amphetamine (MDA), 3-methoxy-4,5-methylendioxy-amphetamine (MMDA), inter alia | 10 ng to 10 mg |
| Optional secondary neurotrophic fungal or plant extracts, or purified compounds thereof | Erinacines, hericenones, cannabidiol, cannabichromene, cannabigerol, Δ8-tetrahydrocannabinol, Δ9-tetrahydrocannabinol, cannabinol, tetrahydrocannabivarin, cannabidiol-2',6'-dimethyl ether, Ketamine, inter alia | 10 ng to 500 mg |
| Optional neurotropic or nootropic fungal or plant extracts, or other natural products, or purified compounds thereof | *Antrodia*, *Beauveria*, *Copelandia*, *Cordyceps*, *Fomitopsis*, *Ganoderma*, *Grifola*, *Hericium*, *Hypsizygus*, *Inonotus*, *Isaria*, *Panaeolus*, *Phellinus*, *Phellinus*, *Piptoporus*, *Pleurotus*, *Polyporus*, *Pochonia chlamydosporia*, or *Trametes* species or combinations thereof; *Bacopa monnien*, *Centella asiatica*, *Gingko biloba*, *Zingiber officinale*, *Ocimum sanctum*, *Polygonum cuspidatum*, *Origanum vulgare*, *Origanum onites*, *Rosmarinus officinalis*, *Rosmarinus eriocalyx*, *Curcuma longa*, *Camellia sinensis*, *Psychotria viridis*, inter alia | 10 μg to 500 mg |

TABLE 1-continued

Exemplary neurotropic or nootropic compositions

| Component | Example | Dosage |
|---|---|---|
| Optional MAO inhibitor compounds | β-carbolines (e.g., harmane, harmine, nor harmine, perlolyrine, harmol, cordysinin, inter alia) | 10 ng to 10 mg |
| Optional adversive | Niacin, capsaicin, ipecac, apomorphine, bittering agents (e.g., denatonium benzoate) inter alia | 10 μg to 200 mg |
| Optional pharmaceutical excipients | Fillers, binders, diluents, vehicles, lubricants, preservatives, flavors, colors, etc. | quantum sufficit |

Compositions may contain one or more species or combinations of any of the species listed above. Compositions can be liquid, suspensions, emulsions, dry powder admixtures, or combinations thereof.

One embodiment described herein is a composition comprising one or more tryptamines such as psilocybin (4-phosphoryloxy-N,N-dimethyltryptamine), baeocystin, (4-phosphoryloxy-N-methyltryptamine), norbaeocystin (4-phosphoryloxy-tryptamine), psilocin (4-hydroxy-N,N-dimethyltryptamine, norpsilocin (4-hydroxy-N-methyl-tryptamine), N,N-dimethyltryptamine, 4-hydroxytryptamine, inter alia, in pure form or comprising extracts from Psilocybe and psilocybin containing mushrooms, or combinations thereof.

Another embodiment is a composition of one or more tryptamines or in pure form or extracts from psilocybin containing mushrooms, or combinations thereof, and further combined with one or more adversive compounds such as niacin, ipecac, apomorphine, bittering agents (e.g., denatonium benzoate), capsaicin, capsacutin dihydrocapsaicin, nordihydrocapsaicin, homocapsaicin, homodihydrocapsaicin, capsaicinoids, gingerol, piperine, isopiperine, zingerone, shogaol, vanillylamide derivatives, or combinations thereof, inter alia.

Another embodiment is a composition of one or more tryptamines or in pure form or extracts from psilocybin containing mushrooms, or combinations thereof combined with one or more erinacines or hericenones in pure form, extracts from Hericium mushroom species, or combinations thereof.

Another embodiment is a composition of one or more tryptamines or in pure form or extracts from psilocybin containing mushrooms, or combinations thereof combined with one or more erinacines or hericenones in pure form, extracts from Hericium mushroom species (e.g., H. *erinaceus, H. coralloides, H. ramosum*) or combinations thereof, and further combined with one or more adversive compounds such as niacin, capsaicin, ipecac, apomorphine, bittering agents (e.g., denatonium benzoate), inter alia.

Another embodiment is a composition of one or more tryptamines or in pure form or extracts from psilocybin containing mushrooms, or combinations thereof combined with one or more phenethylamines or amphetamines in pure form or extract from a plant or mushroom, or combinations thereof, one or more erinacines or hericenones in pure form, extracts from Hericium mushroom species (e.g., H. *erinaceus, H. coralloides, H. ramosum*) or combinations thereof, and further combined with one or more adversive compounds such as niacin, capsaicin, ipecac, apomorphine, bittering agents (e.g., denatonium benzoate), inter alia.

Another embodiment is a composition of one or more tryptamines or in pure form or extracts from psilocybin containing mushrooms, or combinations thereof combined with one or more cannabinoids in pure form or extracts from *Cannabis sativa, Cannabis sativa, Cannabis indica*, or *Cannabis ruderalis.*

Another embodiment is a composition of one or more tryptamines or in pure form or extracts from psilocybin containing mushrooms, or combinations thereof combined with one or more cannabinoids in pure form or extracts from *Cannabis sativa, Cannabis sativa, Cannabis indica*, or *Cannabis ruderalis*, and further combined with one or more adversive compounds such as niacin, capsaicin, ipecac, apomorphine, bittering agents (e.g., denatonium benzoate), inter alia.

Another embodiment is a composition of one or more tryptamines or in pure form or extracts from psilocybin mushrooms containing fungi, extracts thereof or pure chemicals thereof; or plant extracts, or pure chemicals thereof; or combinations thereof.

One embodiment is a composition of one or more tryptamines or in pure form or extracts from psilocybin mushrooms combined with one or more extracts or pure chemicals from other fungi comprising one or more of Antrodia, *Beauveria, Copelandia, Cordyceps, Fomitopsis, Ganoderma*, Grifola, Hericium, *Hypsizygus*, Inonotus, Isaria, Panaeolus, *Phellinus* Piptoporus, *Pleurotus*, Polyporus or *Trametes* species or combinations thereof; a mycelium extract of Antrodia, *Beauveria, Copelandia, Cordyceps, Ganoderma*, Fomitopsis, Grifola, Hericium, *Hypsizygus*, Inonotus, Isaria, Panaeolus, *Phellinus, Piptoporus, Pleurotus*, Polyporus or *Trametes* species, or combinations thereof; or a fruitbody extract of Antrodia, *Beauveria, Copelandia, Cordyceps, Fomitopsis, Ganoderma*, Grifola, Hericium, *Hypsizygus*, Inonotus, Isaria, Panaeolus, *Phellinus, Piptoporus, Pleurotus*, Polyporus or *Trametes* species, or combinations thereof.

In one aspect described herein, the fungi comprise one of more of Antrodia camphoratus, Antrodia *cinnamomea, Fomitopsis officinalis, Ganoderma annulare, Ganoderma applanatum, Ganoderma brownii, Ganoderma lucidum, Ganoderma lingzhi, Ganoderma resinaceum, Hypsizygus tessulatus, Hypsizygus ulmarius, Inonotus obliquus, Trametes versicolor, Pochonia chlamydosporia*, or *Pleurotus* ostreatus.

In another aspect described herein, the fungi comprise one or more of *Agaricus* augustus, *Agaricus* blazei, *Agaricus* bonardii, *Agaricus brasiliensis, Agaricus campestris, Agaricus lilaceps, Agaricus subrufescens, Agaricus* sylvicola, Agrocybe aegerita, Agrocybe arvalis, Agrocybe pediades, Agrocybe *praecox, Antrodia cinnamonea, Clitocybe odora, Conocybe cyanopus, Conocybe lacteus, Conocybe rickenii, Conocybe smithii, Conocybe tenera, Coprinopsis lagopus, Coprinopsis nivea, Coprinus comatus, Coprinus* micaceus, Fomitiporia *robusta, Fomitopsis officinalis* (Laricifomes *officinalis*), *Ganoderma* atrum, *Ganoderma brownii, Ganoderma curtisii, Ganoderma lingzhi, Ganoderma oregonense, Ganoderma tsugae*, Gymnopus hydrophilus, Gymnopus peronatus, Hericium *erinaceus, Hericium coralloides, Hericium ramosum, Heterobasidion annosum, Hypholoma aurantiaca* (Leratiomyces ceres), *Hypholoma* capnoides, *Hypholoma* sublateritium, *Hypsizygus marmoreus, Hypsizygus tessulatus, Hypsizygus ulmarius, Inonotus andersonii*, Inonotus dryadeus, Inonotus *hispidus*, Laetiporus cincinnatus, Laetiporus conifericola, Laetiporus *sulphureus*, Lentinus ponderosus, Lenzites betulina, *Lepiota procera* (Macrolepiota *procera*), *Lepiota* rachodes (*Chlorophyllum* rachodes), Lepista *nuda, Mycena alcalina, Mycena aurantiadisca, Mycena pura*, Panaeolus foenisecii, Panaeolus subbalteatus, *Panellus serotinus, Panellus serotinus, Panellus stipticus, Phellinus igniarius, Phellinus linteus, Phellinus pini, Piptoporus betulinus, Pleurotus columbinus, Pleurotus cystidiosus, Pleurotus ostreatus, Pleurotus pulmonarius, Pleurotus sapidus, Pleurotus* tuberregium, Pluteus cervinus, Polyporus *elegans, Psathyrella aquatica*, Psathyrella condolleana, Psathyrella *hydrophila*, Psilocybe allenii, Psilocybe azurescens, Psilocybe *caerulescens*, Psilocybe coprophila, Psilocybe *cubensis*, Psilocybe cyanescens, Psilocybe ovoideocystidiata, Psilocybe stuntzii, Psilocybe subaeruginosa, *Stereum* complicatum, *Stereum hirsutum, Stereum ostrea, Stropharia aeruginosa, Stropharia cyanea, Stropharia* rugoso-*annulata, Stropharia semiglobata, Stropharia semigloboides, Stropharia squamosa, Stropharia thrausta, Stropharia* umbonotescens, Termitomyces *robusta, Trametes aesculi, Trametes cingulata, Trametes ectypa, Trametes elegans, Trametes gibbosa, Trametes hirsuta, Trametes ochracea, Trametes pubescens, Trametes villosa, Volvaria bombycina, Volvariella volvacea, Wolfiporia cocos*, or combinations thereof. The above composition can also contain one or more adversive compounds as described herein.

Another embodiment is a composition of one or more tryptamines or in pure form or extracts from psilocybin containing mushrooms, or combinations thereof combined with one or more extracts or pure chemicals from plant species comprising one or more of Bacopa species (Bacopa monnien), Gotu kola (Centella *asiatica*), and Gingko (Gingko *biloba*, Ginger (*Zingiber officinale*), Holy Basil (*Ocimum* sanctum), Hu Zhang (*Polygonum cuspidatum*), Oregano (*Origanum vulgare, Origanum* onites), Rosemary (*Rosmarinus officinalis, Rosmarinus eriocalyx*, species in the genus *Rosmarinus*), Turmeric (*Curcuma longa*), Green Tea (*Camellia sinensis*), lavender (*Lavandula* spica and related species in the genus *Lavandula*), skullcap (Scutellaria lateriflora) oat straw (*Avena sativa, Avena byzantina*), *Salvia* divinorum, aka Diviner's Sage, Banisteriopsis caapi and Psychotria species, plants containing ibogaine (Tabemanthe iboga, Voacanga *africana* and Tabemaemontana undulate), peyote (Lophophora williamsii), the seeds of morning glory (*Ipomoea tricolor* and related species) and Hawaiian baby wood rose (Argyreia nervosa), Acacia *confusa, Acacia obtusifolia, Acacia simplicifolia*, Desmanthus Illinoensis, or *Cannabis* (*Cannabis sativa, C. indica* and *C. ruderalis*). The above composition can also contain one or more adversive compounds as described herein.

Another embodiment is a composition of one or more tryptamines or in pure form or extracts from psilocybin containing mushrooms, or combinations thereof combined with one or more monamine oxidase (MAO) inhibitors, such as β-carbolines (e.g., harmane, harmine, norharmine, perlolyrine, harmol, cordysinin, inter alia), to any of the above mentioned compositions to enhance the pharmaceutical efficacy of the tryptamine(s).

Pharmaceutical excipients useful for the compositions as described herein comprise: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein. See Remington's Essentials of Pharmaceutics, Pharmaceutical Press Publishing Company, London, UK, 1$^{st}$ Edition, 2013, and the Handbook of Pharmaceutical Excipients, $_{8}$h Edition, Pharmaceutical Press Publishing Company London, U K, 2017, each of which is incorporated by reference herein for such teachings.

Another embodiment is a method for manufacturing a dosage form comprising formulating a composition as described herein comprising sprays, capsules, tablets, elixirs, emulsions, lozenges, suspensions, syrups, pills, lotions, epidermal patches, suppositories, inhalers, or injectables. Any methods known to the art for formulating extracts or active principal ingredients into lotions, soaps, etc. may be utilized.

In one embodiment, the pharmaceutical composition comprises a dose of about 1 ng to about 10 mg of one or more tryptamines or an amount of a mushroom (or plant) extract or mushroom (or plant) having an equivalent amount of tryptamine(s). In another embodiment, the composition comprises about 1 μg to about 100 μg of one or more tryptamines or an amount of a mushroom extract or mushroom having an equivalent amount of tryptamine(s). In another embodiment, the composition comprises about 1 μg to about 5 mg of one or more tryptamines or an amount of a mushroom extract or mushroom having an equivalent amount of tryptamine(s).

In another embodiment, the composition comprises about 100 μg to about 1 mg of one or more tryptamines or an amount of a mushroom extract or mushroom having an equivalent amount of tryptamine(s). In one aspect, the composition comprises about: 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390 μg, 400 μg, 410 μg, 420 μg, 430 μg, 440 μg, 450 μg, 460 μg, 470 μg, 480 μg, 490 μg, 500 μg, 510 μg, 520 μg, 530 μg, 540 μg, 550 μg, 560 μg, 570 μg, 580 μg, 590 μg, 600 μg, 610 μg, 620 μg, 630 μg, 640 μg, 650 μg, 660 μg, 670 μg, 680 μg, 690 μg, 700 μg, 710 μg, 720 μg, 730 μg, 740 μg, 750 μg, 760 μg, 770 μg, 780 μg, 790 μg, 800 μg, 810 μg, 820 μg, 830 μg, 840 μg, 850 μg, 860 μg, 870 μg, 880 μg, 890 μg, 900 μg, 910 μg, 920 μg, 930 μg, 940 μg, 950 μg, 960 μg, 970 μg, 980 μg, 990 μg, or 1000 μg of one or more tryptamines or an amount of a mushroom extract or mushroom having an equivalent amount of tryptamine(s). In another aspect, the composition comprises about: 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg of one or more tryptamines or an amount of a mushroom extract or mushroom having an equivalent amount of tryptamine(s).

The percent mass of psilocybin, psilocin, and baeocystin in dried Psilocybe mushrooms is shown in Table 2.

TABLE 2

Psilocybin, psilocin, and baeocystin concentrations in psilocybe mushrooms

| Species | Mass percent based on dry weight of mushroom | | |
|---|---|---|---|
| | Psilocybin | Psilocin | Baeocystin |
| *P. azurescens* | 1.78 | 0.38 | 0.35 |
| *P. bohemica* | 1.34 | 0.11 | 0.02 |
| *P. semilanceata* | 0.98 | 0.02 | 0.36 |
| *P. baeocystis* | 0.85 | 0.59 | 0.10 |
| *P. cyanescens* | 0.85 | 0.36 | 0.03 |
| *P. tampanensis* | 0.68 | 0.32 | n/d |
| *P. cubensis* | 0.63 | 0.60 | 0.025 |
| *P. weilii* | 0.61 | 0.27 | 0.05 |
| *P. hoogshagenii* | 0.60 | 0.10 | n/d |
| *P. stuntzii* | 0.36 | 0.12 | 0.02 |
| *P. cyanofibrillosa* | 0.21 | 0.04 | n/d |
| *P. liniformans* | 0.16 | n/d | 0.05 |
| Average | 0.754% | 0.243% | 0.137% |

Data from Stamets, *Psilocybin Mushrooms of the World*, Ten Speed Press, page 39 (1996)

Table 3 shows the relative amount of psilocybin, psilocin, and baeocystin in dried Psilocybe mushrooms.

TABLE 3

Relative amounts of psilocybin, psilocin, baeocystin in dry *Psilocybe* mushrooms

| Dry Mushroom g | Psilocybin 0.754% mg | Psilocin 0.243% mg | Baeocystin 0.137% mg |
|---|---|---|---|
| 0.2-0.8 | 1.5-6.0 | 0.5-1.9 | 0.3-1.1 |
| 0.8-1.0 | 6.0-7.5 | 1.9-2.4 | 1.1-1.4 |
| 1.0-1.5 | 7.5-11.3 | 2.4-3.6 | 1.4-2.1 |
| 1.5-3.0 | 11.3-22.6 | 3.6-7.3 | 2.1-4.1 |
| 3.0-4.0 | 22.6-30.2 | 7.3-9.7 | 4.1-5.5 |
| 4.0-5.0 | 30.2-37.7 | 9.7-12.2 | 5.5-6.9 |

Based on data from Stamets, *Psilocybin Mushrooms of the World*, Ten Speed Press, page 39 (1996)

In one embodiment, the dose of tryptamine is about 0.00001 mg/kg to about 0.2 mg/kg, assuming an average mass of 70 kg for a human. In one embodiment, the dose of tryptamine is 0.0001 mg/kg to about 0.001 mg/kg. In another embodiment, the dose of tryptamine is 0.001 mg/kg to about 0.01 mg/kg. In another embodiment, the dose of tryptamine is 0.01 mg/kg to about 0.1 mg/kg. In another embodiment, the dose of tryptamine is 0.1 mg/kg to about 0.2 mg/kg. In another embodiment, the dose of tryptamine is about 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, 0.20 mg/kg, In another embodiment, the dose of tryptamine is about 0.01 mg/kg to about 0.05 mg/kg. In another embodiment, the dose of tryptamine is about 0.01 mg/kg to about 0.02 mg/kg.

In one embodiment, the dose of the phenethylamines, amphetamines, erinacines, hericenones, cannabinoids one or more adversive compounds such as niacin, capsaicin, ipecac, apomorphine, bittering agents, or an amount of a mushroom or plant extract or mushroom or plant having an equivalent amount of about 1 ng, 5 ng, 10 ng, 20 ng, 30 ng, 40 ng, 50 ng, 60 ng, 70 ng, 80 ng, 90 ng, 100 ng, 110 ng, 120 ng, 130 ng, 140 ng, 150 ng, 160 ng, 170 ng, 180 ng, 190 ng, 200 ng, 210 ng, 220 ng, 230 ng, 240 ng, 250 ng, 260 ng, 270 ng, 280 ng, 290 ng, 300 ng, 310 ng, 320 ng, 330 ng, 340 ng, 350 ng, 360 ng, 370 ng, 380 ng, 390 ng, 400 ng, 410 ng, 420 ng, 430 ng, 440 ng, 450 ng, 460 ng, 470 ng, 480 ng, 490 ng, 500 ng, 510 ng, 520 ng, 530 ng, 540 ng, 550 ng, 560 ng, 570 ng, 580 ng, 590 ng, 600 ng, 610 ng, 620 ng, 630 ng, 640 ng, 650 ng, 660 ng, 670 ng, 680 ng, 690 ng, 700 ng, 710 ng, 720 ng, 730 ng, 740 ng, 750 ng, 760 ng, 770 ng, 780 ng, 790 ng, 800 ng, 810 ng, 820 ng, 830 ng, 840 ng, 850 ng, 860 ng, 870 ng, 880 ng, 890 ng, 900 ng, 910 ng, 920 ng, 930 ng, 940 ng, 950 ng, 960 ng, 970 ng, 980 ng, 990 ng, or 1000 ng; 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390 μg, 400 μg, 410 μg, 420 μg, 430 μg, 440 μg, 450 μg, 460 μg, 470 μg, 480 μg, 490 μg, 500 μg, 510 μg, 520 μg, 530 μg, 540 μg, 550 μg, 560 μg, 570 μg, 580 μg, 590 μg, 600 μg, 610 μg, 620 μg, 630 μg, 640 μg, 650 μg, 660 μg, 670 μg, 680 μg, 690 μg, 700 μg, 710 μg, 720 μg, 730 μg, 740 μg, 750 μg, 760 μg, 770 μg, 780 μg, 790 μg, 800 μg, 810 μg, 820 μg, 830 μg, 840 μg, 850 μg, 860 μg, 870 μg, 880 μg, 890 μg, 900 μg, 910 μg, 920 μg, 930 μg, 940 μg, 950 μg, 960 μg, 970 μg, 980 μg, 990 μg, or 1000 μg; 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg; 0.1 mg, 0.25 mg, 0.5 mg, 1.0 mg, 2.5 mg, 5.0 mg, 10.0 mg, 20.0 mg, 30.0 mg, 40.0 mg, 50.0 mg, 60.0 mg, 70.0 mg, 80.0 mg, 90.0 mg, or 100.0 mg; 1 mg, 5 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg of compound.

In one embodiment, the dose of the phenethylamines, amphetamines, erinacines, hericenones, cannabinoids one or more adversive compounds such as niacin, capsaicin, ipecac, apomorphine, bittering agents, or an amount of a mushroom or plant extract or mushroom or plant having an equivalent amount of about 0.1 mg/kg, 0.25 mg/kg, 0.5 mg/kg, 0.75 mg/kg, 1 mg/kg, 2.5 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg.

In one embodiment, the pharmaceutical composition comprises:

0.001 mg to 0.01 mg, 0.01 mg to 0.1 mg, 0.01 mg to 1 mg, 0.1 mg to 5 mg, 0.1 mg to 1 mg, 0.5 mg to 1 mg, 0.5 mg to 5 mg, 0.25 mg to 1 mg, 0.2 mg to 2 mg, 0.2 mg to 5 mg of one or more tryptamines or an amount of a plant or mushroom extract or plant or mushroom to provide an equivalent dose; and/or 0.1 mg to 1 mg, 1 mg to 10 mg, 10 mg to 100 mg, 10 mg to 50 mg, 50 mg to 100 mg, 20 mg to 80 mg, 20 mg to 50 mg, 50 mg to 100 mg, 50 mg to 80 mg, 10 mg to 80 mg phenethylamines or amphetamines or an amount of a plant or mushroom extract or plant or mushroom to provide an equivalent dose; and/or 1 µg to 5 µg, 1 µg to 10 µg, 5 µg to 10 µg, 10 µg to 5 mg, 10 µg to 100 µg, 100 µg to 1 mg, 500 µg to 1 mg, 500 µg to 5 mg, 1 mg to 5 mg, 100 µg to 1 mg, 100 µg to 500 µg, 100 µg to 250 µg; 250 µg to 1 mg; 750 µg to 1 mg, 250 µg to 750 µg, erinacines or hericenones or an amount of a plant or mushroom extract or plant or mushroom to provide an equivalent dose; and/or 0.01 mg to 0.1 mg, 0.01 mg to 1 mg, 0.1 mg to 10 mg, 0.1 mg to 1 mg, 0.5 mg to 1 mg, 0.5 mg to 5 mg, 0.25 mg to 1 mg, 0.2 mg to 2 mg, 0.2 mg to 5 mg, 1 mg to 10 mg cannabinoids or an amount of a plant extract or plant or mushroom to provide an equivalent dose; and/or 0.1 mg to 10 mg, 1 mg to 500 mg, 1 mg to 100 mg, 200 mg to 500 mg, 50 mg to 200 mg, 10 mg to 50 mg, 50 mg to 200 mg, 1 mg to 200 mg, 1 mg to 50 mg of adversive.

In one embodiment, the pharmaceutical compositions described herein provide a dosage form of the pharmaceutical compositions described here for administration to a subject. In one embodiment, the subject is suffering from or has the symptoms of one or more neurologic diseases or disorders or wishes to enhance one or more cognitive or sensory motor traits. The dosage form can be administered, for example, to a subject, or a subject in need thereof. In one aspect, the subject is a mammal, or a mammal in need thereof. In one aspect, the subject is a human, or human in need thereof. In one aspect, the subject is a human or a human in need thereof. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (>18 years of age).

One or more dosage forms of the compositions described herein can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to a neurological or neurodegenerative disease or disorder.

In one embodiment, the compositions described herein can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage.

Another embodiment described herein is a method of treating a subject suffering from or having the symptoms of a neurological or neurodegenerative disease or disorder by orally administering one or more of the pharmaceutical compositions described herein to the subject. The composition may be administered in one or more doses, one or more times per day for a total daily dosage.

In one aspect, the compositions described herein are effective to at least partially treat, alleviate, prevent or ameliorate serotonin (5-hydroxytryptamine, 5-HT) receptor disorders, psychiatric, or mood disorders, e.g., depression, anxiety, major depressive disorder, treatment resistant depression, persistent depression, manic depression or bipolar disorder, depressive psychosis, perinatal depression, premenstrual dysphoric disorder, seasonal depressions, situational depression, panic disorder, obsessive compulsive disorder, post-traumatic stress disorder, attention deficit/hyperactivity disorder, sleep disorders, eating disorders, schizophrenia, personality disorders, substance abuse disorders (drug abuse, addiction, alcoholism); neuronal injuries or physical neurodegeneration (e.g., physical injury, head trauma, spinal cord trauma, concussion, peripheral neuron trauma, paralysis, ischemia, hypoxia, stroke; organophosphates, lead, heavy metals, nerve agents, other toxic compounds, prions, amyloid plaque, neurotoxic viruses, stress); neurodegenerative diseases (e.g., Alzheimer's disease, Parkinson's disease, amyotrophic lateral sclerosis, multiple sclerosis, frontotemporal dementia, Huntington's disease, adrenal leukodystrophy, Alexander's disease, Alper's disease, Alzheimer's disease, amyotrophic lateral sclerosis, balo concentric sclerosis, Canavan disease, Charcot-Marie-Tooth disease, childhood ataxia with central nervous system hypomyelination, chronic idiopathic peripheral neuropathy, frontotemporal dementia, Huntington's disease, Krabbe disease, monomelic amyotrophy, multiple sclerosis (MS), neurodegeneration, neuromyelitis optica, neuropathic pain, neurosarcoidosis, Parkinson's disease, Pelizaeus-Merzbacher disease, primary lateral sclerosis, progressive supranuclear palsy, radicular pain, radiculopathic pain, Schilder's disease, sciatic pain, sciatica, subacute necrotizing myelopathy, transverse myelitis, or Zellweger syndrome); congenital or organic cognitive impairment, learning disabilities, autism spectrum disorder; cognitive enhancement, intelligence enhancement, creativity enhancement, memory improvement, learning enhancement and improvement, spiritual enhancement, "mind expansion," IQ improvement, EQ improvement, balance enhancement, athleticism, motor skill enhancement, special navigation, clairvoyance, psychic enhancement, or general improvement of mental health.

One embodiment described herein is a composition comprising one or more of a tryptamine, a phenethylamine, an amphetamine, an erinacine, a hericenone, a cannabinoid, or a pharmaceutically acceptable salt, hydrate, solvate, prodrug, stereoisomer, or tautomer thereof, or a combination thereof, and a pharmaceutically acceptable carrier, for use in treating neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof.

Another embodiment described herein is a method of treating, preventing, ameliorating or reducing the symptoms of serotonin (5-hydroxytryptamine, 5-HT) receptor disorders, neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health in a subject in need thereof by administering a composition comprising one or more of a tryptamine, a phenethylamine, an amphetamine, an erinacine, a hericenone, a cannabinoid, or a pharmaceutically acceptable salt, hydrate, solvate, prodrug, stereoisomer, or tautomer thereof, or a combination thereof, and a pharmaceutically acceptable carrier.

In one embodiment, the tryptamine comprises psilocybin, baeocystin, norbaeocystin, psilocin, norpsilocin, 4-hydroxytryptamine, N,N-dimethyltryptamine, 5-hydroxytryptamine (serotonin), tryptamine, aeruginascin, 4-hydroxy-N,N,N-trimethyltryptamine, 5-hydroxy-N,N,N-trimethyltryptamine (bufotenidine), N-methyltryptamine, N-ethyltryptamine, N-methyl-N-ethyltryptamine, N-methyl-N-propyltryptamine, N,N-diethyltryptamine, N-methyl-N-isopropyltryptamine, N-ethyl-N-isopropyltryptamine, N,N-diisopropyltryptamine, N,N-dipropyltryptamine, N,N-dipropyltryptamine, N,N-diallyltryptamine, 4-hydroxytryptamine, 4-hydroxy-N-methyltryptamine (norpsilocin), 4-hydroxy-N,N-dimethyltryptamine (psilocin), 4-hydroxy-N-methyl-N-ethyltryptamine, 4-hydroxy-N-methyl-N-propyltryptamine, 4-hydroxy-N,N-diethyltryptamine, 4-hydroxy-N,N-diethyltryptamine, 4-hydroxy-N-ethyl-N-isopropyltryptamine, 4-hydroxy-N,N-diisopropyltryptamine, 4-hydroxy-N,N-dipropyltryptamine, 4-hydroxy-N-N-dipropyltryptamine, 4-hydroxy-N,N-diallyltryptamine, 4-methoxytryptamine, 4-methoxy-N-methyltryptamine (norpsilocin), 4-methoxy-N,N-dimethyltryptamine (psilocin), 4-methoxy-N-methyl-N-ethyltryptamine, 4-methoxy-N-methyl-N-propyltryptamine, 4-methoxy-N,N-diethyltryptamine, 4-methoxy-N,N-diethyltryptamine, 4-methoxy-N-ethyl-N-isopropyltryptamine, 4-methoxy-N,N-diisopropyltryptamine, 4-methoxy-N,N-dipropyltryptamine, 4-methoxy-N-N-dipropyltryptamine, 4-methoxy-N-N-diallyltryptamine, 4-acetoxytryptamine, 4-acetoxy-N-methyltryptamine, 4-acetoxy-N-methyl-N-ethyltryptamine, 4-acetoxy-N-methyl-N-ethyltryptamine, 4-acetoxy-N-methyl-N-propyltryptamine, 4-acetoxy-N,N-diethyltryptamine, 4-acetoxy-N-methyl-N-isopropyltryptamine, 4-acetoxy-N-ethyl-N-isopropyltryptamine, 4-acetoxy-N,N-diisopropyltryptamine, 4-acetoxy-N,N-dipropyltryptamine, 4-acetoxy-N-N-dipropyltryptamine, 4-acetoxy-N-N-diallyltryptamine, 5-hydroxytryptamine, 5-hydroxy-N-methyltryptamine, 5-hydroxy-N,N-dimethyltryptamine (bufotenine), 5-hydroxy-N-methyl-N-ethyltryptamine, 5-hydroxy-N-methyl-N-propyltryptamine, 5-hydroxy-N,N-diethyltryptamine, 5-hydroxy-N-methyl-N-isopropyltryptamine, 5-hydroxy-N-ethyl-N-isopropyltryptamine, 5-hydroxy-N,N-diisopropyltryptamine, 5-hydroxy-N,N-dipropyltryptamine, 5-hydroxy-N-N-dipropyltryptamine, 5-hydroxy-N-N-diallyltryptamine, 5-methoxytryptamine, 5-methoxy-N-methyltryptamine, 5-methoxy-N,N-dimethyltryptamine, 5-methoxy-N-methyl-N-ethyltryptamine, 5-mehoxy-N-methyl-N-propyltryptamine, 5-methoxy-N,N-diethyltryptamine, 5-methoxy-N-methyl-N-isopropyltryptamine, 5-methoxy-N-ethyl-N-isopropyltryptamine, 5-methoxy-N,N-diisopropyltryptamine, 5-methoxy-N,N-dipropyltryptamine, 5-methoxy-N-N-dipropyltryptamine, 5-methoxy-N-N-diallyltryptamine, 5-acetoxytryptamine, 5-acetoxy-N-methyltryptamine, 5-acetoxy-N,N-dimethyltryptamine, 5-acetoxy-N-methyl-N-ethyltryptamine, 5-mehoxy-N-methyl-N-propyltryptamine, 5-acetoxy-N,N-diethyltryptamine, 5-acetoxy-N-methyl-N-isopropyltryptamine, 5-acetoxy-N-ethyl-N-isopropyltryptamine, 5-acetoxy-N,N-diisopropyltryptamine, 5-acetoxy-N,N-dipropyltryptamine, 5-acetoxy-N-N-dipropyltryptamine, 5-acetoxy-N-N-diallyltryptamine, α-methyltryptamine, N-ethyl-N-isopropyltryptamine, N-methyl-N-butyltryptamine, 2,α-dimethyltryptamine, α-N-dimethyltryptamine, α-methyl-N,N-dimethyltryptamine, α-ethyltryptamine, 2-methyl-N,N-dimethyltryptamine, 2-methyl-N,N-diethyltryptamine, 1-methylpsilocin, 5-methoxy-α-methyltryptamine, ibogaine, harmaline, 7-methoxy-1-methyl-1,2,3,4-tetrahydro-b-carboline (tetrahydroharmine), N,N-diethyl-D-lysergamide (LSD), 6-ally-N,N-diethyl-norlysergic acid (6-allyl-N,N-diethyl-norlysergic acid), 9,10-didehydro-N,N,6-triethylergoline-8b-carboxamide (6,N,N-triethyl-norlysergic acid), 9,10-didehydro-6-propyl-N,N-diethylergoline-8b-carboxamide (6-propyl-norlysergic acid), other tryptamine compounds, or a pharmaceutically acceptable salt, hydrate, solvate, prodrug, stereoisomer, or tautomer thereof, or a combination thereof.

In another embodiment, the tryptamine comprises: 6-Allyl-N,N-diethyl-norlysergic acid (AL-LAD), N,N-dibutyl-tryptamine (DBT), N,N-diethyl-tryptamine (DET), N,N-diisopropyl-tryptamine (DiPT), 5-methyoxy-α-methyl-tryptamine (α,O-DMS), N,N-dimethyl-tryptamine (DMT), 2,α-dimethyl-tryptamine (2,α-DMT), α,N-dimethyl-tryptamine (α,N-DMT), N,N-dipropyl-tryptamine (DPT), N-ethyl-N-isopropyl-tryptamine (EiPT), α-ethyl-tryptamine (AET), 6,N,N-tryptamineriethyl-norlysergic acid (ETH-LAD), 3,4-dihydro-7-methoxy-1-methyl-carboline (Harmaline), 7-methyoxy-1-methyl-carboline (Harmine), N,N-dibutyl-4-hydroxy-tryptamine (4-HO-DBT), N,N-diethyl-4-hydroxy-tryptamine (4-HO-DET), N,N-diisopropyl-4-hydroxy-tryptamine (4-HO-DiPT), N,N-dimethyl-4-hydroxy-tryptamine (4-HO-DMT), N,N-dimethyl-5-hydroxy-tryptamine (5-HO-DMT), N,N-dipropyl-4-hydroxy-tryptamine (4-HO-DPT), N-ethyl-4-hydroxy-N-methyl-tryptamine (4-HO-MET), 4-hydroxy-N-isopropyl-N-methyl-tryptamine (4-HO-MiPT), 4-hydroxy-N-methyl-N-propyl-tryptamine (4-HO-MPT), 4-hydroxy-N,N-tetramethylene-tryptamine (4-HO-pyr-tryptamine), 12-methoxyibogamine (Ibogaine), N,N-diethyl-lysergic acid (LSD), N-butyl-N-methyl-tryptamine (MBT), N,N-diisopropyl-4,5-methylenedioxy-tryptamine (4,5-MDO-DiPT), N,N-diisopropyl-5,6-methylenedioxy-tryptamine (5,6-MDO-DiPT), N,N-dimethyl-4,5-methylenedioxy-tryptamine (4,5-MDO-DMT), N,N-dimethyl-5,6-methylenedioxy-tryptamine (5,6-MDO-DMT), N-isopropyl-N-methyl-5,6-methylenedioxy-tryptamine (5,6-MDO-MiPT), N,N-diethyl-2-methyl-tryptamine (2-Me-DET), 2,N,N-tryptaminerimethyl-tryptamine (2-Me-DMT), N-acetyl-5-methoxy-tryptamine (melatonin), N,N-diethyl-5-methoxy-tryptamine (5-MeO-DET), N,N-diisopropyl-5-methoxy-tryptamine (5-MeO-DiPT), 5-methoxy-N,N-dimethyl-tryptamine (5-MeO-DMT), N-isopropyl-4-methoxy-N-methyl-tryptamine (4-MeO-MiPT), N-isopropyl-5-methoxy-N-methyl-tryptamine (5-MeO-MiPT), 5,6-dimethoxy-N-isopropyl-N-methyl-tryptamine (5,6-MeO-MiPT), 5-methoxy-N-methyl-tryptamine (5-MeO-NMT), 5-methoxy-N,N-tetramethylene-tryptamine (5-MeO-pyr-tryptamine), 6-methoxy-1-methyl-i1,2,3,4-tetrahydro-carboline (6-MeO-tryptamineHH), 5-methoxy-2,N,N-trimethyl-tryptamine (5-MeO-tryptamineMT), N,N-dimethyl-5-methylthio-tryptamine (5-MeS-DMT), N-isopropyl-N-methyl-tryptamine (MiPT), α-methyl-tryptamine (α-MT), N-ethyl-tryptamine (NET), N-methyl-tryptamine (NMT), 6-propyl-norlysergic acid (PRO-LAD), N,N-tetramethylene-tryptamine (pyr-T), Tryptamine (T), 7-methoxy-1-methyl-1,2,3,4-tetrahydro-carboline (Tetrahydroharmine), or α,N-dimethyl-5-methoxy-tryptamine (α,N,O-TMS), or a pharmaceutically acceptable salt, hydrate, solvate, prodrug, stereoisomer, or tautomer thereof, or a combination thereof. See Shulgin and Shulgin, TIHKAL: The Continuation, Transform Press (1997), which is incorporated by reference herein for the specific teachings thereof.

In one embodiment, the tryptamine comprises a compound having the structure of Formula 1, (1)

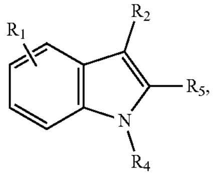

wherein $R_1$ is H, OH, COOH, $OCH_3$, $O(CH_2)_nCH_3$, $(CH_2)_nOH$, $(CH_2)_nCOOH$, $—C(O)CH_3$, $(CH_2)_nOC(O)N(R_6)_2$, $—(CH_2)_nC(O)OC(O)OH$, $PO_4$, $P_2O_7$, $P_3O_{10}$, $SO_4$, $S_2O_7$, $S_3O_{10}$, $CHO_3$, a $C_1$-$C_6$ mono- di-, or tri-carboxylic acid, a pentose sugar, a hexose sugar, or an amino acid;

$R_2$ is $(CH_2)_nN(R_6)_2$, $(CH_2)_nO(R_6)$, or $C_1$-$C_5$ alkyl-$N(R_7)_2$;

$R_4$ is H, $CH_3$, OH, $CHOCH_3$, or $(CH_2)_nOH$;

$R_5$ is H, $CH_3$, OH, $CHOCH_3$, or $(CH_2)_nCH_3$;

$R_6$ is H, $CH_3$, $C_1$-$C_4$ alkyl, OH, $CHOCH_3$, $(CH_2)_nOH$, $OCH_3$, $O(CH_2)_nCH_3$;

$R^7$ is independently H, $CH_3$, $C_1$-$C_4$ alkyl, $C_1$-$C_4$ allyl, $C_1$-$C_4$ ethynyl, OH, COOH, $(CH_2)_nCOOH$; $OCH_3$, $O(CH_2)_nCH_3$, $(CH_2)_nOH$, $(CH_2)_nNH_2$; dimethyl amine, pyrrole, pyrazole, imidazole, pyridine, piperdine, pyridine, pyrimidine, indole, purine, quinoline, morpholino, pyran, or furan;

where n is 0, 1, 2, 3, or 4; and wherein mono-, di-, and tri-carboxylic acids is selected from acetic acid, acetylsalicylic acid, adipic acid, alginic acid, arachidic acid, ascorbic acid, aspartic acid, benzenesulfonic acid, benzoic acid, bisulfic acid, boric acid, butyric acid, camphoric acid, camphorsulfonic acid, capric acid, caproic acid, caprylic acid, carbonic acid, citric acid, cyclopentanepropionic acid, digluconic acid, dodecylsulfic acid, enanthic acid, ethanesulfonic acid, formic acid, fumaric acid, glucoheptanoic acid, gluconic acid, glutamic acid, glutaric acid, glyceric acid, glycerophosphoric acid, glycine, glycolic acid, hemisulfic acid, heptanoic acid, hexanoic acid, hippuric acid, hydrobromic acid, hydrochloric acid, hydroiodic acid, hydroxyethanesulfonic acid, lactic acid, lauric acid, maleic acid, malic acid, malonic acid, mandelic acid, margaric acid, methanesulfonic acid, mucic acid, myristic acid, naphthylanesulfonic acid, naphthylic acid, nicotinic acid, nonadecylic acid, oxalic acid, oxalic acid, palmitic acid, pelargonic, pelargonic acid, pentadecylic acid, phosphoric acid, propionic acid, saccharin, salicylic acid, sorbic acid, stearic acid, succinic acid, sulfuric acid, tartaric acid, thiocyanic acid, thioglycolic acid, thiosulfuric acid, tosylic acid, trichloroacetic acid, tridecylic acid, trifluoroacetic acid, undecylenic acid, undecylic acid, valeric acid;

triose sugars are selected from D- or L-glyceraldehyde;

tetrose sugars are selected from D- or L- erythrose or threose, and their deoxy counterparts;

pentose sugars are selected from D- or L- arabinose, lyxose, ribose, xylose, ribulose, or xylulose, and their deoxy counterparts;

hexose sugars are selected from D- or L- allose, altrose, glucose, mannose, gulose, idose, galactose, talose, psicose, fructose, sorbose, tagatose, and their deoxy counterparts;

and amino acids are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, citrulline, taurine, selenocysteine, pyrrolysine, aminobutyric acid, gama-aminobutryic acid, 3-aminopropanoic acid, dehydroalanine, delta-carboxyglutamic acid, N-formylmethionine.

In another embodiment, the tryptamine comprises a compound having the structure of Formula 2A or 2B, (2A)

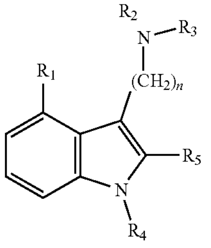

or (2B)

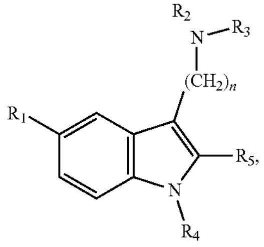

wherein:

$R_1$ is H, OH, COOH, $OCH_3$, $O(CH_2)_nCH_3$, $(CH_2)_nOH$, $(CH_2)_nCOOH$, $—C(O)CH_3$, $(CH_2)_nOC(O)N(R_6)_2$, $—(CH_2)_nC(O)OC(O)OH$, $PO_4$, $P_2O_7$, $P_3O_{10}$, $SO_4$, $S_2O_7$, $S_3O_{10}$, $CHO_3$, a $C_1$-$C_8$ mono- di-, or tri-carboxylic acid, a triose sugar, a tetrose sugar, a pentose sugar, a hexose sugar, or an amino acid;

$R_2$ and $R_3$ are independently H, $CH_3$, $C_1$-$C_4$ alkyl, $C_1$-$C_4$ allyl, $C_1$-$C_4$ ethynyl, OH, COOH, $(CH_2)_nCOOH$; $OCH_3$, $O(CH_2)_nCH_3$, $(CH_2)_nOH$, $(CH_2)_nNH_2$; dimethyl amine, pyrrole, pyrazole, imidazole, pyridine, piperdine, pyridine, pyrimidine, indole, purine, quinoline, morpholino, pyran, or furan;

$R_4$ is H, $CH_3$, OH, $CHOCH_3$, $(CH_2)_nOH$, $OCH_3$, $O(CH_2)_nCH_3$;

$R_5$ is H, $CH_3$, OH, $CHOCH_3$, $(CH_2)_nOH$, $OCH_3$, $O(CH_2)_nCH_3$ or $(CH_2)_nCH_3$; and $R_6$ is H, $CH_3$, $C_1$-$C_4$ alkyl, OH, $CHOCH_3$, $(CH_2)_nOH$, $OCH_3$, $O(CH_2)_nCH_3$;

where n is 0, 1, 2, 3, or 4;

wherein mono-, di-, and tri-carboxylic acids is selected from acetic acid, acetylsalicylic acid, adipic acid, alginic acid, arachidic acid, ascorbic acid, aspartic acid, benzenesulfonic acid, benzoic acid, bisulfic acid, boric acid, butyric acid, camphoric acid, camphorsulfonic acid, capric acid, caproic acid, caprylic acid, carbonic acid, citric acid, cyclopentanepropionic acid, digluconic acid, dodecylsulfic acid, enanthic acid, ethanesulfonic acid, formic acid, fumaric acid, glucoheptanoic acid, gluconic acid, glutamic acid, glutaric acid, glyceric acid, glycerophosphoric acid, glycine, glycolic acid, hemisulfic acid, heptanoic acid, hexanoic acid, hippuric acid, hydrobromic acid, hydrochloric acid, hydroiodic acid, hydroxyethanesulfonic acid, lactic acid, lauric acid, maleic acid, malic acid, malonic acid, mandelic acid, margaric acid, methanesulfonic acid, mucic acid, myristic acid, naphthylanesulfonic acid, naphthylic acid, nicotinic acid, nonadecylic acid, oxalic acid, oxalic acid, palmitic acid, pelargonic, pelargonic acid, pentadecylic acid, phosphoric acid, propionic acid, saccharin, salicylic acid, sorbic acid, stearic acid, succinic acid, sulfuric acid, tartaric acid, thiocyanic acid, thioglycolic acid, thiosulfuric acid, tosylic acid, trichloroacetic acid, tridecylic acid, trifluoroacetic acid, undecylenic acid, undecylic acid, valeric acid;

triose sugars are selected from D- or L-glyceraldehyde;

tetrose sugars are selected from D- or L- erythrose or threose, and their deoxy counterparts;

pentose sugars are selected from D- or L- arabinose, lyxose, ribose, xylose, ribulose, or xylulose, and their deoxy counterparts;

hexose sugars are selected from D- or L- allose, altrose, glucose, mannose, gulose, idose, galactose, talose, psicose, fructose, sorbose, tagatose, and their deoxy counterparts;

and amino acids are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, citrulline, taurine, selenocysteine, pyrrolysine, aminobutyric acid, gama-aminobutryic acid, 3-aminopropanoic acid, dehydroalanine, delta-carboxyglutamic acid, N-formylmethionine. In another embodiment, the tryptamine comprises a compound having the structure of Formula 3A or 3B, (3A)

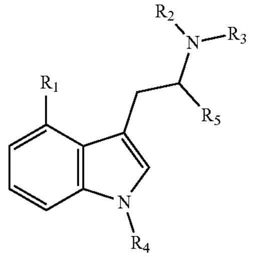

or (3B)

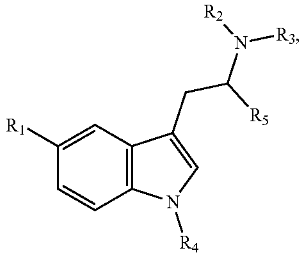

wherein:

$R_1$ is H, OH, COOH, $OCH_3$, $O(CH_2)_nCH_3$, $(CH_2)_nOH$, $(CH_2)_nCOOH$, $C(O)CH_3$, $(CH_2)_nOC(O)N(R_6)_2$, $(CH_2)_nC(O)OC(O)OH$, $PO_4$, $P_2O_7$, $P_3O_{10}$, $SO_4$, $S_2O_7$, $S_3O_{10}$, $CHO_3$, a $C_1$-$C_{22}$ mono- di-, or tri-carboxylic acid, a pentose sugar, a hexose sugar, or an amino acid;

$R_2$ and $R_3$ are independently H, $CH_3$, $(CH_2)_nCH_3$, OH, COOH, $(CH_2)_nCOOH$; $OCH_3$, $O(CH_2)_nCH_3$, $(CH_2)_nOH$, $(CH_2)_nNH_2$; dimethyl amine, pyrrole, pyrazole, imidazole, pyridine, piperdine, pyridine, pyrimidine, indole, purine, quinoline, morpholino, pyran, or furan;

$R_4$ is H, $CH_3$, OH, $CHOCH_3$, $(CH_2)_nOH$, $OCH_3$, $O(CH_2)_nCH_3$;

$R_5$ is H, $CH_3$, $C_1$-$C_4$ alkyl, OH, $CHOCH_3$, $(CH_2)_nOH$, $OCH_3$, $O(CH_2)_nCH_3$ or $(CH_2)_nCH_3$; and $R_6$ is H, $CH_3$, $C_1$-$C_4$ alkyl, OH, $CHOCH_3$, $(CH_2)_nOH$, $OCH_3$, $O(CH_2)_nCH_3$;

where n is 0, 1, 2, 3, or 4; and wherein mono-, di-, and tri-carboxylic acids is selected from acetic acid, acetylsalicylic acid, adipic acid, alginic acid, arachidic acid, ascorbic acid, aspartic acid, benzenesulfonic acid, benzoic acid, bisulfic acid, boric acid, butyric acid, camphoric acid, camphorsulfonic acid, capric acid, caproic acid, caprylic acid, carbonic acid, citric acid, cyclopentanepropionic acid, digluconic acid, dodecylsulfic acid, enanthic acid, ethanesulfonic acid, formic acid, fumaric acid, glucoheptanoic acid, gluconic acid, glutamic acid, glutaric acid, glyceric acid, glycerophosphoric acid, glycine, glycolic acid, hemisulfic acid, heptanoic acid, hexanoic acid, hippuric acid, hydrobromic acid, hydrochloric acid, hydroiodic acid, hydroxyethanesulfonic acid, lactic acid, lauric acid, maleic acid, malic acid, malonic acid, mandelic acid, margaric acid, methanesulfonic acid, mucic acid, myristic acid, naphthylanesulfonic acid, naphthylic acid, nicotinic acid, nonadecylic acid, oxalic acid, oxalic acid, palmitic acid, pelargonic, pelargonic acid, pentadecylic acid, phosphoric acid, propionic acid, saccharin, salicylic acid, sorbic acid, stearic acid, succinic acid, sulfuric acid, tartaric acid, thiocyanic acid, thioglycolic acid, thiosulfuric acid, tosylic acid, trichloroacetic acid, tridecylic acid, trifluoroacetic acid, undecylenic acid, undecylic acid, valeric acid;

triose sugars are selected from D- or L-glyceraldehyde;

tetrose sugars are selected from D- or L- erythrose or threose, and their deoxy counterparts;

pentose sugars are selected from D- or L- arabinose, lyxose, ribose, xylose, ribulose, or xylulose, and their deoxy counterparts;

hexose sugars are selected from D- or L- allose, altrose, glucose, mannose, gulose, idose, galactose, talose, psicose, fructose, sorbose, tagatose, and their deoxy counterparts;

and amino acids are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, citrulline, taurine, selenocysteine, pyrrolysine, aminobutyric acid, gama-aminobutryic acid, 3-aminopropanoic acid, dehydroalanine, delta-carboxyglutamic acid, N-formylmethionine. In one embodiment, the tryptamine comprises a compound having the structure of Formula 4A or 4B, (4A)

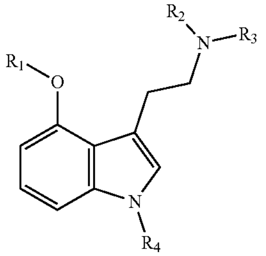

or

-continued (4B)

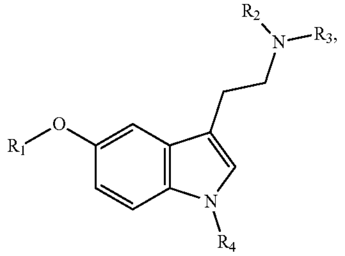

wherein:

$R_1$ is H, OH, COOH, $OCH_3$, $O(CH_2)_nCH_3$, $(CH_2)_nOH$, $(CH_2)_nCOOH$, $—C(O)CH_3$, $(CH_2)_nOC(O)N(R_6)_2$, $—(CH_2)_nC(O)OC(O)OH$, $PO_4$, $P_2O_7$, $P_3O_{10}$, $SO_4$, $S_2O_7$, $S_3O_{10}$, $CHO_3$, a $C_1$-$C_6$ mono- di-, or tri-carboxylic acid, a pentose sugar, a hexose sugar, or an amino acid;

$R_2$ and $R_3$ are independently H, $CH_3$, OH, COOH, $(CH_2)_nCOOH$; $OCH_3$, $O(CH_2)_nCH_3$, $(CH_2)_nOH$, $(CH_2)_nNH_2$; dimethyl amine, pyrrole, pyrazole, imidazole, pyridine, piperdine, pyridine, pyrimidine, indole, purine, quinoline, morpholino, pyran, or furan;

$R_4$ is H, $CH_3$, OH, $(CH_2)_nOH$, $OCH_3$, $O(CH_2)_nCH_3$; and $R_6$ is H, $CH_3$, $C_1$-$C_4$ alkyl, OH, $CHOCH_3$, $(CH_2)_nOH$, $OCH_3$, $O(CH_2)_nCH_3$;

where n is 0, 1, 2, 3, or 4; and wherein mono-, di-, and tri-carboxylic acids is selected from acetic acid, acetylsalicylic acid, adipic acid, alginic acid, arachidic acid, ascorbic acid, aspartic acid, benzenesulfonic acid, benzoic acid, bisulfic acid, boric acid, butyric acid, camphoric acid, camphorsulfonic acid, capric acid, caproic acid, caprylic acid, carbonic acid, citric acid, cyclopentanepropionic acid, digluconic acid, dodecylsulfic acid, enanthic acid, ethanesulfonic acid, formic acid, fumaric acid, glucoheptanoic acid, gluconic acid, glutamic acid, glutaric acid, glyceric acid, glycerophosphoric acid, glycine, glycolic acid, hemisulfic acid, heptanoic acid, hexanoic acid, hippuric acid, hydrobromic acid, hydrochloric acid, hydroiodic acid, hydroxyethanesulfonic acid, lactic acid, lauric acid, maleic acid, malic acid, malonic acid, mandelic acid, margaric acid, methanesulfonic acid, mucic acid, myristic acid, naphthylanesulfonic acid, naphthylic acid, nicotinic acid, nonadecylic acid, oxalic acid, oxalic acid, palmitic acid, pelargonic, pelargonic acid, pentadecylic acid, phosphoric acid, propionic acid, saccharin, salicylic acid, sorbic acid, stearic acid, succinic acid, sulfuric acid, tartaric acid, thiocyanic acid, thioglycolic acid, thiosulfuric acid, tosylic acid, trichloroacetic acid, tridecylic acid, trifluoroacetic acid, undecylenic acid, undecylic acid, valeric acid;

triose sugars are selected from D- or L-glyceraldehyde;

tetrose sugars are selected from D- or L- erythrose or threose, and their deoxy counterparts;

pentose sugars are selected from D- or L- arabinose, lyxose, ribose, xylose, ribulose, or xylulose, and their deoxy counterparts;

hexose sugars are selected from D- or L- allose, altrose, glucose, mannose, gulose, idose, galactose, talose, psicose, fructose, sorbose, tagatose, and their deoxy counterparts;

and amino acids are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, citrulline, taurine, selenocysteine, pyrrolysine, aminobutyric acid, gama-aminobutryic acid, 3-aminopropanoic acid, dehydroalanine, delta-carboxyglutamic acid, N-formylmethionine.

In another embodiment, the tryptamine comprises a compound having the structure of Formula 5A or 5B:

(5A)

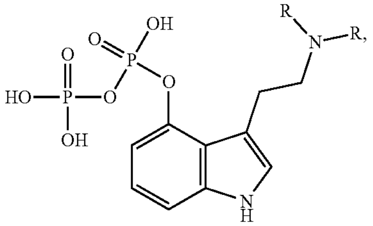

or (5B)

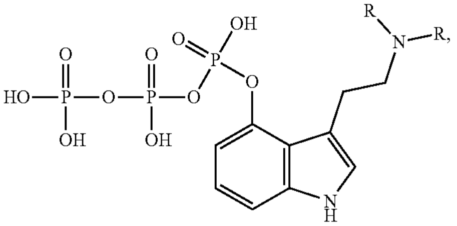

wherein each R is independently H, $CH_3$, $CH_3CH_2$, $CH_3CH_2CH_2$, $(CH_3)_2CH$, $CH_2CH{=}CH$, $OCH_3$, $OC_1$-$C_4$ alkyl, $CH_2OH$, $C_1$-$C_3$ alkyl-OH, COOH, $C_1$-$C_3$ alkyl-COOH, or a pharmaceutically acceptable salt, hydrate, solvate, or tautomer thereof, or a combination thereof.

In another embodiment, the tryptamine comprises a compound having the structure of:

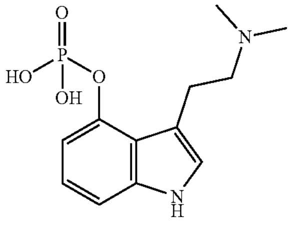

psilocybin

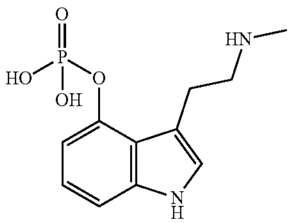

baeocystin

-continued

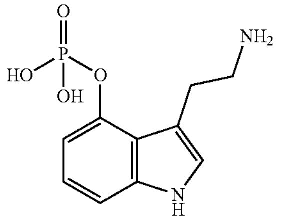

norbaeocystin

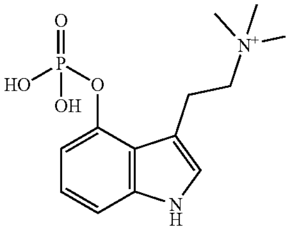

aeruginascin

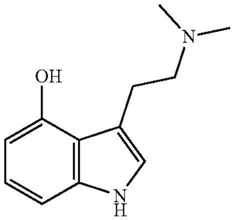

psilocin

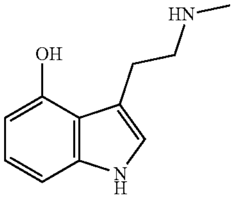

norpsilocin

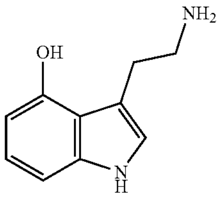

4-hydroxytryptamine

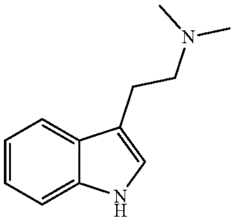

N,N-dimethyltryptamine

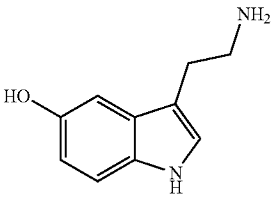

5-hydroxytryptamine (serotonin)

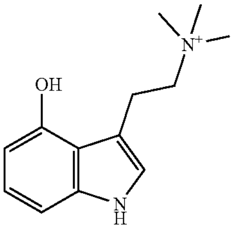

4-hydroxy-N,N,N-trimethyltryptamine

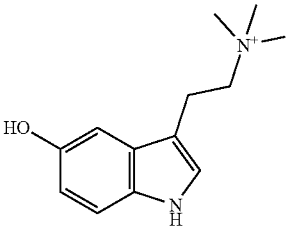

bufotenidine

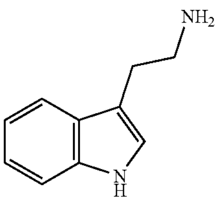

tryptamine

-continued

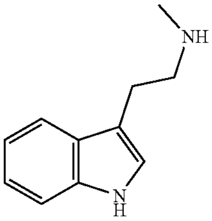

N-methyltryptamine

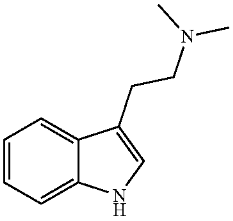

N-ethyltryptamine

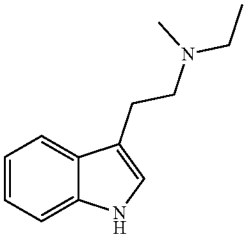

N-methyl-N-ethyltryptamine

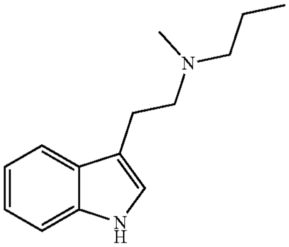

N-methyl-N-propyltryptamine

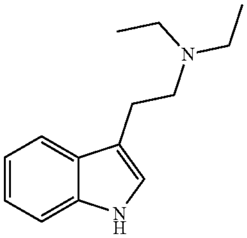

N,N-diethyltryptamine

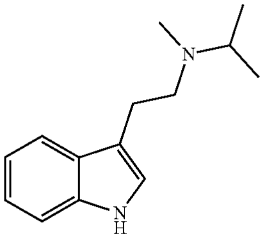

N-methyl-N-isopropyltryptamine

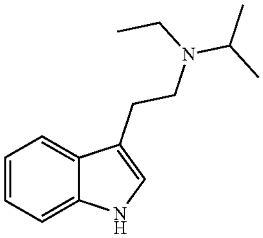

N-ethyl-N-isopropyltryptamine

-continued

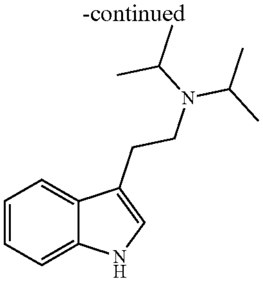

N-N-diisopropyltryptamine

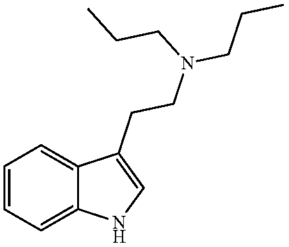

N,N-dipropyltryptamine

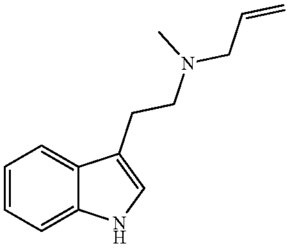

N-methyl-N-allyltryptamine

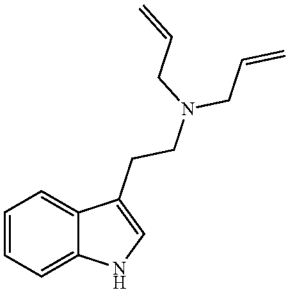

N-N-diallyltryptamine

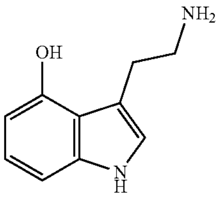

4-hydroxytryptamine

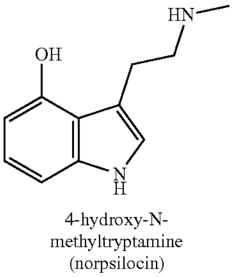

4-hydroxy-N-methyltryptamine (norpsilocin)

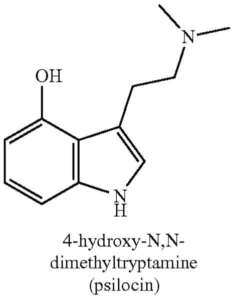

4-hydroxy-N,N-dimethyltryptamine (psilocin)

-continued

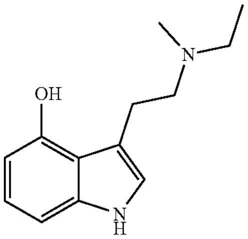

4-hydroxy-N-methyl-N-ethyltryptamine

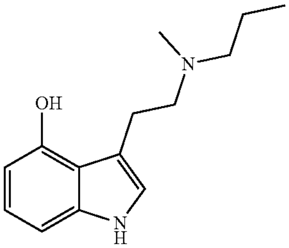

4-hydroxy-N-methyl-N-propyltryptamine

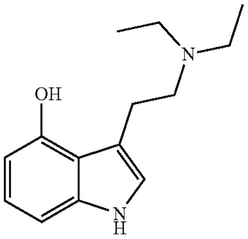

4-hydroxy-N,N-diethyltryptamine

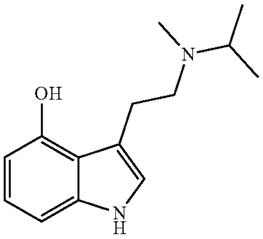

4-hydroxy-N-methyl-N-isopropyltryptamine

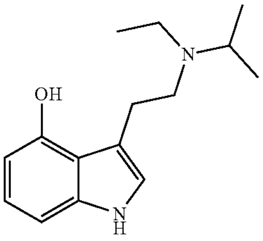

4-hydroxy-N-ethyl-N-isopropyltryptamine

-continued

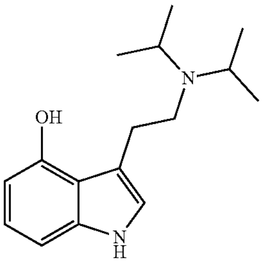

4-hydroxy-N,N-diisopropyltryptamine

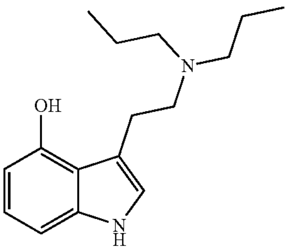

4-hydroxy-N,N-dipropyltryptamine

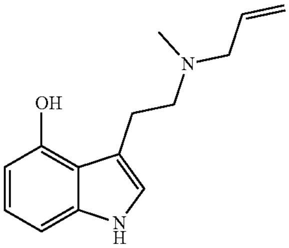

4-hydroxy-N-methyl-N-allyltryptamine

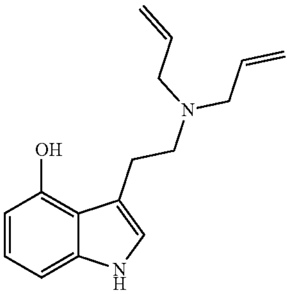

4-hydroxy-N,N-diallyltryptamine

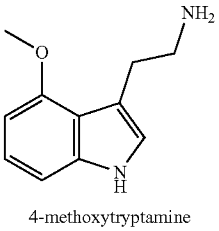

4-methoxytryptamine

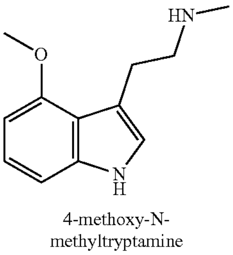

4-methoxy-N-methyltryptamine

-continued

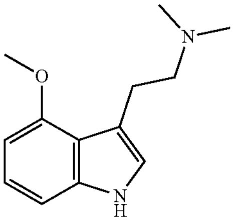

4-methoxy-N,N-dimethyltryptamine

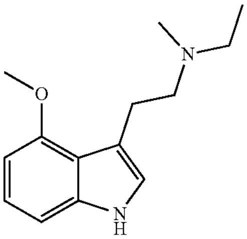

4-methoxy-N-methyl-N-ethyltryptamine

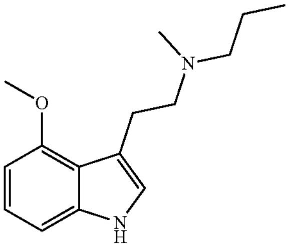

4-methoxy-N-methyl-N-propyltryptamine

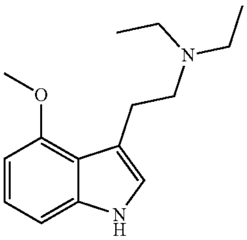

4-methoxy-N,N-diethyltryptamine

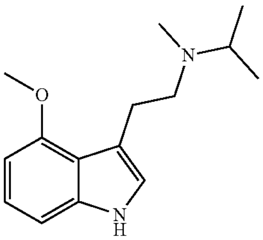

4-methoxy-N-methyl-N-isopropyltryptamine e

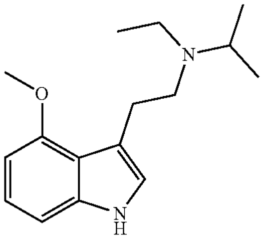

4-methoxy-N-ethyl-N-isopropyltryptamine

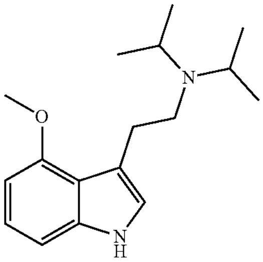

4-methoxy-N,N-diisopropyltryptamine

-continued
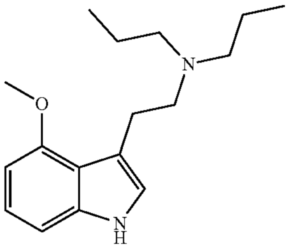
4-methoxy-N,N-dipropyltryptamine
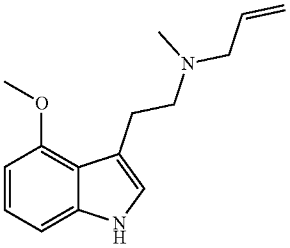
4-methoxy-N-methyl-N-allyltryptamine
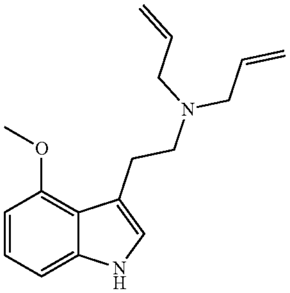
4-methoxy-N,N-diallyltryptamine
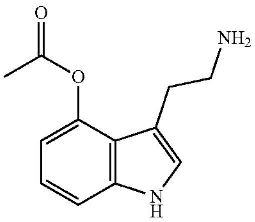
4-acetoxytryptamine
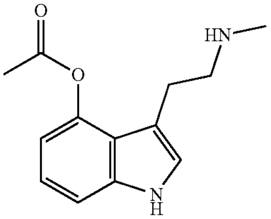
4-acetoxy-N-methyltryptamine
-continued
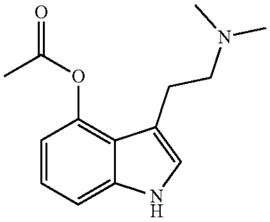
4-acetoxy-N,N-dimethyltryptamine
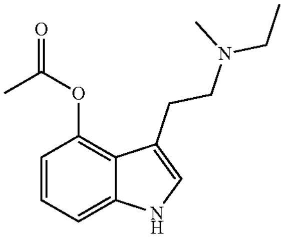
4-acetoxy-N-methyl-N-ethyltryptamine
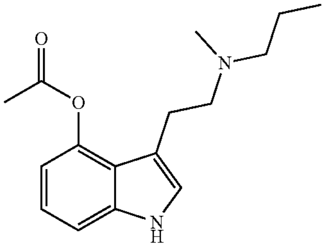
4-acetoxy-N-methyl-N-propyltryptamine
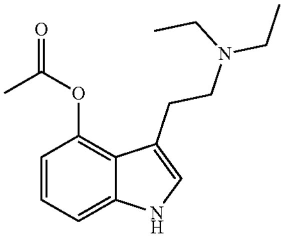
4-acetoxy-N,N-diethyltryptamine
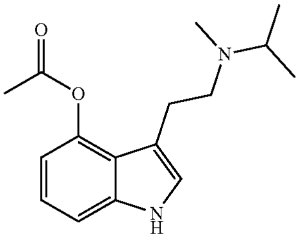
4-acetoxy-N-methyl-N-isopropyltryptamine -continued

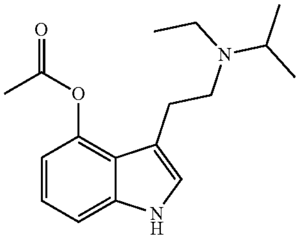

4-methoxy-N-ethyl-N-isopropyltryptamine

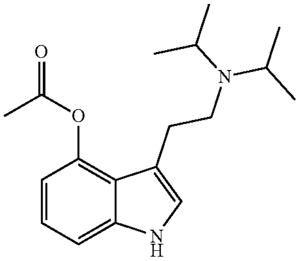

4-acetoxy-N,N-diisopropyltryptamine

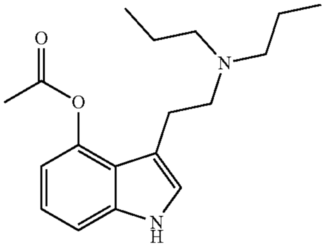

4-acetoxy-N,N-dipropyltryptamine

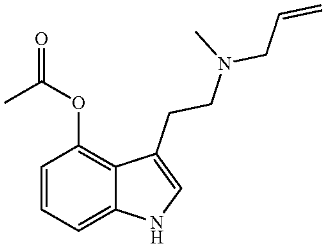

4-acetoxy-N-methyl-N-allyltryptamine

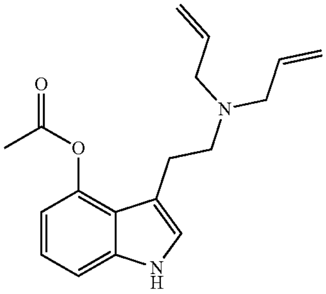

4-acetoxy-N,N-diallyltryptamine

-continued

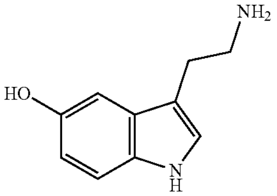

5-hydroxytryptamine

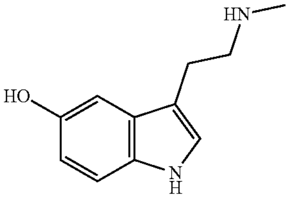

5-hydroxy-N-methyltryptamine

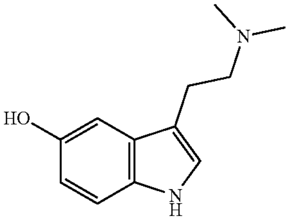

5-hydroxy-N,N-dimethyltryptamine

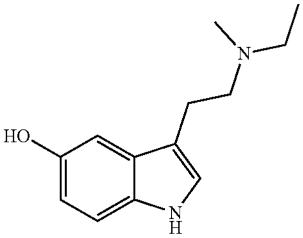

5-hydroxy-N-methyl-N-ethyltryptamine

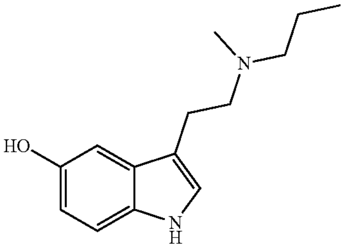

5-hydroxy-N-methyl-N-propyltryptamine

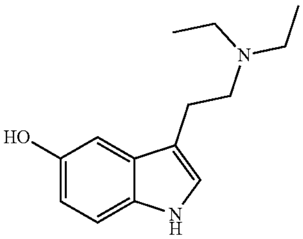

5-hydroxy-N,N-diethyltryptamine

-continued

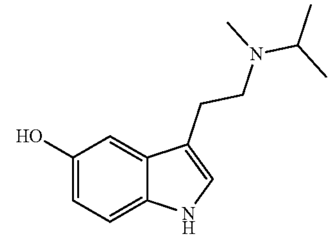

5-hydroxy-N-methyl-N-isopropyltryptamine

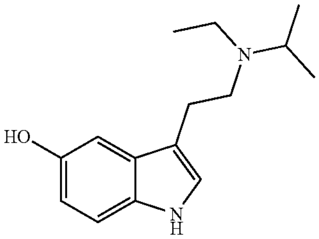

5-hydroxy-N-ethyl-N-isopropyltryptamine

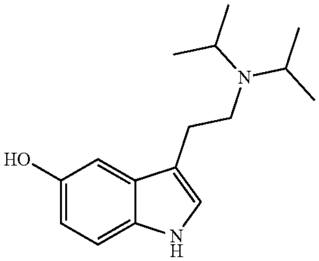

5-hydroxy-N,N-diisopropyltryptamine

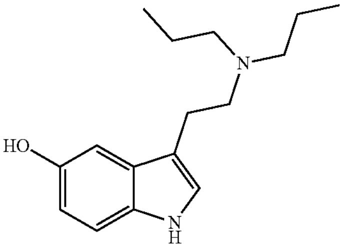

5-hydroxy-N,N-dipropyltryptamine

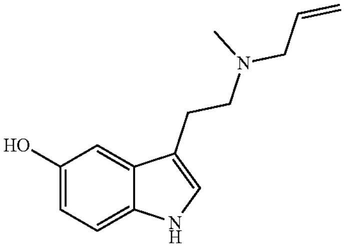

5-hydroxy-N-methyl-N-allyltryptamine

-continued

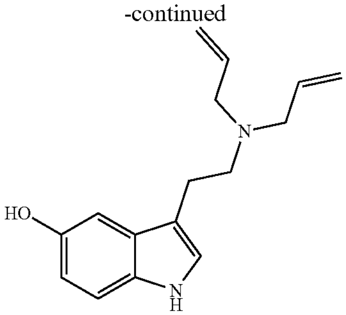

5-hydroxy-N,N-diallyltryptamine

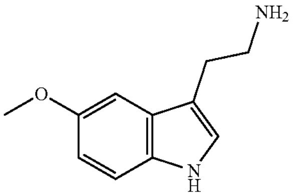

5-methoxytryptamine

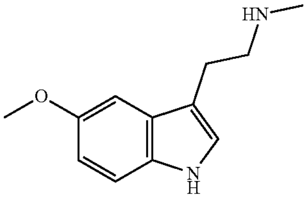

5-methoxy-N-methyltryptamine

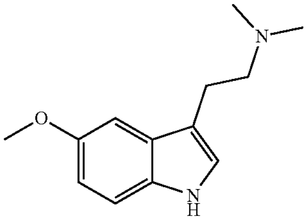

5-methoxy-N,N-dimethyltryptamine

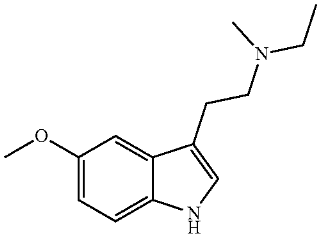

5-methoxy-N-methyl-N-ethyltryptamine

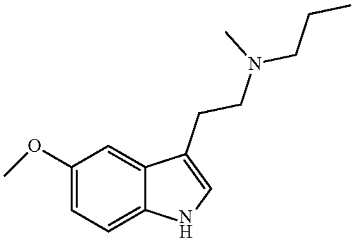

5-methoxy-N-methyl-N-propyltryptamine

-continued

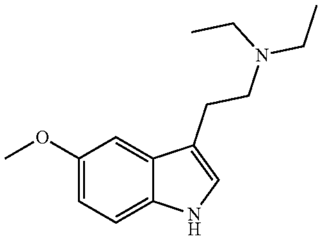

5-methoxy-N,N-diethyltryptamine

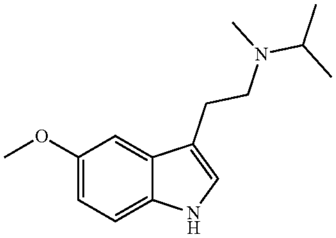

5-methoxy-N-methyl-N isopropyltryptamine

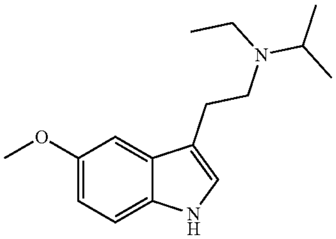

5-methoxy-N-ethyl-N-isopropyltryptamine

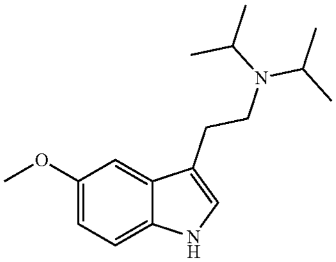

5-methoxy-N,N-diisopropyltryptamine

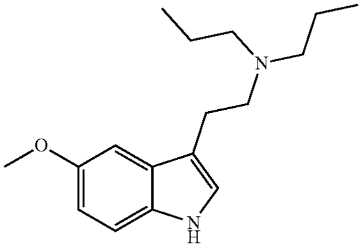

5-methoxy-N,N-dipropyltryptamine

-continued

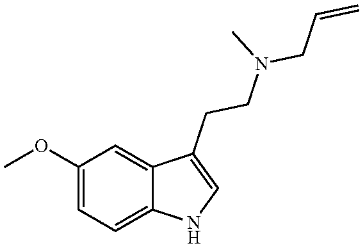

5-methoxy-N,methyl-N-allyltryptamine

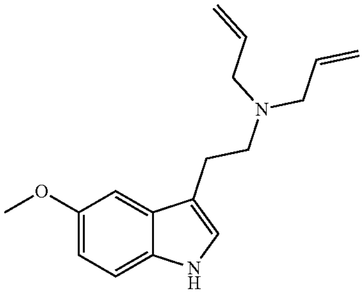

5-methoxy-N,N-diallyltryptamine

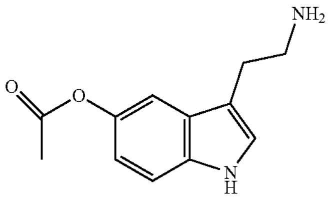

5-acetoxytryptamine

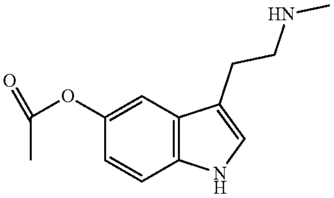

5-acetoxy-N-methyltryptamine

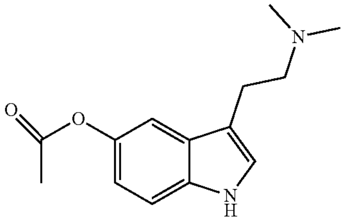

5-acetoxy-N,N-dimethyltryptamine

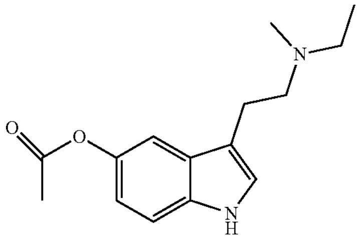

5-acetoxy-N-methyl-N-ethyltryptamine

-continued

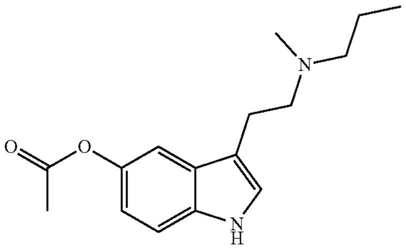

5-acetoxy-N-methyl-N-propyltryptamine

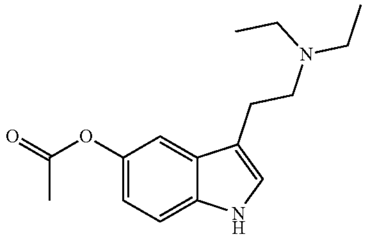

5-acetoxy-N,N-diethyltryptamine

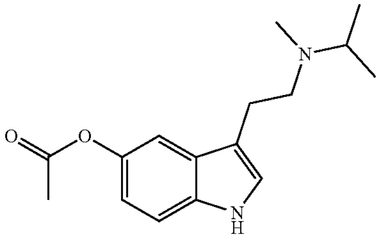

5-acetoxy-N-methyl-N-isopropyltryptamine

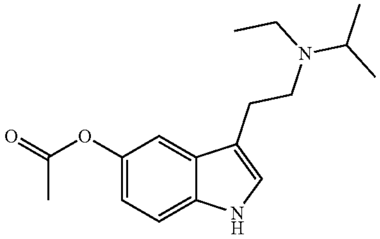

5-methoxy-N-ethyl-N-isopropyltryptamine

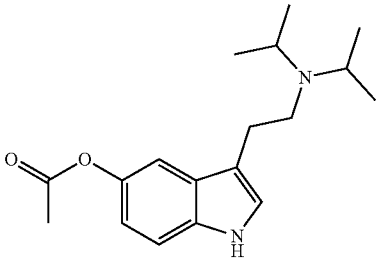

5-acetoxy-N,N-diisopropyltryptamine

-continued

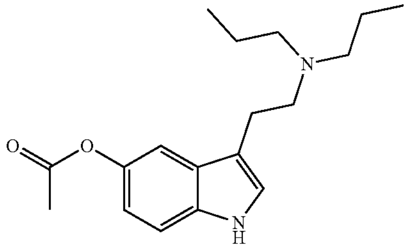

5-acetoxy-N,N-dipropyltryptamine

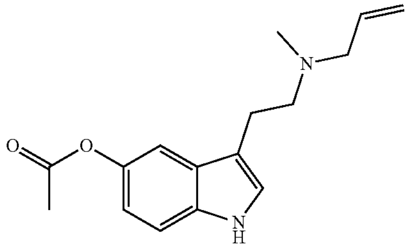

5-acetoxy-N-methyl-N-allyltryptamine

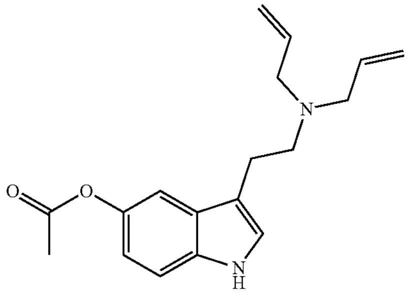

5-acetoxy-N,N-diallyltryptamine

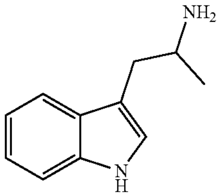

α-methyltryptamine

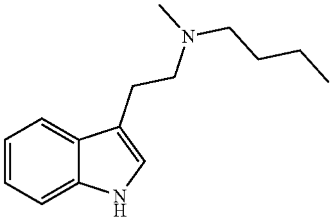

N-methyl-N-butyltryptamine

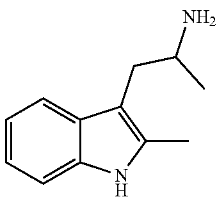

2,α-dimethyltryptamine

-continued

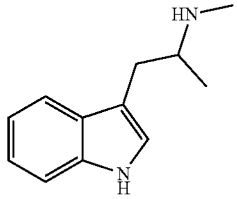

α-N-dimethyltryptamine

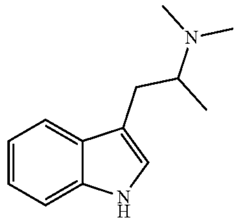

α-methyl-N,N dimethyltryptamine

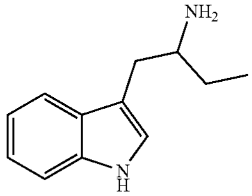

α-ethyltryptamine

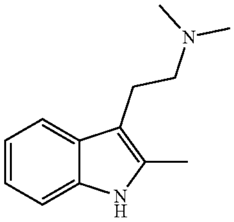

2-methyl-N,N-dimethyltryptamine

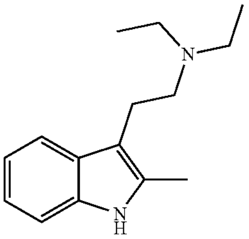

2-methyl-N,N-diethyltryptamine

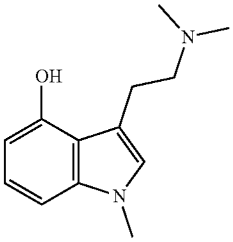

1-methylpsilocon

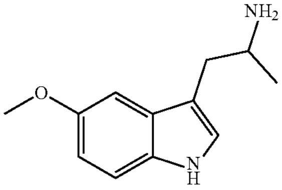

5-methoxy-α-methyltryptamine

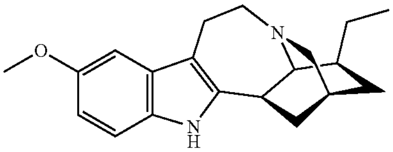

(6R,7S,9S,11 S)-7-ethyl-2-methoxy-6,6a,7,8,9,10,12,13-octahydro-5H-6,9-methanopyrido[1',2':1,2]azepino[4,5-b]indole (ibogaine)

-continued

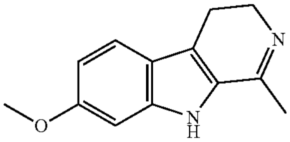

7-methoxy-1-methyl-4,9-dihydro-3H-pyrido[3,4-b]indole (harmaline)

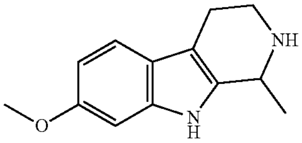

7-methoxy-1-methyl-1,2,3,4-tetrahydro-b-carboline

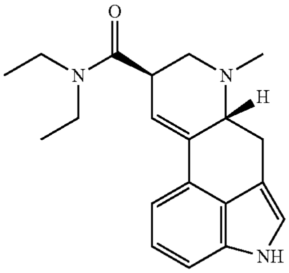

N,N-diethyl-D-lysergamide (LSD)

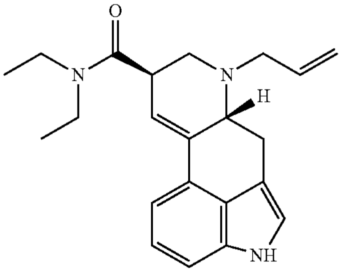

6-ally-N,N-diethyl-norlysergic acid

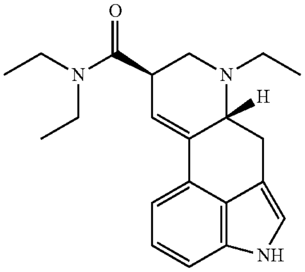

9,10-didehydro-N,N,6-triethylergoline-8b-carboxamide

-continued

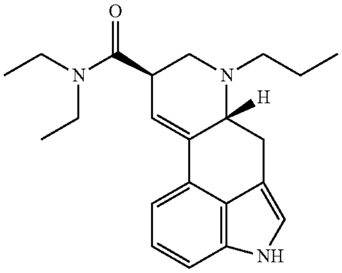

9,10-didehydro-6-propyl-N,N-diethylergoline-8b-carboxamide

In another embodiment, the erinacine comprises Erinacine A, Erinacine B, Erinacine C, Erinacine D, Erinacine E, Erinacine F, Erinacine G, Erinacine H, Erinacine I, Erinacine J, Erinacine K, Erinacine P, Erinacine Q, Erinacine R, Erinacol, other Erinacines or a pharmaceutically acceptable salt, hydrate, solvate, prodrug, stereoisomer, or tautomer thereof, or a combination thereof.

In another embodiment, the erinacine comprises a compound having the structure of:

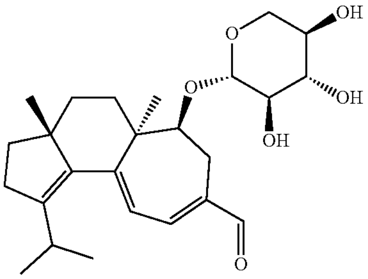

Erinacine A

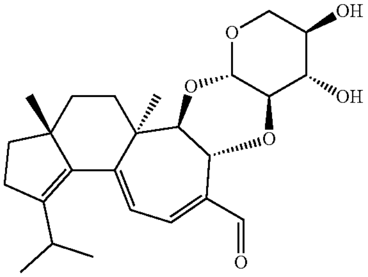

Erinacine B

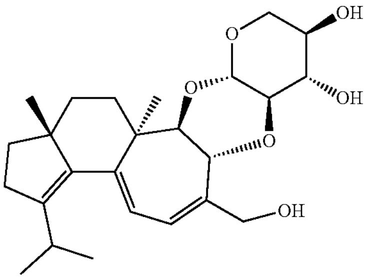

Erinacine C

-continued

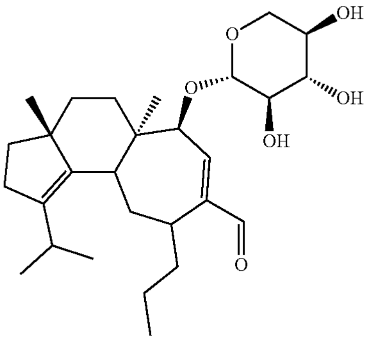

Erinacine D

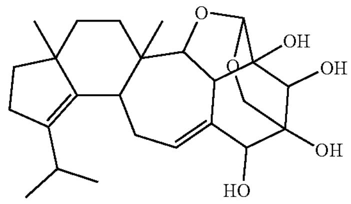

Erinacine E

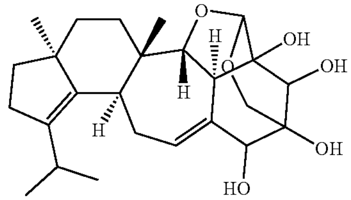

Erinacine F

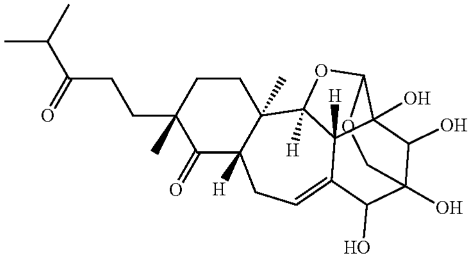

Erinacine G

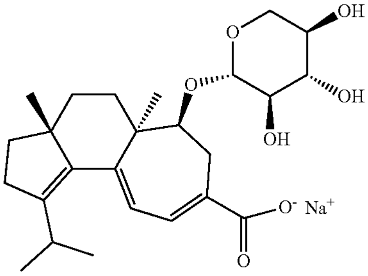

Erinacine H

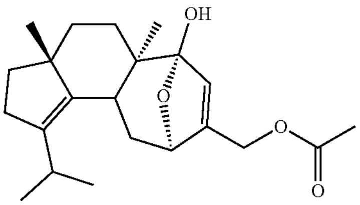

Erinacine I

-continued

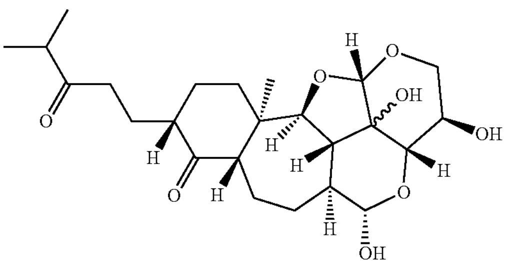

Erinacine J

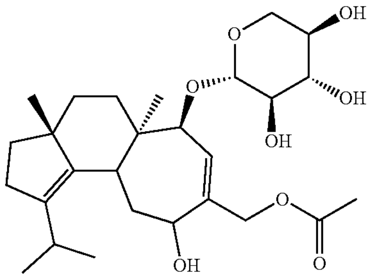

Erinacine K

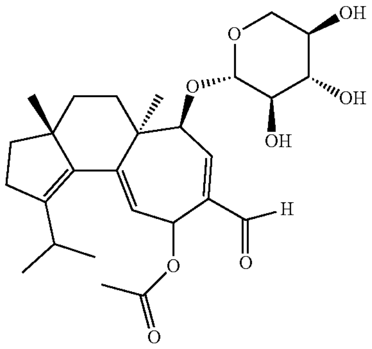

Erinacine P

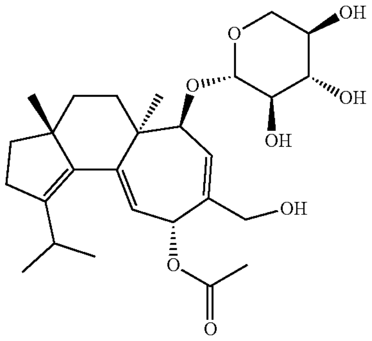

Erinacine Q

-continued

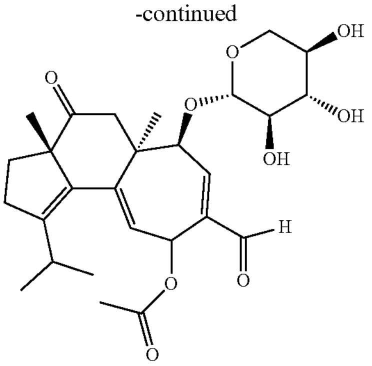

Erinacine R

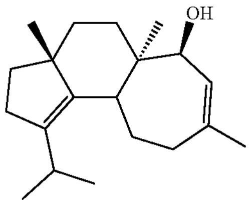

Erinacol

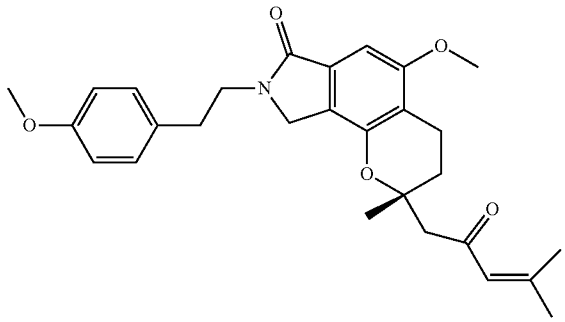

Erinacerin O

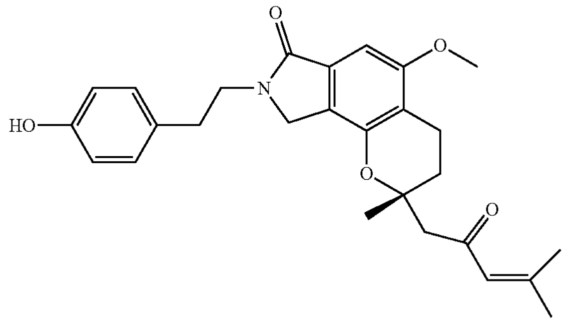

Erinacerin P

In another embodiment, the hericenone comprises Hericenone A, Hericenone B, Hericenone C, Hericenone D, Hericenone E, Hericenone F, Hericenone G, Hericenone H, other hericenones, or a pharmaceutically acceptable salt, hydrate, solvate, prodrug, stereoisomer, or tautomer thereof, or a combination thereof.

In another embodiment, the hericenone comprises a compound having the structure of:

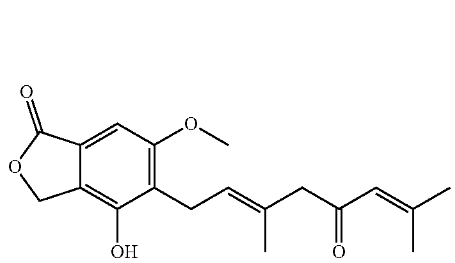

Hericenone A

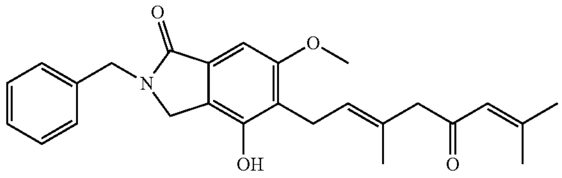

Hericenone B

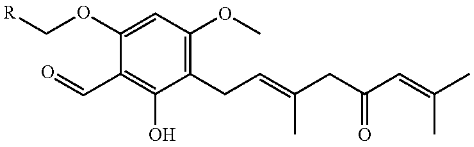

Hericenone C, R = palmitoyl, —$OC(CH_2)_{14}CH_3$
Hericenone D, R = stearoyl, —$OC(CH_2)_{16}CH_3$
Hericenone, E, R = linoleoyl, 18:2 cis-9, 12

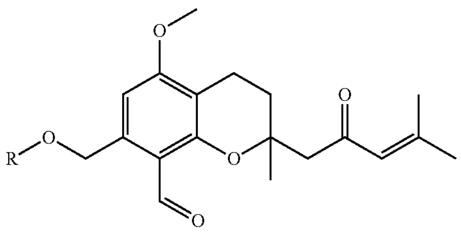

Hericenone F, R = palmitoyl, —$OC(CH_2)_{14}CH_3$
Hericenone G, R = stearoyl, —$OC(CH_2)_{16}CH_3$
Hericenone, H, R = linoleoyl, 18:2 cis-9, 12

In another embodiment, the active compound is a compound isolated and identified in an extract from Hericium *erinaceus*.

In another embodiment, the cannabinoid comprises Δ8-tetrahydrocannabinol (THC), Δ9-tetrahydrocannabinol, tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), other cannabinoids, or a pharmaceutically acceptable salt, hydrate, solvate, prodrug, stereoisomer, or tautomer thereof, or a combination thereof.

In another embodiment, the cannabinoid comprises a compound having the structure of:

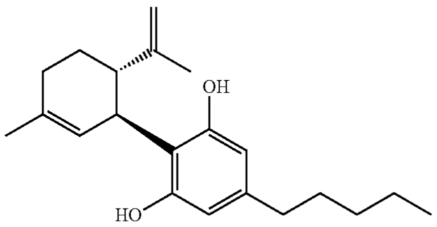

Cannabidiol

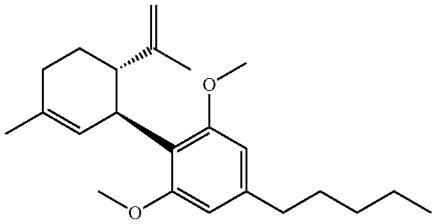

Cannabidiol-2′,6′-dimethyl ether

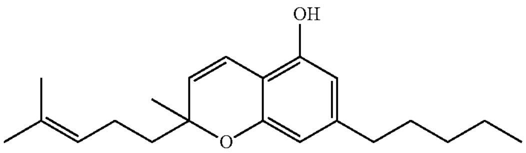

Cannabichromene

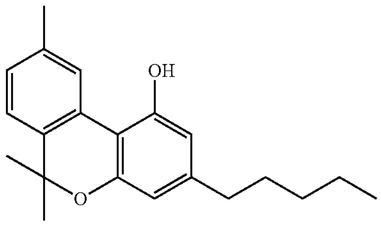

Cannabinol

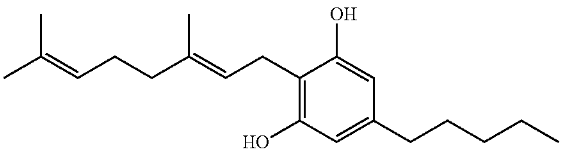

Cannabigerol

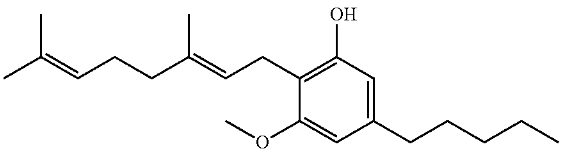

Cannabigerol monomethylether

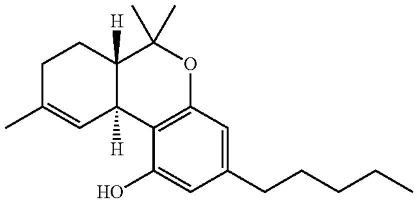

Δ-9-tetrahydrocannabinoll (THC)

-continued

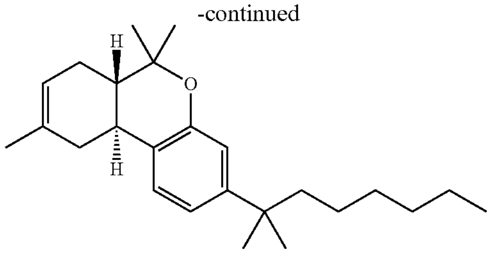

Δ-8-tetrahydrocannabinoll

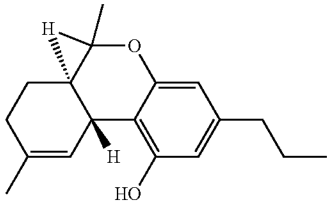

Tetrahydrocannabivarin

In another embodiment, the compositions described herein comprises one or more natural products such as aliphatic natural products, alkaloids, amino acids, anthranilic acid alkaloids, apiole, (+)-aromanderndrene, asarone, aurones, benzofuranoids, benzofurans, benzophenones, benzopyranoids, benzopyrans, benztropolones, cis-α-bergamotene, trans-α-bergamotene, α-bisabolol, borneol, γ-cadinene, caffeic acid, camphor, carbohydrates, carotenoids, 3-carene, β-carbolines, trans-β-caryophyllene, catechins, chalcones, chavicol, chavicols, chromones, cineol, cinnamic acid, cinnamic aldehydes, cinnamic monolignols, conferyl alcohol, coniferyl alcohol, cordysinin, coumarins, coumaric acid, coumaryl alcohol, cutin, depsides, depsidones, dillapiole, diterpenes, diterpenoids, γ-elemene, elemicin, eleutherosides, esterterpenoids, estragole, eudesman-3,7(11)-diene, β-eudesmol, γ-eudesmol, eugenol, trans-β-farnesene, ferulic acid, haramane, harmine, norharmine, harmol, α-humuline, β-fenchol, 5-hydroxyferulic acid, flavonoids, glycopeptides, hydroxycinnamic acids, hydroxylated fatty acids, imidazole alkaloids, isoflavonoids, isoquinoline alkaloids, β-lactams, lignans, limonoids, β-limonene, (−)-linalool, lipids, lysine alkaloids, meroterpenoids, methyl eugenol, miscellaneous terpenoids, monoterpenoid indole alkaloids, monoterpenoids, myrcene, myristicin, nerolidol, nicotinic acid alkaloids, cis-ocimene, 1-octanol, ornithine alkaloids, otenoids, oxazole alkaloids, oxygen heterocycles, peptides, phellanderene, phenolics, phenylalanine alkaloids, phenylpropanoids, phenylpropanoids, phenylpropenes, perlolyrine, pinene, polycyclic aromatic natural products, polyketide alkaloids, polyketides, polypyrroles, ptteridines, purines, putrescine alkaloids, pyrazine alkaloids, pyrimidines, pyrrole alkaloids, quassinoids, quinonemethides, quinones, quinoxaline alkaloids, resveratrol, trans-resveratrol, cis-sabinene hydrate, safrole, γ-selinene, semiochemicals, septide alkaloids, sesquiterpenes, sesquiterpenoids, simple aromatic natural products, sinapic acid, sinapyl alcohols, spermidine alkaloids, spermine alkaloids, sporopollenin, steroidal alkaloids, steroids, sterols, stilbenes, stilbenoids, suberin, tannins, terpenoid alkaloids, terpenoids, γ-terpinene, α-terpineol, terpinolene, tetraterpenoids, thiazole alkaloids, triterpenes, triterpenoids, tryptophan alkaloids, tyrosine alkaloids, umbelliferone, xanthones, or a pharmaceutically acceptable salt, hydrate, solvate, prodrug, stereoisomer, or tautomer thereof, or a combination thereof.

In another embodiment, the compositions described herein comprises a phenethylamine or an amphetamine compound selected from: α-ethyl-3,4,5-trimethoxy-phenethylamine (AEM), 4-allyloxy-3,5-dimethoxy-phenethylamine (AL), 4-methylthio-2,5-dimethoxy-amphetamine (ALEPH), 4-ethylthio-2,5-dimethoxy-amphetamine (ALEPH-2), 4-isopropylthio-2,5-dimethoxy-amphetamine (ALEPH-4), 4-phenylthio-2,5-dimethoxy-amphetamine (ALEPH-6), 4-propylthio-2,5-dimethoxy-amphetamine (ALEPH-7), 2,5-dimethoxy-α-ethyl-4-methyl-phenethylamine (ARIADNE), 3,4-diethoxy-5-methoxy-phenethylamine (ASB), 4-butoxy-3,5-dimethoxy-phenethylamine (B), 2,5-dimethoxy-4,N-dimethyl-amphetamine (BEATRICE), 2,5-bismethylthio-4-methyl-amphetamine (BIS-TOM), 4-bromo-2,5,β-trimethoxy-phenethylamine (BOB), 2,5,β-trimethoxy-4-methyl-phenethylamine (BOD), β-methoxy-3,4-methylenedioxy-phenethylamine (BOH), 2,5-dimethoxy-β-hydroxy-4-methyl-phenethylamine (BOHD), 3,4,5,β-tetramethoxy-phenethylamine (BOM), 4-bromo-3,5-dimethoxy-amphetamine (4-Br-3,5-DMA), 2-bromo-4,5-methylenedioxy-amphetamine (2-Br-4,5-MDA), 4-bromo-2,5-dimethoxy-phenethylamine (2C-B), 4-benzyloxy-3,5-dimethoxy-amphetamine (3C-BZ), 4-chloro-2,5-dimethoxy-phenethylamine (2C-C), 4-methyl-2,5-dimethoxy-phenethylamine (2C-D), 4-ethyl-2,5-dimethoxy-phenethylamine (2C-E), 4-ethoxy-3,5-dimethoxy-amphetamine (3C-E), 4-fluoro-2,5-dimethoxy-phenethylamine (2C-F), 3,4-dimethyl-2,5-dimethoxy-phenethylamine (2C-G), 3,4-trimethylene-2,5-dimethoxy-phenethylamine (2C-G-3), 3,4-tetramethylene-2,5-dimethoxy-phenethylamine (2C-G-4), 3,4-norbornyl-2,5-dimethoxy-phenethylamine (2C-G-5), 1,4-dimethoxynaphthyl-2-ethylamine (2C-G-N), 2,5-dimethoxy-phenethylamine (2C-H), 4-iodo-2,5-dimethoxy-phenethylamine (2C-I), 4-nitro-2,5-dimethoxy-phenethylamine (2C-N), 4-isopropoxy-2,5-dimethoxy-phenethylamine (2C-O-4), 4-propyl-2,5-dimethoxy-phenethylamine (2C-P), 4-cyclopropylmethoxy-3,5-dimethoxy-phenethylamine (CPM), 4-methylseleno-2,5-dimethoxy-phenethylamine (2C-SE), 4-methylthio-2,5-dimethoxy-phenethylamine (2C-T), 4-ethylthio-2,5-dimethoxy-phenethylamine (2C-T-2), 4-isopropylthio-2,5-dimethoxy-phenethylamine (2C-T-4), 4-isopropylthio-2,6-dimethoxy-phenethylamine (psi-2C-T-4), 4-propylthio-2,5-dimethoxy-phenethylamine (2C-T-7), 4-cyclopropylmethylthio-2,5-dimethoxy-phenethylamine (2C-T-8), 4-(t)-butylthio-2,5-dimethoxy-phenethylamine (2C-T-9), 4-(2-methoxyethylthio)-2,5-dimethoxy-phenethylamine (2C-T-13), 4-cyclopropylthio-2,5-dimethoxy-phenethylamine (2C-T-15), 4-(s)-butylthio-2,5-dimethoxy-phenethylamine (2C-T-17), 4-(2-fluoroethylthio)-2,5-dimethoxy-phenethylamine (2C-T-21), 4 -trideuteromethyl-3,5-dimethoxy-phenethylamine (4-D), β,β-dideutero-3,4,5-trimethoxy-phenethylamine (β-D), 4-methyl-3,5-dimethoxy-phenethylamine (DESOXY), 2,4-dimethoxy-amphetamine (2,4-DMA), 2,5-dimethoxy-amphetamine (2,5-DMA), 3,4-dimethoxy-amphetamine (3,4-DMA), 2-(2,5-dimethoxy-4-methylphenyl)-cyclopropylamine (DMCPA), 3,4-dimethoxy-β-hydroxy-phenethylamine (DME), 2,5-dimethoxy-3,4-methylenedioxy-amphetamine (DMMDA), 2,3-dimethoxy-4,5-methylenedioxy-amphetamine (DMMDA-2), 3,4-dimethoxy-phenethylamine (DMPEA), 4-amyl-2,5-dimethoxy-amphetamine (DOAM), 4-bromo-2,5-dimethoxy-amphetamine (DOB), 4-butyl-2,5-dimethoxy-amphetamine (DOBU), 4-chloro-2,5-dimethoxy-amphetamine (DOC), 4-(2-fluoroethyl)-2,5-dimethoxy-amphetamine (DOEF), 4-ethyl-2,5-dimethoxy-amphetamine (DOET), 4-iodo-2,5-dimethoxy-amphetamine (DOI), 4-methyl-2,5-dimethoxy-amphetamine (DOM (STP)), 4-methyl-2,6-dimethoxy-amphetamine (psi-DOM), 4-nitro-2,5-dimethoxy-amphetamine (DON), 4-propyl-2,5-dimethoxy-amphetamine (DOPR), 4-ethoxy-3,5-dimethoxy-phenethylamine (E), 2,4,5-triethoxy-amphetamine (EEE), 2,4-diethoxy-5-methoxy-amphetamine (EEM), 2,5-diethoxy-4-methoxy-amphetamine (EME), 2-ethoxy-4,5-dimethoxy-amphetamine (EMM), N,α-diethyl-3,4-methylenedioxy-phenethylamine (ETHYL-J), N-ethyl-α-propyl-3,4-methylenedioxy-phenethylamine (ETHYL-K), benzofuran-2-methyl-5-methoxy-6-(2-aminopropane) (F-2), benzofuran-2,2-dimethyl-5-methoxy-6-(2-aminopropane) (F-22), N-hydroxy-N-methyl-3,4-methylenedioxy-amphetamine (FLEA), 3,4-trimethylene-2,5-dimethoxy-amphetamine (G-3), 3,4-tetramethylene-2,5-dimethoxy-amphetamine (G-4), 3,4-norbornyl-2,5-dimethoxy-amphetamine (G-5), 3,4-dimethyl-2,5-dimethoxy-amphetamine (GANESHA), 1,4-dimethoxynaphthyl-2-isopropylamine (G-N), 2,5-dimethoxy-N-hydroxy-4-ethylthio-phenethylamine (HOT-2), 2,5-dimethoxy-N-hydroxy-4-(n)-propylthio-phenethylamine (HOT-7), 2,5-dimethoxy-N-hydroxy-4-(s)-butylthio-phenethylamine (HOT-17), 2,5-dimethoxy-N,N-dimethyl-4-iodo-amphetamine (IDNNA), 2,3,4-trimethoxy-phenethylamine (IM), 3,5-dimethoxy-4-isopropoxy-phenethylamine (IP), 5-ethoxy-2-methoxy-4-methyl-amphetamine (IRIS), α-ethyl-3,4-methylenedioxy-phenethylamine (J), 3-methoxy-4,5-methylenedioxy-phenethylamine (LOPHOPHINE), 3,4,5-trimethoxy-phenethylamine (M), 4-methoxy-amphetamine (4-MA), 2,N-dimethyl-4,5-methylenedioxy-amphetamine (MADAM-6), 3,5-dimethoxy-4-methallyloxy-phenethylamine (MAL), 3,4-methylenedioxy-amphetamine (MDA), N-allyl-3,4-methylenedioxy-amphetamine (MDAL), N-butyl-3,4-methylenedioxy-amphetamine (MDBU), N-benzyl-3,4-methylenedioxy-amphetamine (MDBZ), N-Cyclopropylmethyl-3,4-methylenedioxy-amphetamine (MDCPM), N,N-dimethyl-3,4-methylenedioxy-amphetamine (MDDM), N-ethyl-3,4-methylenedioxy-amphetamine (MDE), N-(2-hydroxyethyl)-3,4-methylenedioxy-amphetamine (MDHOET), N-isopropyl-3,4-methylenedioxy-amphetamine (MDIP), N-methyl-3,4 -methylenedioxy-amphetamine (MDMA), N-methyl-3,4-ethylenedioxy-amphetamine (MDMC), N-methoxy-3,4-methylenedioxy-amphetamine (MDMEO), N-(2-methoxyethyl)-3,4-methylenedioxy-amphetamine (MDMEOET), α,α,N-trimethyl-3,4-methylenedioxy-phenethylamine (MDMP), N-hydroxy-3,4-methylenedioxy-amphetamine (MDOH), 3,4-methylenedioxy-phenethylamine (MDPEA), α,α-dimethyl-3,4-methylenedioxy-phenethylamine (MDPH), N-propargyl-3,4-methylenedioxy-amphetamine (MDPL), N-propyl-3,4-methylenedioxy-amphetamine (MDPR), 3,4-dimethoxy-5-ethoxy-phenethylamine (ME), 3-methoxy-4,5-ethylenedioxy-amphetamine (MEDA), 2-methoxy-4,5-diethoxy-amphetamine (MEE), 2,5-dimethoxy-4-ethoxy-amphetamine (MEM), 3-methoxy-4-ethoxy-phenethylamine (MEPEA), 5-bromo-2,4-dimethoxy-amphetamine (META-DOB), 5-methylthio-2,4-dimethoxy-amphetamine (META-DOT), N-methyl-2,5-dimethoxy-amphetamine (METHYL-DMA), 4-bromo-2,5-dimethoxy-N-methyl-amphetamine (METHYL-DOB), N-methyl-α-ethyl-3,4-methylenedioxy-phenethylamine (METHYL-J), N-methyl-α-propyl-3,4-methylenedioxy-phenethylamine (METHYL-K), N-methyl-4-methoxy-amphetamine (METHYL-MA), N-methyl-2-methoxy-4,5-methylenedioxy-amphetamine (METHYL-MMDA-2), 3-methoxy-4,5-methylenedioxy-amphetamine (MMDA), 2-methoxy-4,5-methylenedioxy-amphetamine (MMDA-2), 2-methoxy-3,4-methylenedioxy-amphetamine (MMDA-3a), 4-methoxy-2,3-methylenedioxy-amphetamine (MMDA-3b), 2,4-dimethoxy-5-ethoxy-amphetamine (MME), 3,4-dimethoxy-5-propoxy-phenethylamine (MP), 2,5-dimethoxy-4-propoxy-amphetamine (MPM), 2-methylthio-4,5-dimethoxy-amphetamine (ORTHO-DOT), 3,5-dimethoxy-4-propoxy-phenethylamine (P), 3,5-dimethoxy-4-phenethyloxy-phenethylamine (PE), phenethylamine (PEA), 4-propynyloxy-3,5-dimethoxy-phenethylamine (PROPYNYL), 3,5-diethoxy-4-methoxy-phenethylamine (SB), 2,3,4,5-Tetramethoxy-amphetamine (TA), 4-ethoxy-3-ethylthio-5-methoxy-phenethylamine (3-TASB), 3-ethoxy-4-ethylthio-5-methoxy-phenethylamine (4-TASB), 3,4-diethoxy-5-methylthio-phenethylamine (5-TASB), 4-thiobutoxy-3,5-dimethoxy-phenethylamine (TB), 4-ethoxy-5-methoxy-3-methylthio-phenethylamine (3-TE), 3,5-dimethoxy-4-ethylthio-phenethylamine (4-TE), 2-methylthio-3,4-dimethoxy-phenethylamine (2-TIM), 3-methylthio-2,4-dimethoxy-phenethylamine (3-TIM), 4-methylthio-2,3-dimethoxy-phenethylamine (4-TIM), 3-methylthio-4,5-dimethoxy-phenethylamine (3-TM), 4-methylthio-3,5-dimethoxy-phenethylamine (4-TM), 3,4,5-trimethoxy-amphetamine (TMA), 2,4,5-trimethoxy-amphetamine (TMA-2), 2,3,4-trimethoxy-amphetamine (TMA-3), 2,3,5-trimethoxy-amphetamine (TMA-4), 2,3,6-trimethoxy-amphetamine (TMA-5), 2,4,6-trimethoxy-amphetamine (TMA-6), 4,5-dimethoxy-3-ethylthio-phenethylamine (3-TME), 3-ethoxy-5-methoxy-4-methylthio-phenethylamine (4-TME), 3-ethoxy-4-methoxy-5-methylthio-phenethylamine (5-TME), 2-methylthio-3,4-methylenedioxy-amphetamine (2T-MMDA-3a), 4,5-thiomethyleneoxy-2-methoxy-amphetamine (4T-MMDA-2), 2,4,5-trimethoxy-phenethylamine (TMPEA), 4-ethyl-5-methoxy-2-methylthio-amphetamine (2-TOET), 4-ethyl-2-methoxy-5-methylthio-amphetamine (5-TOET), 5-methoxy-4-methyl-2-methylthio-amphetamine (2-TOM), 2-methoxy-4-methyl-5-methylthio-amphetamine (5-TOM), 2-methoxy-4-methyl-5-methylsulfinyl-amphetamine (TOMSO), 4-propylthio-3,5-dimethoxy-phenethylamine (TP), 3,4,5-triethoxy-phenethylamine (TRIS), 3-ethoxy-5-ethylthio-4-methoxy-phenethylamine (3-TSB), 3,5-diethoxy-4-methylthio-phenethylamine (4-TSB), 4,5-diethoxy-3-ethylthio-phenethylamine (3-T-TRIS), 3,5-diethoxy-4-ethylthio-phenethylamine (4-T-TRIS), (R)-2,5-dimethoxy-4-iodoamphetamine, or a pharmaceutically acceptable salt, hydrate, solvate, prodrug, stereoisomer, or tautomer thereof, or a combination thereof. See Shulgin and Shulgin, *PIHKAL: A Chemical Love Story*, Transform Press (1994), which is incorporated by reference herein for the specific teachings thereof. In some embodiments, the amphetamine may be (R)-2,5-dimethoxy-4-iodoamphetamine or a pharmaceutically acceptable salt, hydrate, solvate, prodrug, stereoisomer, or tautomer thereof. (R)-2,5-dimethoxy-4-iodo-amphetamine (i.e., 2C-H) is structurally similar to the popular psychedelic drug 2C-B (which is similar to ecstasy and MDMA), but it does not itself have any psychoactive effects. It was found to activate the 5-$HT_{2A}$receptor and prevent and reverse inflammation in the lungs. Flanagan and Nichols, Int. Review of Psychiatry, 30(4): 363-375 (2018). In another embodiment, the amphetamine comprises (R)-2,5-dimethoxy-4-iodoamphetamine, having the structure:

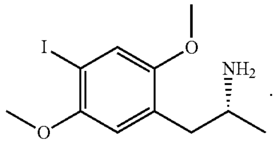

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, preferences, or steps described herein. The exemplary compositions, formulations, and methods described herein may omit any component or step described herein, substitute any component or step described herein, or include any component or step described elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing description discloses exemplary embodiments. All patents and publications cited herein are incorporated by reference herein for the specific teachings thereof.

EXAMPLES

Example 1

Hericium *erinaceus* Extracts

Extracts were prepared from Hericium *erinaceus* mycelium or fruiting bodies colonized on rice or rice and oat hull fiber for various time periods.

H. *erinaceus* was cultivated, frozen and ground and extracted in water for 2 h at room temperature. The extract was filtered through Whatman filter via gravity. The filtrate was lyophilized to dryness.

Ethanol extracts were made from the same H. *erinaceus* mycelium. The mycelium was frozen, but not ground, and extracted in 70% ethanol for 1 week at room temperature. The extract was filtered through an 80-mesh sieve and lyophilized to dryness.

A portion of the ethanol extract was rotovapped to dryness and the residue resuspended in 1:1 water:ethyl acetate. The water/ethyl acetate extract was washed 3 times with ethyl acetate, the combined organic fractions dried over $MgSO_4$, filtered, rotovapped, and then lyophilized.

Example 2

Experiments were conducted to evaluate the neurotrophic effects of several purified tryptamines, H. erinaceum extracts, and the tryptamines combined with selected extracts of H. erinaceum. The tryptamines, baeocystin, norbaeocystin, and norpsilocin, were evaluated at final concentrations of 0.3 μg/mL, 1 μg/mL, 3 μg/mL, and 10 μg/mL. The experiments analyzed the H. erinaceum growth medium (rice or rice and oat hull fiber), the days of cultivation, the extract solvent (water, ethanol, or ethyl acetate), and the final concentration of the extract (31.3 μg/mL, 62.5 μg/mL, 125 μg/mL or 250 μg/mL). Finally, combinations of the three tryptamines and representative H. erinaceum extracts were combined and evaluated.

The test compositions are shown in Table 4.

TABLE 4

| Test Compositions |
|---|
| He mycelium, rice 12 d, $H_2O$ 31.3 μg/mL |
| He mycelium, rice 12 d, $H_2O$ 62.5 μg/mL |
| He mycelium, rice 12 d, $H_2O$ 125 μg/mL |
| He mycelium, rice 12 d, $H_2O$ 250 μg/mL |
| He mycelium, rice 12 d, EtOH 31.3 μg/mL |
| He mycelium, rice 12 d, EtOH 62.5 μg/mL |
| He mycelium, rice 12 d, EtOH 125 μg/mL |
| He mycelium, rice 12 d, EtOH 250 μg/mL |
| He mycelium, rice 12 d, EtOAc 31.3 μg/mL |
| He mycelium, rice 12 d, EtOAc 62.5 μg/mL |
| He mycelium, rice 12 d, EtOAc 125 μg/mL |
| He mycelium, rice 12 d, EtOAc 250 μg/mL |
| He mycelium, rice, oat hull 21 d, $H_2O$ 31.3 μg/mL |
| He mycelium, rice, oat hull 21 d, $H_2O$ 62.5 μg/mL |
| He mycelium, rice, oat hull 21 d, $H_2O$ 125 μg/mL |
| He mycelium, rice, oat hull 21 d, $H_2O$ 250 μg/mL |
| He mycelium, rice, oat hull 21 d, EtOH 31.3 μg/mL |
| He mycelium, rice, oat hull 21 d, EtOH 62.5 μg/mL |
| He mycelium, rice, oat hull 21 d, EtOH 125 μg/mL |
| He mycelium, rice, oat hull 21 d, EtOH 250 μg/mL |
| He mycelium, rice, oat hull 21 d, EtOAc 31.3 μg/mL |
| He mycelium, rice, oat hull 21 d, EtOAc 62.5 μg/mL |
| He mycelium, rice, oat hull 21 d, EtOAc 125 μg/mL |
| He mycelium, rice, oat hull 21 d, EtOAc 250 μg/mL |
| He mycelium, rice, oat hull 98 d, $H_2O$ 31.3 μg/mL |
| He mycelium, rice, oat hull 98 d, $H_2O$ 62.5 μg/mL |
| He mycelium, rice, oat hull 98 d, $H_2O$ 125 μg/mL |
| He mycelium, rice, oat hull 98 d, $H_2O$ 250 μg/mL |
| He mycelium, rice, oat hull 98 d, EtOH 31.3 μg/mL |
| He mycelium, rice, oat hull 98 d, EtOH 62.5 μg/mL |
| He mycelium, rice, oat hull 98 d, EtOH 125 μg/mL |
| He mycelium, rice, oat hull 98 d, EtOH 250 μg/mL |
| He mycelium, rice, oat hull 98 d, EtOAc 31.3 μg/mL |
| He mycelium, rice, oat hull 98 d, EtOAc 62.5 μg/mL |
| He mycelium, rice, oat hull 98 d, EtOAc 125 μg/mL |
| He mycelium, rice, oat hull 98 d, EtOAc 250 μg/mL |
| He fruiting body, $H_2O$ 31.3 μg/mL |
| He fruiting body, $H_2O$ 62.5 μg/mL |
| He fruiting body, $H_2O$ 62.5 μg/mL |
| He fruiting body, $H_2O$ 125 μg/mL |
| He fruiting body, $H_2O$ 250 μg/mL |
| He fruiting body, EtOH 31.3 μg/mL |
| He fruiting body, EtOH 62.5 μg/mL |
| He fruiting body, EtOH 125 μg/mL |
| He fruiting body, EtOH 250 μg/mL |
| He fruiting body, EtOAc 31.3 μg/mL |
| He fruiting body, EtOAc 62.5 μg/mL |
| He fruiting body, EtOAc 125 μg/mL |
| He fruiting body, EtOAc 250 μg/mL |
| He mycelium, 198 d, EtOAc 31.3 μg/mL |
| He mycelium, 198 d, EtOAc 62.5 μg/mL |
| He mycelium, 198 d, EtOAc 125 μg/mL |
| He mycelium, 198 d, EtOAc 250 μg/mL |
| baeocystin 0.3 μg/mL |
| baeocystin 1 μg/mL |
| baeocystin 3 μg/mL |
| baeocystin 10 μg/mL |
| norbaeocystin 0.3 μg/mL |
| norbaeocystin 1 μg/mL |
| norbaeocystin 2 μg/mL |
| norbaeocystin 10 μg/mL |
| norpsilocin 0.3 μg/mL |
| norpsilocin 1 μg/mL |

TABLE 4-continued

| Test Compositions |
|---|
| norpsilocin 3 μg/mL |
| norpsilocin 10 μg/mL |
| He mycelium 62.5 μg/mL + baeocystin 0.3 μg/mL |
| He mycelium 125 μg/mL + baeocystin 0.3 μg/mL |
| He mycelium 62.5 μg/mL + baeocystin 1 μg/mL |
| He mycelium 125 μg/mL + baeocystin 1 μg/mL |
| He mycelium 62.5 μg/mL + norbaeocystin 0.3 μg/mL |
| He mycelium 125 μg/mL + norbaeocystin 0.3 μg/mL |
| He mycelium 62.5 μg/mL + norbaeocystin 1 μg/mL |
| He mycelium 125 μg/mL + norbaeocystin 1 μg/mL |
| He mycelium 62.5 μg/mL + norpsilocin 0.3 μg/mL |
| He mycelium 125 μg/mL + norpsilocin 0.3 μg/mL |
| He mycelium 62.5 μg/mL + norpsilocin 1 μg/mL |
| He mycelium 125 μg/mL + norpsilocin 1 μg/mL |

Experiments were conducted by Neurofit Contract Research Organization in Illkirch-Graffenstaden, France.

Rat Induced Pluripotent Stem Cell (iPSC) Neuron Culture

Cryopreserved iCell neurons were thawed and plated according to instructions from the provider (Cellular Dynamics International). The treatments were carried out 2 h after the cell plating. The cells were maintained in a humidified incubator at 37° C. in a 5% $CO_2$ atmosphere.

The following protocol was performed for each independent culture. Six culture experiments were performed for each condition.

| Day | Procedure |
|---|---|
| 0 | Primary cultures of cortical neurons from rat embryo were initiated; Treatment with test compounds |
| 3 | Re-treatment with test compounds |
| 7 | Re-treatment with test compounds |
| 10 | Evaluated neurite network growth in tubulin immunostained neurons |

Each culture plate contained a negative and positive control condition. Cells were treated with vehicle (negative control), 50 ng/mL brain-derived neurotrophic factor (BDNF) (positive control), or the different test compositions at the four different doses.

Evaluation of Neurite Outgrowth and Length

After ten days of culturing, the cultures were fixed with 4% paraformaldehyde in PBS. The cells were successively permeabilized, saturated with PBS containing 3% w/v bovine serum albumin (BSA) and incubated for 1 h with anti-beta Ill tubulin antibody (Sigma) diluted at 1/10000 in PBS containing 0.5% of BSA. Cells wre first washed and are then were incubated for 1 h with goat anti-mouse antibody coupled with AF488 (Invitrogen Δ11001) diluted at 1/1000 in PBS containing 0.5% of BSA. Finally, nuclei are stained with DAPI 1 mg/mL at 1/1000 in PBS containing 0.5% of BSA. After rinsing the cells with PBS, the plate is imaged and neurite networks are examined and analyzed using High-Content Screening (Celllnsight, Thermo Scientific Inc.).

Results are expressed as mean (±Standard Deviation). Statistical analyses of the data were performed using one-way analysis of variance (ANOVA). Where applicable, Fisher's PLSD test was used for multiple pairwise comparisons. The level of significance is set at p-value less or equal to 0.05.

Figure 2:
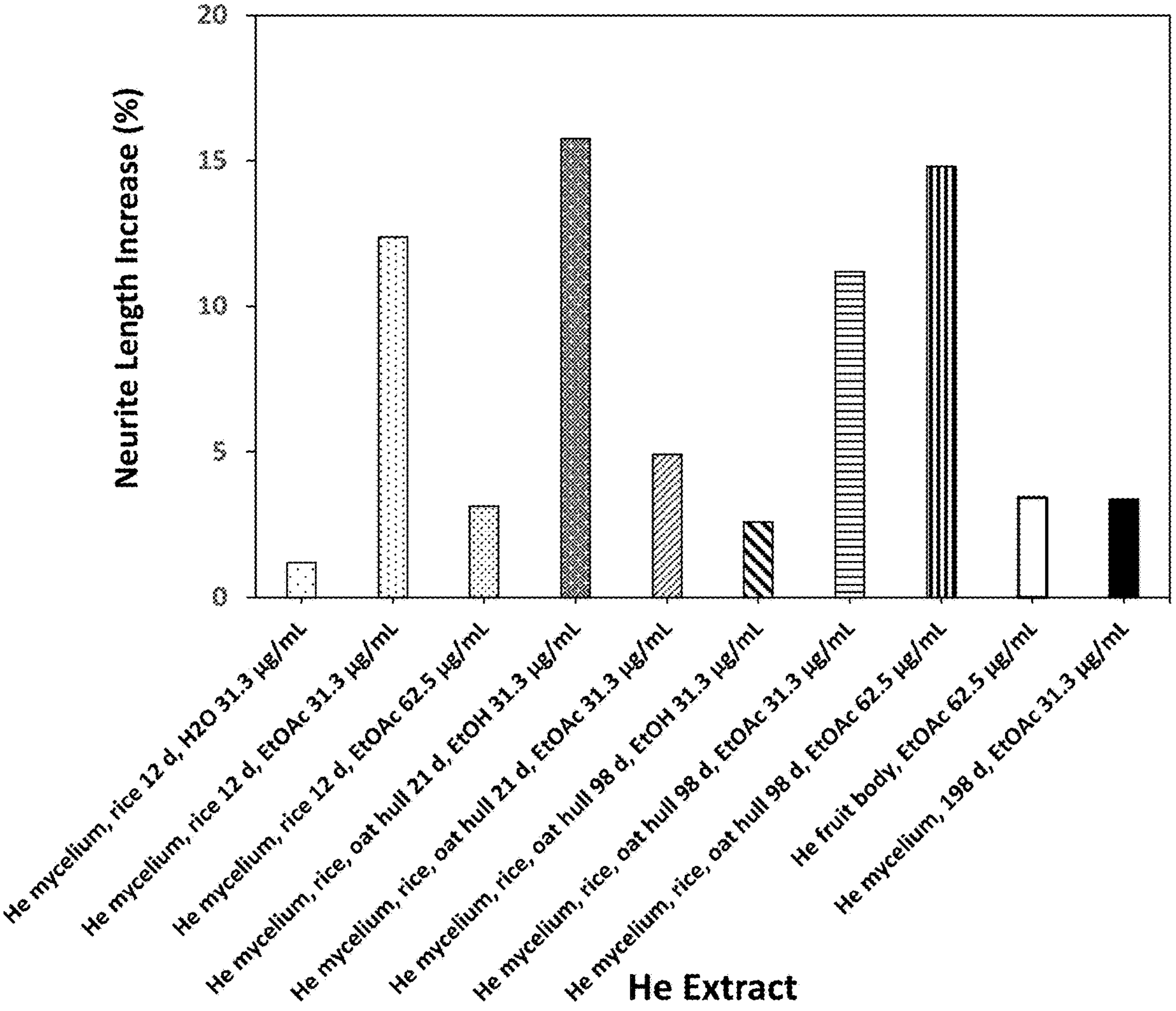
FIG. 2 shows the effect of selected concentrations of H. *erinaceus* extract on neurite growth relative to the vehicle control. Data is shown in Table 7.
Figure 3:
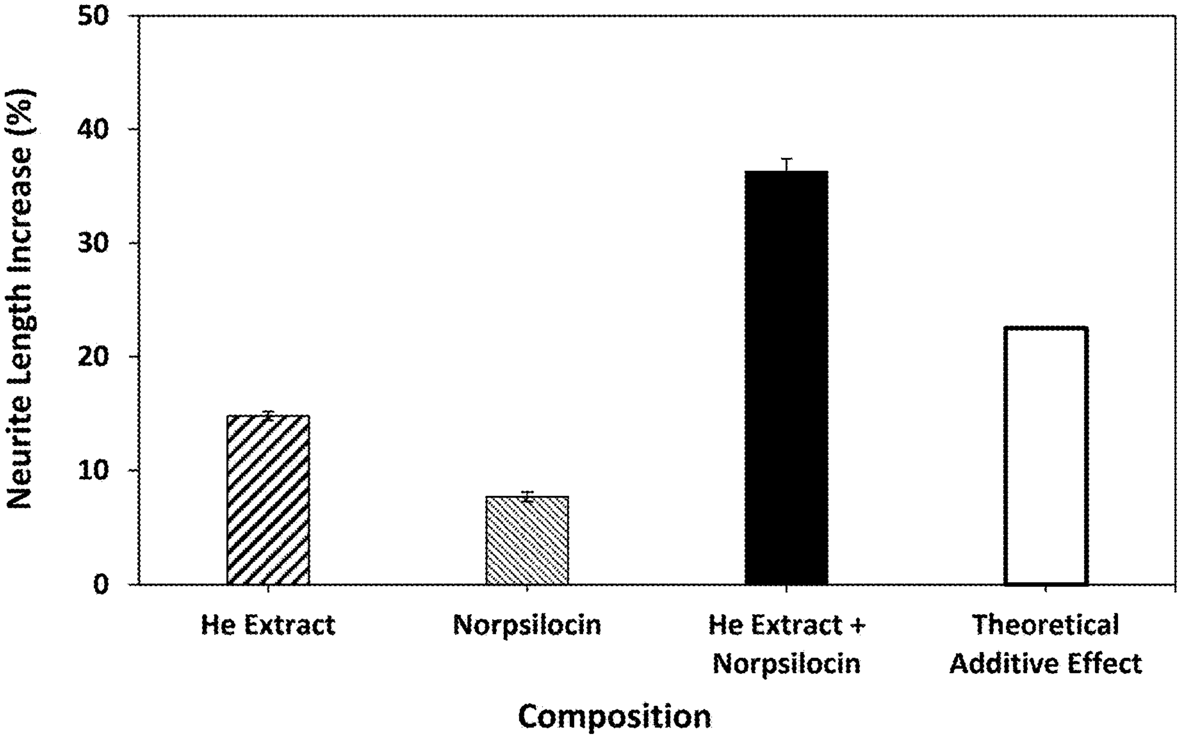
FIG. 3 shows the effect of norbaeocystin and H. *erinaceus* extract on neurite growth relative to the vehicle control. Data is shown in Table 8.
Figure 4:
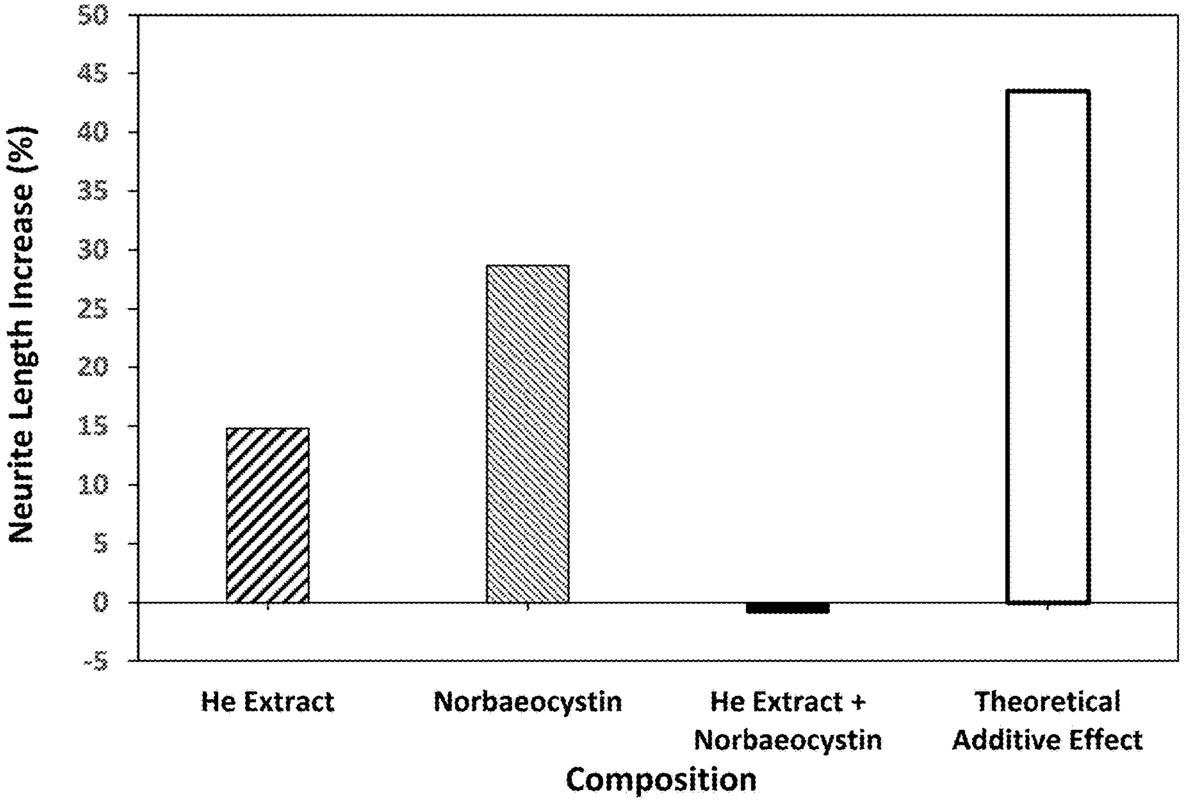
FIG. 4 shows the effect of norpsilocin and H. *erinaceus* extract on neurite growth relative to the vehicle control. Data is shown in Table 9.
Figure 5:
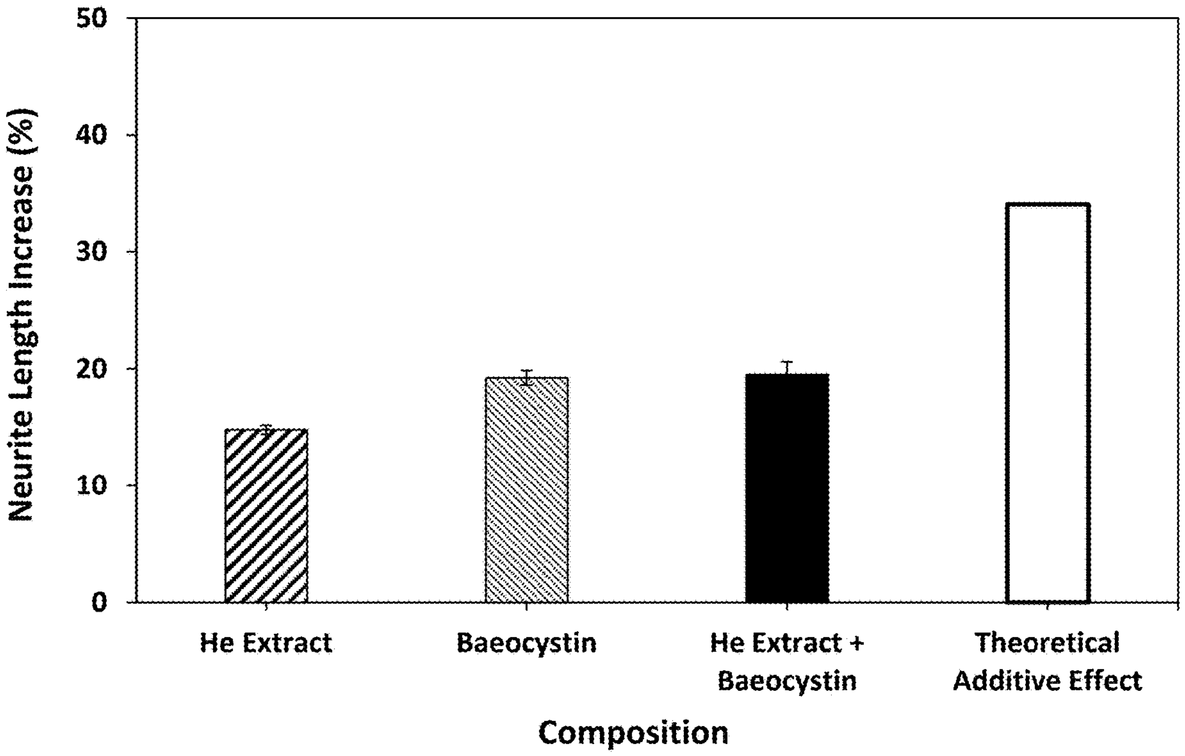
FIG. 5 shows the effect of baeocystin and H. *erinaceus* extract on neurite growth relative to the vehicle control. Data is shown in Table 10.

The evaluation of neurite outgrowth is performed using the average number of neurites per neuron and the average of total neurite length per neuron. Data is shown in Table 5. Tables 6-9 show selections of data from Table 5 that includes the neurite length % of control data plotted in FIG. 1-3. Norpsilocin as a single compound did not perform better than vehicle control in this experiment at these concentrations. Surprisingly, the most pronounced neurite outgrowth was produced by combining lion's mane extract (HE Myc) with norpsilocin suggesting that HE Myc and norpsilocin work together synergistically to produce an increased effect on neurite outgrowth (FIG. 3). Generally, the lower concentration ranges tended to produce the most significant impact on neurite length.

TABLE 5

Results of Neurite Outgrowth and Length

| | Neurites per neuron | | | | Neurite length per neuron | | | |
|---|---|---|---|---|---|---|---|---|
| | Number | | % of control | | Length (μm) | | % of control | |
| Composition/Control | Avg. | Std. Dev. | Avg. | Std. Dev. | Avg. | Std. Dev. | Avg. | Std. Dev. |
| Vehicle | 3.24 | 0.12 | 100.00 | 3.79 | 364.93 | 52.46 | 100.00 | 14.38 |
| BDNF 50 ng/mL | 3.82 | 0.14 | 117.76 | 4.43 | 528.55 | 55.31 | 144.84 | 15.16 |
| He mycelium, rice 12 d, H2O 31.3 μg/mL | 3.04 | 0.13 | 93.81 | 3.89 | 369.32 | 39.43 | 101.20 | 10.80 |
| He mycelium, rice 12 d, H2O 62.5 μg/mL | 2.76 | 0.14 | 85.07 | 4.43 | 318.27 | 47.44 | 87.21 | 13.00 |
| He mycelium, rice 12 d, H2O 125 μg/mL | 2.62 | 0.24 | 80.78 | 7.53 | 243.57 | 26.04 | 66.74 | 7.13 |
| He mycelium, rice 12 d, H2O 250 μg/mL | 1.56 | 0.12 | 48.18 | 3.62 | 90.61 | 7.14 | 24.83 | 1.96 |
| He mycelium, rice 12 d, EtOH 31.3 μg/mL | 2.66 | 0.47 | 82.08 | 14.40 | 277.26 | 89.32 | 75.97 | 24.48 |
| He mycelium, rice 12 d, EtOH 62.5 μg/mL | 3.00 | 0.12 | 92.65 | 3.80 | 329.45 | 18.81 | 90.28 | 5.15 |
| He mycelium, rice 12 d, EtOH 125 μg/mL | 2.60 | 0.14 | 80.16 | 4.43 | 213.46 | 19.25 | 58.49 | 5.27 |
| He mycelium, rice 12 d, EtOH 250 μg/mL | 0.68 | 0.25 | 21.07 | 7.72 | 30.88 | 12.12 | 8.46 | 3.32 |
| Vehicle | 3.29 | 0.06 | 100.00 | 1.85 | 373.68 | 33.23 | 100.00 | 8.89 |
| BDNF 50 ng/mL | 3.91 | 0.12 | 119.01 | 3.60 | 562.36 | 34.91 | 150.49 | 9.34 |
| He mycelium, rice 12 d, EtOAc 31.3 μg/mL | 3.03 | 0.13 | 92.14 | 3.92 | 419.95 | 34.28 | 112.38 | 9.17 |

TABLE 5-continued

| Results of Neurite Outgrowth and Length | | | | | | | | |
|---|---|---|---|---|---|---|---|---|
| | Neurites per neuron | | | | Neurite length per neuron | | | |
| | Number | | % of control | | Length (μm) | | % of control | |
| Composition/Control | Avg. | Std. Dev. | Avg. | Std. Dev. | Avg. | Std. Dev. | Avg. | Std. Dev. |
| He mycelium, rice 12 d, EtOAc 62.5 μg/mL | 2.91 | 0.10 | 88.46 | 2.98 | 385.38 | 48.34 | 103.13 | 12.94 |
| He mycelium, rice 12 d, EtOAc 125 μg/mL | 2.74 | 0.09 | 83.34 | 2.62 | 345.61 | 50.36 | 92.49 | 13.48 |
| He mycelium, rice 12 d, EtOAc 250 μg/mL | 2.72 | 0.07 | 82.85 | 2.24 | 325.09 | 18.75 | 87.00 | 5.02 |
| He mycelium, rice, oat hull 21 d, H2O 31.3 μg/mL | 2.89 | 0.07 | 88.05 | 2.07 | 337.17 | 47.14 | 90.23 | 12.61 |
| He mycelium, rice, oat hull 21 d, H2O 62.5 μg/mL | 2.79 | 0.09 | 84.91 | 2.60 | 283.48 | 28.88 | 75.86 | 7.73 |
| He mycelium, rice, oat hull 21 d, H2O 125 μg/mL | 2.28 | 0.24 | 69.26 | 7.27 | 179.62 | 27.35 | 48.07 | 7.32 |
| He mycelium, rice, oat hull 21 d, H2O 250 μg/mL | 0.84 | 0.17 | 25.54 | 5.17 | 34.78 | 8.46 | 9.31 | 2.26 |
| Vehicle | 3.21 | 0.19 | 100.00 | 5.85 | 328.29 | 45.85 | 100.00 | 13.97 |
| BDNF 50 ng/mL | 3.84 | 0.13 | 119.47 | 4.09 | 518.78 | 40.30 | 158.03 | 12.28 |
| He mycelium, rice, oat hull 21 d, EtOH 31.3 μg/mL | 3.04 | 0.07 | 94.73 | 2.14 | 380.02 | 26.71 | 115.76 | 8.14 |
| He mycelium, rice, oat hull 21 d, EtOH 62.5 μg/mL | 2.93 | 0.14 | 91.08 | 4.43 | 330.07 | 34.42 | 100.54 | 10.48 |
| He mycelium, rice, oat hull 21 d, EtOH 125 μg/mL | 2.73 | 0.19 | 84.97 | 5.95 | 244.31 | 27.01 | 74.42 | 8.23 |
| He mycelium, rice, oat hull 21 d, EtOH 250 μg/mL | 1.13 | 0.20 | 35.16 | 6.24 | 56.72 | 9.90 | 17.28 | 3.02 |
| He mycelium, rice, oat hull 21 d, EtOAc 31.3 μg/mL | 2.78 | 0.12 | 86.54 | 3.86 | 344.39 | 16.14 | 104.90 | 4.92 |
| He mycelium, rice, oat hull 21 d, EtOAc 62.5 μg/mL | 2.71 | 0.14 | 84.22 | 4.47 | 314.55 | 22.29 | 95.82 | 6.79 |
| He mycelium, rice, oat hull 21 d, EtOAc 125 μg/mL | 2.46 | 0.10 | 76.60 | 3.11 | 231.09 | 16.44 | 70.39 | 5.01 |
| He mycelium, rice, oat hull 21 d, EtOAc 250 μg/mL | 1.46 | 0.24 | 45.53 | 7.38 | 81.91 | 19.16 | 24.95 | 5.84 |
| Vehicle | 3.34 | 0.09 | 100.00 | 2.74 | 337.25 | 44.13 | 100.00 | 13.08 |
| BDNF 50 ng/mL | 3.92 | 0.09 | 117.30 | 2.78 | 506.15 | 51.13 | 150.08 | 15.16 |
| He mycelium, rice, oat hull 98 d, H2O 31.3μg/mL | 2.93 | 0.10 | 87.58 | 3.00 | 333.12 | 54.38 | 98.78 | 16.13 |
| He mycelium, rice, oat hull 98 d, H2O 62.5 μg/mL | 2.45 | 0.13 | 73.23 | 4.00 | 271.77 | 24.09 | 80.59 | 7.14 |
| He mycelium, rice, oat hull 98 d, H2O 125 μg/mL | 1.41 | 0.15 | 42.15 | 4.59 | 80.72 | 18.35 | 23.93 | 5.44 |
| He mycelium, rice, oat hull 98 d, H2O 250 μg/mL | 0.70 | 0.07 | 20.79 | 2.15 | 19.12 | 2.00 | 5.67 | 0.59 |
| He mycelium, rice, oat hull 98 d, EtOH 31.3 μg/mL | 3.06 | 0.23 | 91.60 | 6.95 | 345.99 | 47.76 | 102.59 | 14.16 |
| He mycelium, rice, oat hull 98 d, EtOH 62.5 μg/mL | 2.93 | 0.17 | 87.68 | 5.02 | 302.99 | 20.20 | 89.84 | 5.99 |
| He mycelium, rice, oat hull 98 d, EtOH 125 μg/mL | 0.46 | 0.13 | 13.62 | 3.99 | 25.51 | 11.91 | 7.56 | 3.53 |
| He mycelium, rice, oat hull 98 d, EtOH 250 μg/mL | 0.10 | 0.04 | 2.95 | 1.22 | 1.72 | 0.98 | 0.51 | 0.29 |
| Vehicle | 3.31 | 0.05 | 100.00 | 1.40 | 366.88 | 49.52 | 100.00 | 13.50 |
| BDNF 50 ng/mL | 3.83 | 0.12 | 115.54 | 3.71 | 522.46 | 48.31 | 142.40 | 13.17 |
| He mycelium, rice, oat hull 98 d, EtOAc 31.3 μg/mL | 3.07 | 0.07 | 92.66 | 2.23 | 407.96 | 38.10 | 111.19 | 10.38 |
| He mycelium, rice, oat hull 98 d, EtOAc 62.5 μg/mL | 3.17 | 0.10 | 95.64 | 2.98 | 421.18 | 14.05 | 114.80 | 3.83 |
| He mycelium, rice, oat hull 98 d, EtOAc 125 μg/mL | 2.93 | 0.08 | 88.36 | 2.48 | 331.54 | 35.84 | 90.37 | 9.77 |
| He mycelium, rice, oat hull 98 d, EtOAc 250 μg/mL | 0.14 | 0.05 | 4.26 | 1.54 | 6.31 | 7.55 | 1.72 | 2.06 |
| He fruiting body, H2O 31.3 μg/mL | 2.92 | 0.09 | 88.22 | 2.61 | 339.52 | 61.06 | 92.54 | 16.64 |
| He fruiting body, H2O 62.5 μg/mL | 2.85 | 0.13 | 86.08 | 4.06 | 329.39 | 53.90 | 89.78 | 14.69 |
| He fruiting body, H2O 125 μg/mL | 2.86 | 0.05 | 86.28 | 1.54 | 280.77 | 19.31 | 76.53 | 5.26 |
| He fruiting body, H2O 250 μg/mL | 1.52 | 0.27 | 45.96 | 8.24 | 88.38 | 17.68 | 24.09 | 4.82 |
| Vehicle | 3.18 | 0.12 | 100.00 | 3.71 | 363.68 | 52.28 | 100.00 | 14.37 |
| BDNF 50 ng/mL | 3.72 | 0.15 | 116.93 | 4.72 | 468.09 | 61.98 | 128.71 | 17.04 |

TABLE 5-continued

Results of Neurite Outgrowth and Length

| Composition/Control | Neurites per neuron: Number Avg. | Neurites per neuron: Number Std. Dev. | Neurites per neuron: % of control Avg. | Neurites per neuron: % of control Std. Dev. | Neurite length per neuron: Length (μm) Avg. | Neurite length per neuron: Length (μm) Std. Dev. | Neurite length per neuron: % of control Avg. | Neurite length per neuron: % of control Std. Dev. |
|---|---|---|---|---|---|---|---|---|
| He fruiting body, EtOH 31.3 μg/mL | 2.91 | 0.10 | 91.59 | 3.01 | 358.36 | 63.57 | 98.53 | 17.48 |
| He fruiting body, EtOH 62.5 μg/mL | 2.69 | 0.23 | 84.74 | 7.13 | 331.97 | 93.68 | 91.28 | 25.76 |
| He fruiting body, EtOH 125 μg/mL | 2.76 | 0.18 | 86.71 | 5.68 | 359.08 | 70.83 | 98.74 | 19.47 |
| He fruiting body, EtOH 250 μg/mL | 2.55 | 0.23 | 80.29 | 7.28 | 277.97 | 64.75 | 76.43 | 17.80 |
| He fruiting body, EtOAc 31.3 μg/mL | 2.90 | 0.04 | 91.28 | 1.20 | 349.19 | 72.01 | 96.02 | 19.80 |
| He fruiting body, EtOAc 62.5 μg/mL | 2.94 | 0.17 | 92.61 | 5.48 | 376.15 | 58.62 | 103.43 | 16.12 |
| He fruiting body, EtOAc 125 μg/mL | 2.97 | 0.18 | 93.59 | 5.80 | 349.24 | 66.57 | 96.03 | 18.30 |
| He fruiting body, EtOAc 250 μg/mL | 1.12 | 0.41 | 35.24 | 13.01 | 68.32 | 44.12 | 18.79 | 12.13 |
| Vehicle | 3.16 | 0.12 | 100.00 | 3.81 | 350.81 | 17.64 | 100.00 | 5.03 |
| BDNF 50 ng/mL | 3.74 | 0.14 | 118.17 | 4.37 | 522.96 | 47.79 | 149.07 | 13.62 |
| He mycelium, 198 d, EtOAc 31.3 μg/mL | 2.20 | 0.13 | 69.70 | 3.96 | 362.62 | 52.91 | 103.37 | 15.08 |
| He mycelium, 198 d, EtOAc 62.5 μg/mL | 0.07 | 0.02 | 2.16 | 0.67 | 1.34 | 0.32 | 0.38 | 0.09 |
| He mycelium, 198 d, EtOAc 125 μg/mL | 0.49 | 0.84 | 15.34 | 26.47 | 30.91 | 49.75 | 8.81 | 14.18 |
| He mycelium, 198 d, EtOAc 250 μg/mL | 0.06 | 0.05 | 2.02 | 1.65 | 1.64 | 1.12 | 0.47 | 0.32 |
| baeocystin 0.3 μg/mL | 2.99 | 0.06 | 94.46 | 1.92 | 418.30 | 22.03 | 119.24 | 6.28 |
| baeocystin 1 μg/mL | 2.96 | 0.10 | 93.66 | 3.21 | 394.11 | 47.14 | 112.34 | 13.44 |
| baeocystin 3 μg/mL | 3.07 | 0.10 | 97.18 | 3.23 | 415.42 | 55.25 | 118.42 | 15.75 |
| baeocystin 10 μg/mL | 3.06 | 0.12 | 96.87 | 3.81 | 384.52 | 43.27 | 109.61 | 12.33 |
| Vehicle | 3.34 | 0.18 | 100.00 | 5.43 | 343.36 | 51.31 | 100.00 | 14.94 |
| BDNF 50 ng/mL | 3.80 | 0.23 | 113.92 | 6.83 | 510.71 | 88.59 | 148.74 | 25.80 |
| norbaeocystin 0.3 μg/mL | 3.09 | 0.07 | 92.67 | 2.18 | 441.86 | 39.02 | 128.69 | 11.36 |
| norbaeocystin 1 μg/mL | 3.06 | 0.10 | 91.64 | 2.99 | 436.93 | 34.89 | 127.25 | 10.16 |
| norbaeocystin 3 μg/mL | 2.90 | 0.07 | 87.02 | 2.11 | 385.00 | 42.74 | 112.13 | 12.45 |
| norbaeocystin 10 μg/mL | 3.07 | 0.14 | 92.01 | 4.20 | 386.86 | 27.40 | 112.67 | 7.98 |
| norpsilocin 0.3 μg/mL | 2.80 | 0.38 | 83.77 | 11.39 | 344.09 | 58.88 | 107.70 | 4.15 |
| norpsilocin 1 μg/mL | 2.91 | 0.19 | 87.18 | 5.71 | 347.25 | 35.93 | 101.13 | 10.46 |
| norpsilocin 3 μg/mL | 2.65 | 0.34 | 79.36 | 10.16 | 253.40 | 43.87 | 73.80 | 12.78 |
| norpsilocin 10 μg/mL | 0.92 | 0.31 | 27.71 | 9.18 | 26.28 | 10.58 | 7.65 | 3.08 |
| Vehicle | 3.16 | 0.13 | 100.00 | 4.05 | 332.48 | 37.69 | 100.00 | 11.34 |
| BDNF 50 ng/mL | 3.78 | 0.09 | 119.83 | 2.95 | 501.08 | 39.32 | 150.71 | 11.83 |
| He mycelium 62.5 μg/mL + baeocystin 0.3 μg/mL | 3.01 | 0.14 | 95.47 | 4.29 | 397.38 | 36.35 | 119.52 | 10.93 |
| He mycelium 125 μg/mL + baeocystin 0.3 μg/mL | 2.67 | 0.08 | 84.62 | 2.47 | 257.79 | 29.48 | 77.53 | 8.87 |
| He mycelium 62.5 μg/mL + baeocystin 1 μg/mL | 2.78 | 0.11 | 88.12 | 3.40 | 310.54 | 25.97 | 93.40 | 7.81 |
| He mycelium 125 μg/mL + baeocystin 1 μg/mL | 0.06 | 0.03 | 1.87 | 0.87 | 1.47 | 1.01 | 0.44 | 0.30 |
| He mycelium 62.5 μg/mL + norbaeocystin 0.3 μg/mL | 2.98 | 0.10 | 94.30 | 3.32 | 329.72 | 19.82 | 99.17 | 5.96 |
| He mycelium 125 μg/mL + norbaeocystin 0.3 μg/mL | 2.07 | 0.21 | 65.48 | 6.71 | 267.64 | 45.96 | 80.50 | 13.82 |
| He mycelium 62.5 μg/mL + norbaeocystin 1 μg/mL | 3.06 | 0.06 | 96.84 | 1.93 | 354.91 | 27.14 | 106.75 | 8.16 |
| He mycelium 125 μg/mL + norbaeocystin 1 μg/mL | 2.61 | 0.14 | 82.74 | 4.32 | 231.75 | 37.26 | 69.70 | 11.21 |
| Vehicle | 3.00 | 0.16 | 100.00 | 5.28 | 295.88 | 63.27 | 100.00 | 21.38 |
| BDNF 50 ng/mL | 3.81 | 0.12 | 127.06 | 3.93 | 568.90 | 44.08 | 192.27 | 14.90 |
| He mycelium 62.5 μg/mL + norpsilocin 0.3 μg/mL | 3.07 | 0.16 | 102.43 | 5.27 | 403.20 | 33.36 | 136.27 | 11.28 |
| He mycelium 125 μg/mL + norpsilocin 0.3 μg/mL | 2.06 | 0.07 | 68.81 | 2.46 | 335.41 | 28.34 | 113.36 | 9.58 |
| He mycelium 62.5 μg/mL + norpsilocin 1 μg/mL | 2.81 | 0.21 | 93.60 | 7.08 | 298.51 | 54.51 | 100.89 | 18.42 |
| He mycelium 125 μg/mL + norpsilocin 1 μg/mL | 2.58 | 0.11 | 85.93 | 3.77 | 234.16 | 31.58 | 79.14 | 10.67 |

TABLE 6

Neurite Outgrowth and Length

| Composition | Neurites per neuron: Number Avg. | Number Std. Dev. | % of control Avg. | % of control Std. Dev. | Neurite length per neuron: Length (μm) Avg. | Length (μm) Std. Dev. | % of control Avg. | % of control Std. Dev. |
|---|---|---|---|---|---|---|---|---|
| baeocystin 0.3 μg/mL | 2.99 | 0.06 | 94.46 | 1.92 | 418.30 | 22.03 | 119.24 | 6.28 |
| baeocystin 1 μg/mL | 2.96 | 0.10 | 93.66 | 3.21 | 394.11 | 47.14 | 112.34 | 13.44 |
| baeocystin 3 μg/mL | 3.07 | 0.10 | 97.18 | 3.23 | 415.42 | 55.25 | 118.42 | 15.75 |
| baeocystin 10 μg/mL | 3.06 | 0.12 | 96.87 | 3.81 | 384.52 | 43.27 | 109.61 | 12.33 |
| norbaeocystin 0.3 μg/mL | 3.09 | 0.07 | 92.67 | 2.18 | 441.86 | 39.02 | 128.69 | 11.36 |
| norbaeocystin 1 μg/mL | 3.06 | 0.10 | 91.64 | 2.99 | 436.93 | 34.89 | 127.25 | 10.16 |
| norbaeocystin 3 μg/mL | 2.90 | 0.07 | 87.02 | 2.11 | 385.00 | 42.74 | 112.13 | 12.45 |
| norbaeocystin 10 μg/mL | 3.07 | 0.14 | 92.01 | 4.20 | 386.86 | 27.40 | 112.67 | 7.98 |
| norpsilocin 0.3 μg/mL | 2.80 | 0.38 | 83.77 | 11.39 | 344.09 | 58.88 | 107.70 | 4.15 |
| norpsilocin 1 μg/mL | 2.91 | 0.19 | 87.18 | 5.71 | 347.25 | 35.93 | 101.13 | 10.46 |
| norpsilocin 3 μg/mL | 2.65 | 0.34 | 79.36 | 10.16 | 253.40 | 43.87 | 73.80 | 12.78 |
| norpsilocin 10 μg/mL | 0.92 | 0.31 | 27.71 | 9.18 | 26.28 | 10.58 | 7.65 | 3.08 |

TABLE 7

Neurite Outgrowth and Length

| Composition | Neurites per neuron: Number Avg. | Number Std. Dev. | % of control Avg. | % of control Std. Dev. | Neurite length per neuron: Length (μm) Avg. | Length (μm) Std. Dev. | % of control Avg. | % of control Std. Dev. |
|---|---|---|---|---|---|---|---|---|
| He mycelium, rice 12 d, H2O 31.3 μg/mL | 3.04 | 0.13 | 93.81 | 3.89 | 369.32 | 39.43 | 101.20 | 10.80 |
| He mycelium, rice 12 d, EtOAc 31.3 μg/mL | 3.03 | 0.13 | 92.14 | 3.92 | 419.95 | 34.28 | 112.38 | 9.17 |
| He mycelium, rice 12 d, EtOAc 62.5 μg/mL | 2.91 | 0.10 | 88.46 | 2.98 | 385.38 | 48.34 | 103.13 | 12.94 |
| He mycelium, rice, oat hull 21 d, EtOH 31.3 μg/mL | 3.04 | 0.07 | 94.73 | 2.14 | 380.02 | 26.71 | 115.76 | 8.14 |
| He mycelium, rice, oat hull 21 d, EtOAc 31.3 μg/mL | 2.78 | 0.12 | 86.54 | 3.86 | 344.39 | 16.14 | 104.90 | 4.92 |
| He mycelium, rice, oat hull 98 d, EtOH 31.3 μg/mL | 3.06 | 0.23 | 91.60 | 6.95 | 345.99 | 47.76 | 102.59 | 14.16 |
| He mycelium, rice, oat hull 98 d, EtOAc 31.3 μg/mL | 3.07 | 0.07 | 92.66 | 2.23 | 407.96 | 38.10 | 111.19 | 10.38 |
| He mycelium, rice, oat hull 98 d, EtOAc 62.5 μg/mL | 3.17 | 0.10 | 95.64 | 2.98 | 421.18 | 14.05 | 114.80 | 3.83 |
| He fruiting body, EtOAc 62.5 μg/mL | 2.94 | 0.17 | 92.61 | 5.48 | 376.15 | 58.62 | 103.43 | 16.12 |
| He mycelium, 198 d, EtOAc 31.3 μg/mL | 2.20 | 0.13 | 69.70 | 3.96 | 362.62 | 52.91 | 103.37 | 15.08 |

TABLE 8

Neurite Outgrowth and Length

| Composition | Neurites per neuron: Number Avg. | Number Std. Dev. | % of control Avg. | % of control Std. Dev. | Neurite length per neuron: Length (μm) Avg. | Length (μm) Std. Dev. | % of control Avg. | % of control Std. Dev. |
|---|---|---|---|---|---|---|---|---|
| He mycelium, rice, oat hull 98 d, EtOAc 62.5 μg/mL | 3.17 | 0.10 | 95.64 | 2.98 | 421.18 | 14.05 | 114.80 | 3.83 |
| Norpsilocin 0.3 μg/mL | 2.80 | 0.38 | 83.77 | 11.39 | 344.09 | 58.88 | 107.70 | 4.15 |
| He mycelium 62.5 μg/mL + norpsilocin 0.3 μg/mL | 3.07 | 0.16 | 102.43 | 5.27 | 403.20 | 33.36 | 136.27 | 11.28 |
| Theoretical Additive Effect | 2.62 | | 79.41 | | 424.97 | | 122.49 | |

TABLE 9

| Neurite Outgrowth and Length | | | | | | | | |
|---|---|---|---|---|---|---|---|---|
| | Neurites per neuron | | | | Neurite length per neuron | | | |
| | Number | | % of control | | Length (μm) | | % of control | |
| Composition | Avg. Avg. | Std. Dev. Std. Dev. | Avg. Avg. | Std. Dev. Std. Dev. | Avg. Avg. | Std. Dev. Std. Dev. | Avg. Avg. | Std. Dev. Std. Dev. |
| He mycelium, rice, oat hull 98 d, EtOAc 62.5 μg/mL | 3.17 | 0.10 | 95.64 | 2.98 | 421.18 | 14.05 | 114.80 | 3.83 |
| Norbaeocystin 0.3 μg/mL | 3.09 | 0.07 | 92.67 | 2.18 | 441.86 | 39.02 | 128.69 | 11.36 |
| He mycelium 62.5 μg/mL + norbaeocystin 0.3 μg/mL | 2.98 | 0.10 | 94.30 | 3.32 | 329.72 | 19.82 | 99.17 | 5.96 |
| Theoretical Additive Effect | 2.92 | | 88.32 | | 522.74 | | 143.49 | |

TABLE 10

| Neurite Outgrowth and Length | | | | | | | | |
|---|---|---|---|---|---|---|---|---|
| | Neurites per neuron | | | | Neurite length per neuron | | | |
| | Number | | % of control | | Length (μm) | | % of control | |
| Composition | Avg. | Std. Dev. | Avg. | Std. Dev. | Avg. | Std. Dev. | Avg. | Std. Dev. |
| He mycelium, rice, oat hull 98 d, EtOAc 62.5 μg/mL | 3.17 | 0.10 | 95.64 | 2.98 | 421.18 | 14.05 | 114.80 | 3.83 |
| Baeocystin 0.3 μg/mL | 2.99 | 0.06 | 94.46 | 1.92 | 418.30 | 22.03 | 119.24 | 6.28 |
| He mycelium 62.5 μg/mL + baeocystin 0.3 μg/mL | 3.01 | 0.14 | 95.47 | 4.29 | 397.38 | 36.35 | 119.52 | 10.93 |
| Theoretical Additive Effect | 2.81 | | 90.10 | | 499.18 | | 134.04 | |

Example 3

Neurite Outgrowth 4 (NO-4) produced statistically significant hits for several HE extracts as well as each psilocybin analog tested in the assay. Subsequently, Neurite Outgrowth 5 tested for potential synergistic effects from combining HE extracts with pure compounds. The treatments were comparable to those of NeuroFit2, aiming to determine if potential synergistic effects identified by NeuroFit were reproducible in-house.

PC12 cells were grown to confluency in a 96 well plate, starved, and treated with HE 98d EtOAc mycelium extract, psilocybin analogs, or HE-analog stacks (FIG. 6). Culture media was refreshed after day 7. Images were taken at days 5, 7, and 11 and were then analyzed for neurite length via ImageJ. Images were taken at 20× and focused on the most prominent instances of neurite outgrowth in each well.

Figure 7:
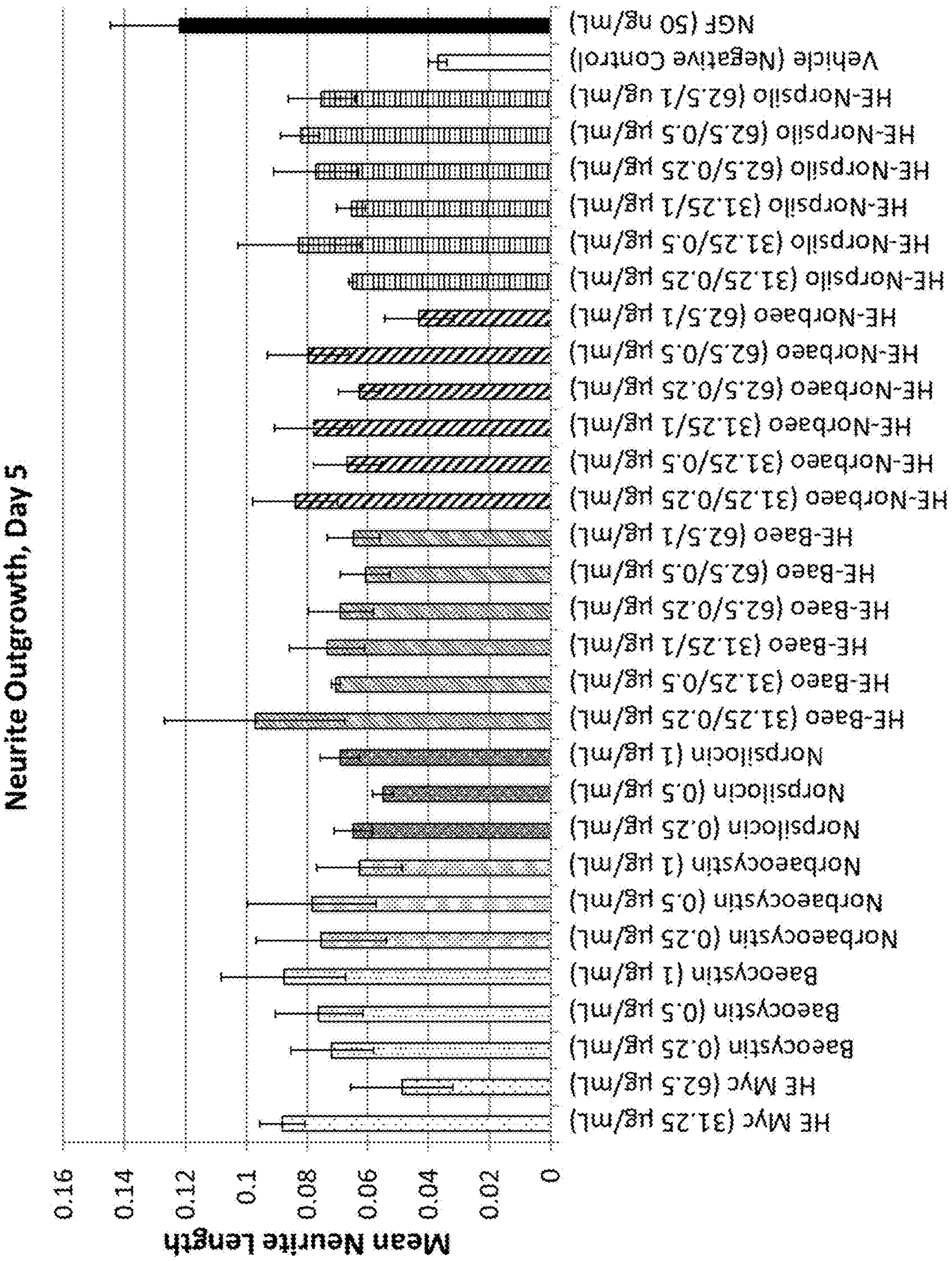
FIG. 7 shows the impact of Hericium *erinaceus* extracts and psilocybin analogs on neurite length at day 5.
Figure 8:
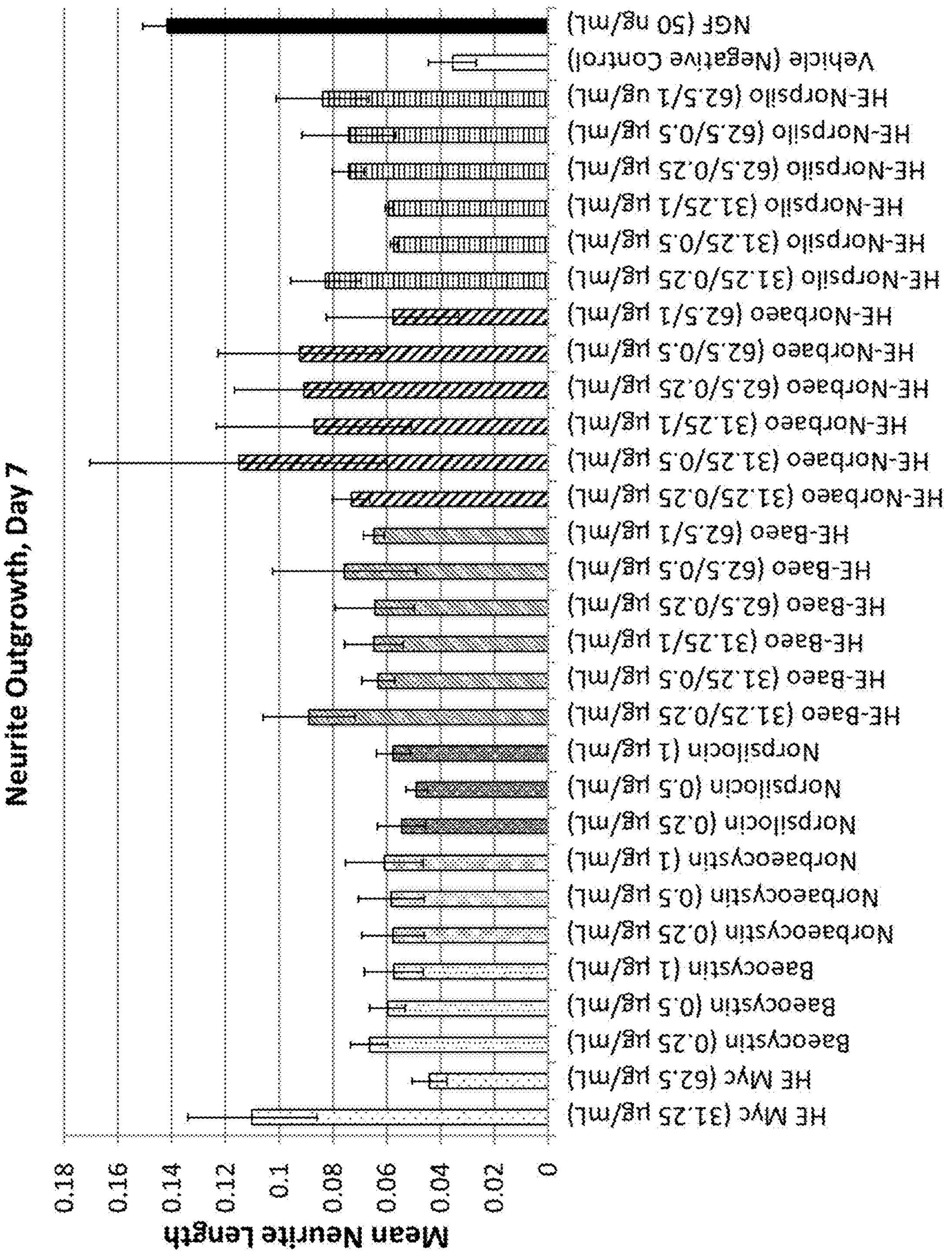
FIG. 8 shows the impact of Hericium *erinaceus* extracts and psilocybin analogs on neurite length at day 7.
Figure 9:
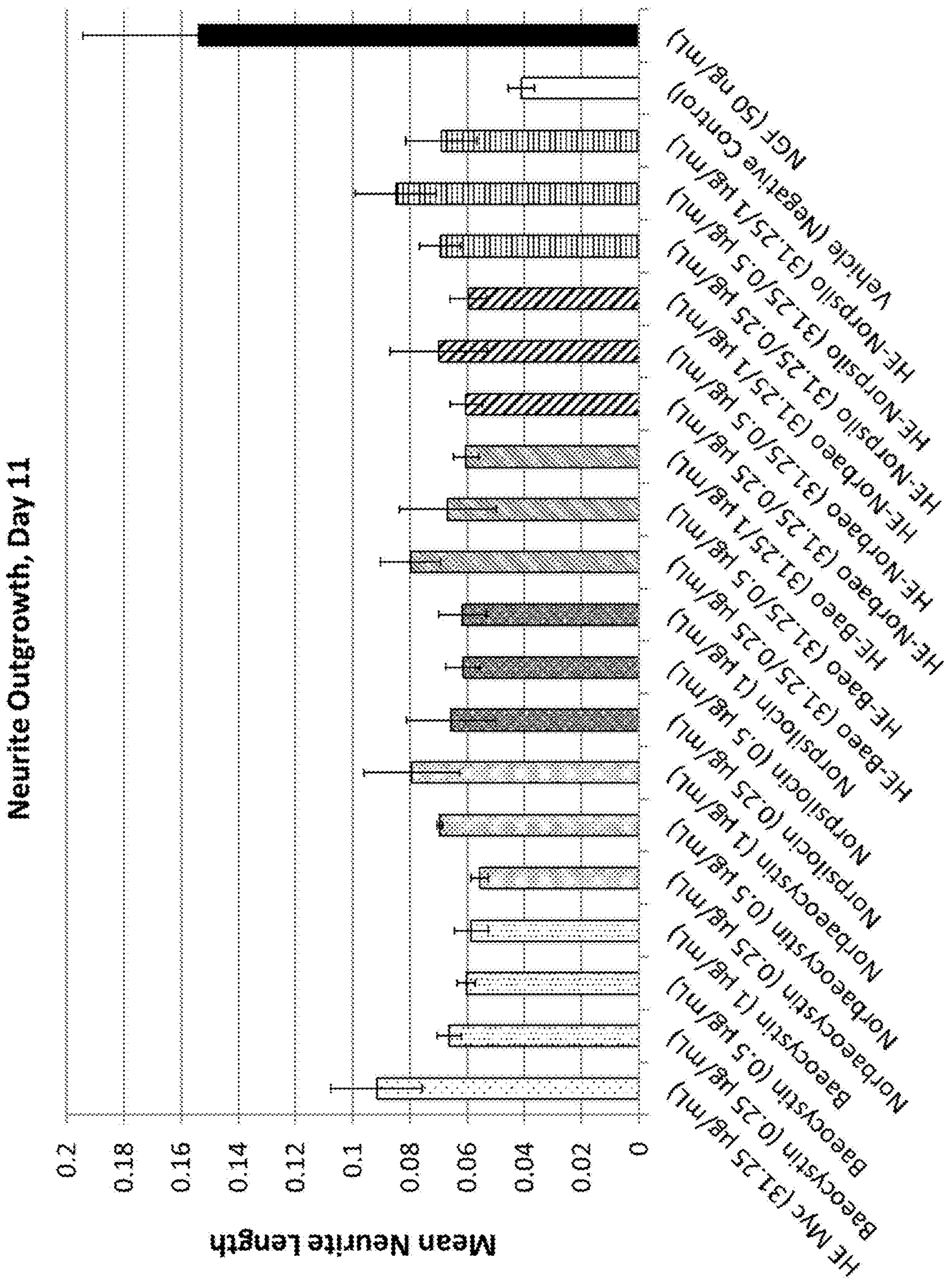
FIG. 9 shows the impact of Hericium *erinaceus* extracts and psilocybin analogs on neurite length at day 11.
Figure 10:
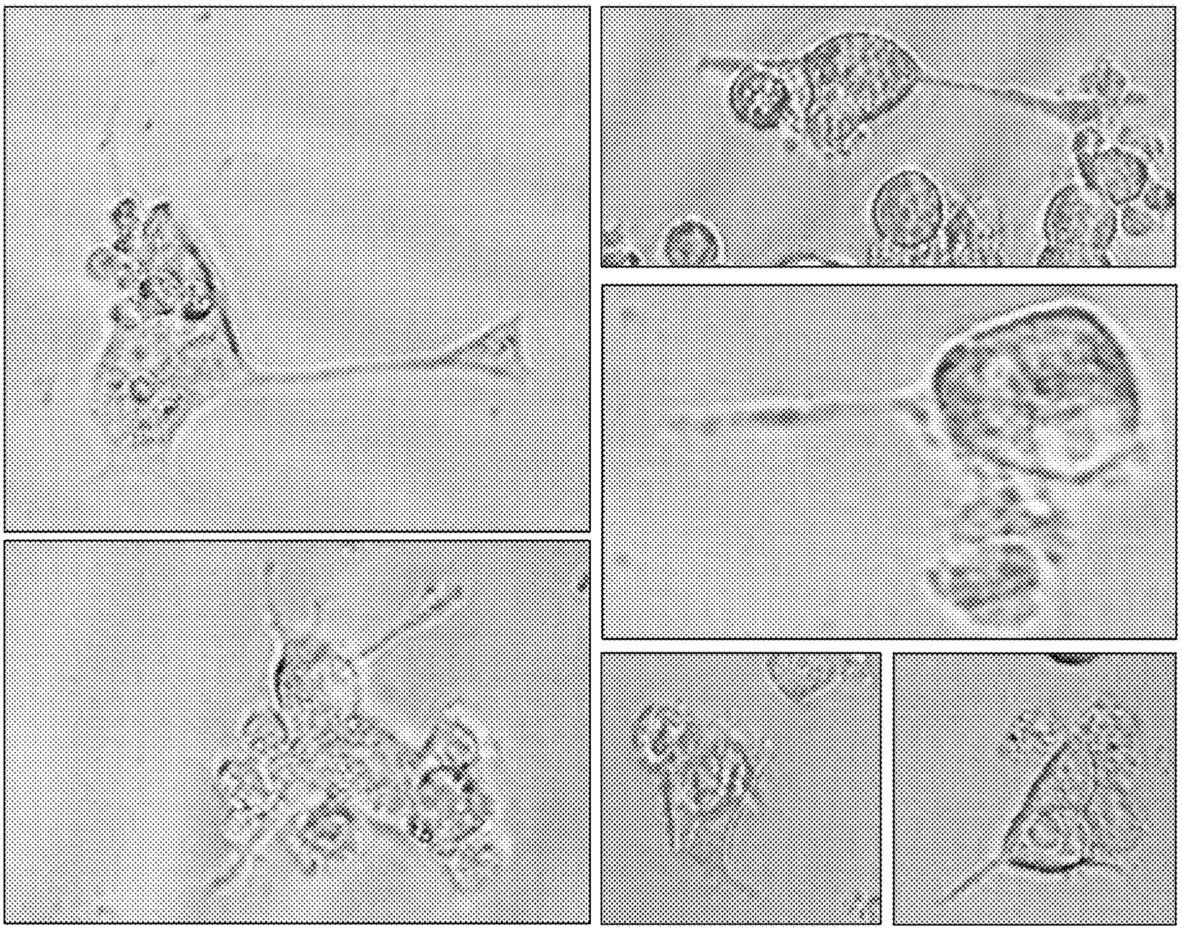
FIG. 10 shows neurite outgrowth induced by HE extracts (Day 7).

Generally, the data from NO-5 largely reflect those of NO-4, and once again, statistically significant hits were identified for HE and psilocybin analogs. At all time points, the 31.25 μg/mL HE extracts produced the strongest neurite outgrowth, having the greatest mean neurite length of any statistically significant treatment (FIGS. 7, 8, 9). Day 7 produced the strongest neurite outgrowth as all treatments tended have the longest mean neurite length at this time point (FIG. 10).

As observed with the previous assay, NO-5 provides further validation of in-house cell culture capabilities and demonstrates that the neurite outgrowth assay can be simplified by applying compounds directly to PC12 cells. Refreshing culture media did not produce a noticeable neurite length benefit to PC12 cells, as the day 11 treatment still appeared to have some reduction in neurite length when compared to day 7. However, at day 11 statistically significant hits were produced for all three psilocybin analogs.

Figure 11:
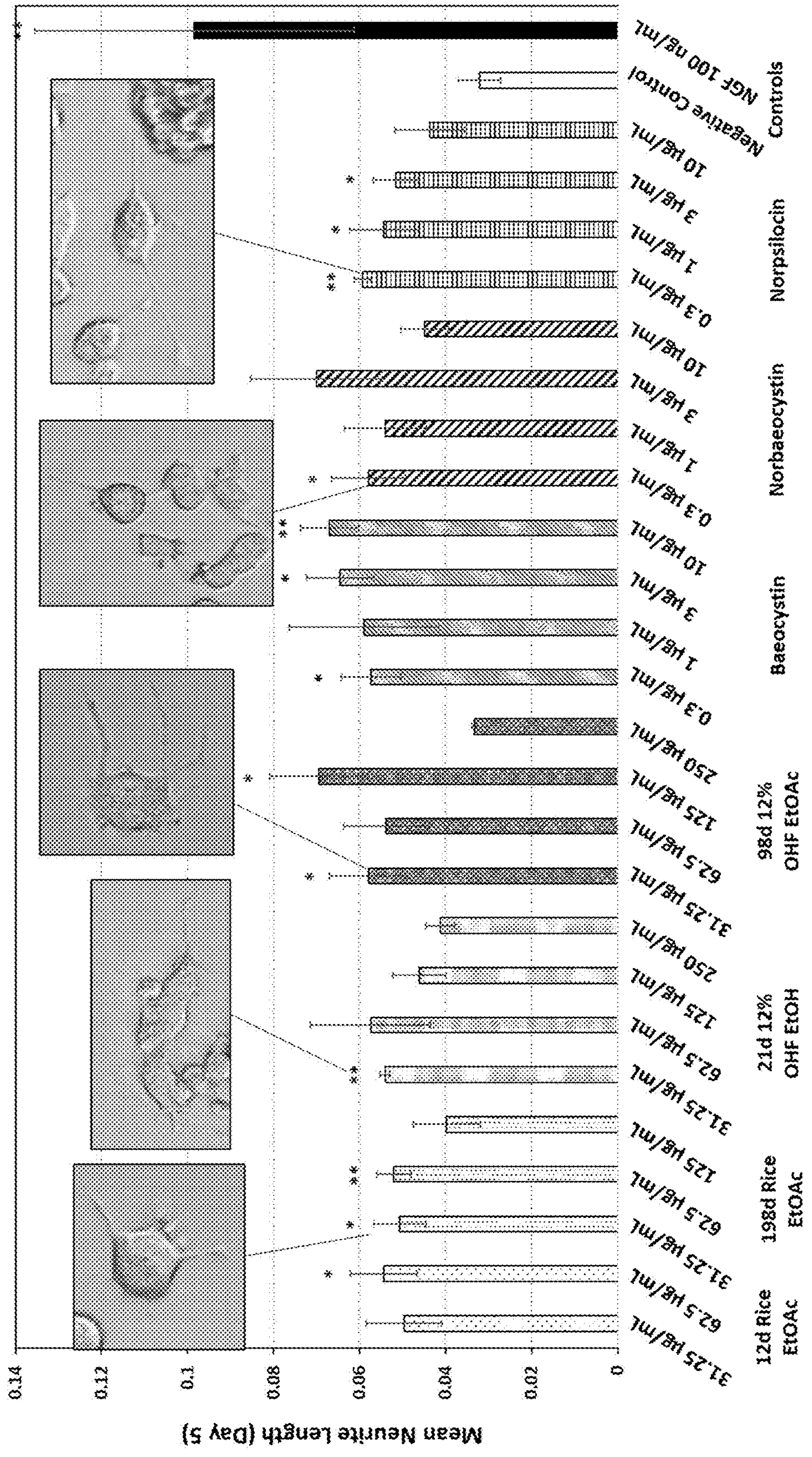
FIG. 11 shows a summary of hits from in-house testing of neurite outgrowth of PC12 cells treated with conditioned media from 1321 N1 cells (n=3).

Although the assay aimed to explore potential synergistic effects of combining HE and psilocybin analogs, this was not clearly observed. This is largely due to the 31.25 μg/mL HE extract outperforming any other individual or stacked treatment at days 5, 7, and 11. In this assay, the 31.25 μg/mL HE extract produced strong neurite outgrowth at a lower dosage than previously observed, likely due to this fresh extract being more concentrated. Overall, these data provide increased confidence in the role of lion's mane extracts and psilocybin analogs in inducing neurite outgrowth both in-house and from third party assays. 1321N1 human brain astrocytoma cells are known to excrete neurologically beneficial compounds when stimulated with neurotrophic compounds and fungal extracts including lion's mane (Mori et al., Biological and Pharmaceutical Bulletin, 9: 1727-1732 (2008)). While some fungi have well established mechanisms by which they benefit neurological health, little is known about the role of psilocybin analogs specifically. Generally following the protocol of Mori et al., 2008, 1321N1 human astrocytoma cells were treated with psilocybin analogs, and conditioned media was collected and applied to differentiated rat pheochromocytoma PC12 cells to determine the resulting impact on neurite outgrowth. Conditioned media from baeocystin, norbaeocystin, and norpsilocin were found to induce neurite outgrowth in PC12 cells, suggesting that psilocybin analogs induce the expression and secretion of neurologically beneficial compounds, potentially including nerve growth factor (NGF) (FIG. 11). When PC12 cells were directly treated with psilocybin analogs, comparable effects were observed at several time points (FIG. 9).

Example 4

Mitogen-activated protein kinases (MAPKs) provide a wide-ranging signaling cascade that allow cells to quickly respond to biotic and abiotic stimuli. The objective of this project was to determine if HE extracts from Fungi Perfecti (FP) impact MAPKs (e.g., influence the expression and phosphorylation of various MAPKs—notably JNK, c-Jun, and c-fos—to promote nerve growth factor (NGF) expression). Here, four FP extracts were tested at three concentrations each (Table 11). These extracts were tested against five MAPKs: c-Jun N-terminal kinase 1-3 (JNK1, JNK2, JNK3), Rho Associated Coiled-Coil Containing Protein Kinases 1 and 2 (ROCK1, ROCK2), and tropomyosin receptor kinase B (TRKB). Collectively, these MAPKs are major players in neural health, influencing neurogenesis, neural growth and differentiation, and neurodegenerative diseases.

TABLE 11

Concentrations of FP HE extracts tested for binding to MAPK targets

| Extract | Concentrations Tested (μg/mL) | | |
|---|---|---|---|
| HD HE Extract | 62.5 | 125 | 250 |
| HE EtOAc | 62.5 | 125 | 250 |
| HE Water Wash | 62.5 | 125 | 250 |
| HD Powder | 31.25 | 62.5 | 125 |

HD: Host Defense ® Lion's Mane (*Hericium erinaceus*) product (Fungi Perfecti)

Figure 12:
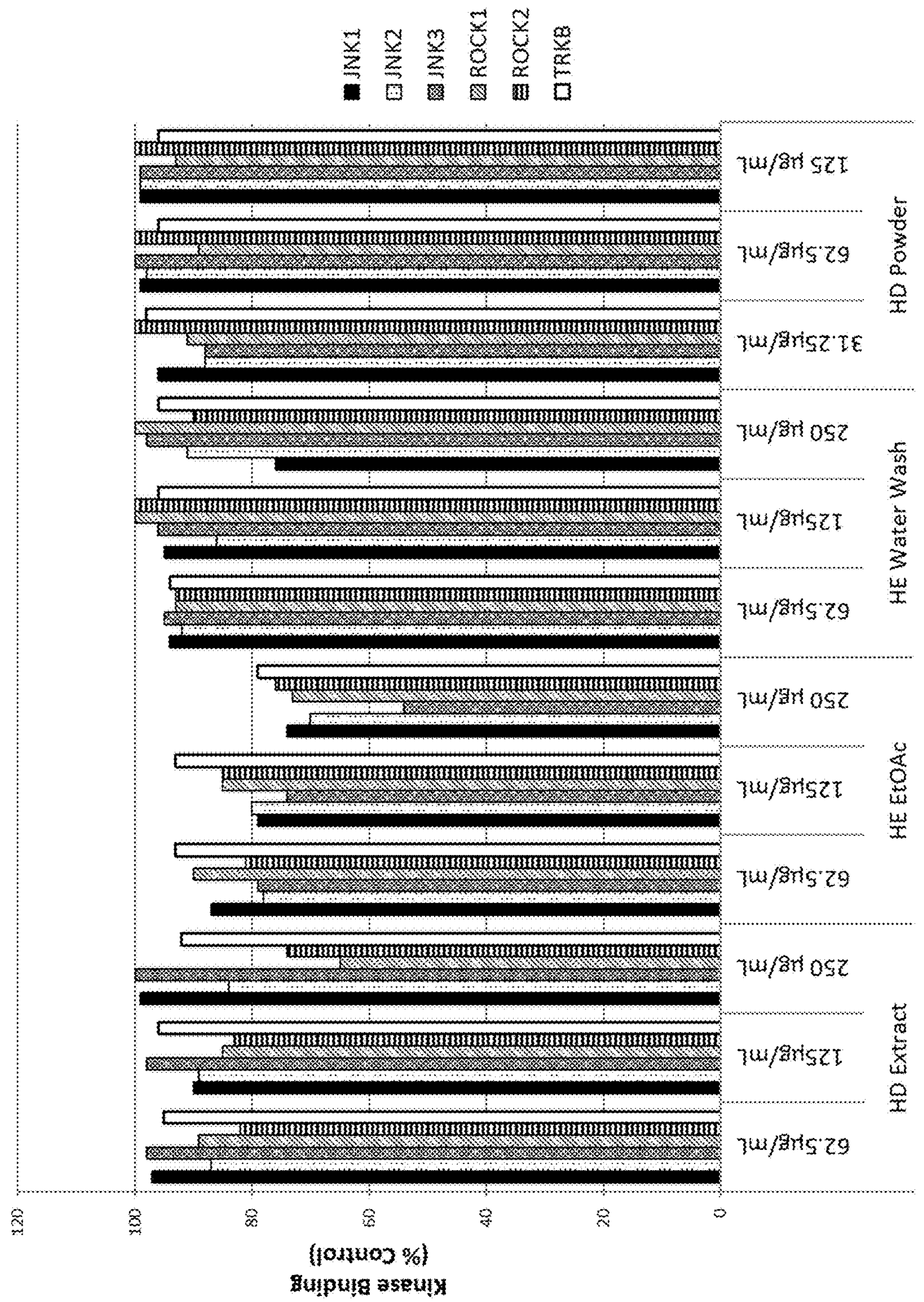
FIG. 12 shows the ability of FP H. *erinaceus* extracts to bind to MAP kinases that influence neural health.

While several potential MAPK hits were identified for all extracts, the Host Defense® (Fungi Perfecti; "HD") HE EtOH and HE EtOAc extracts elicited the most pronounced impacts, particularly the latter extract (FIG. 12). (Note: based on the % Control kinase binding calculation, stronger hits are represented by lower values.)

Interestingly, the top two hits included the HE EtOAc extract on JNK3 and the HD HE EtOH extract with ROCK1 (Table 12). This suggests that the extraction method may play a significant role in the ways in which neural health is impacted. While the strongest MAPK impact was found on JNK3 with the EtOAc extract, the EtOH extract did not produce a strong impact on this specific kinase. This may be due to the EtOAc extraction method producing the strongest detectable erinacine content.

TABLE 12

Top ten hits identified in the MAPK binding assay

| Compound Name | DiscoveRx Gene Symbol | Entrez Gene Symbol | Percent Control | Compound Conc. (μg/mL) |
|---|---|---|---|---|
| HE EtOAc | JNK3 | MAPK10 | 54 | 250 |
| HD Extract | ROCK1 | ROCK1 | 65 | 250 |
| HE EtOAc | JNK2 | MAPK9 | 70 | 250 |
| HE EtOAc | ROCK1 | ROCK1 | 73 | 250 |
| HD Extract | ROCK2 | ROCK2 | 74 | 250 |
| HE EtOAc | JNK3 | MAPK10 | 74 | 125 |
| HE EtOAc | JNK1 | MAPK8 | 74 | 250 |
| HE EtOAc | ROCK2 | ROCK2 | 76 | 250 |
| HE Water Wash | JNK1 | MAPK8 | 76 | 250 |
| HE EtOAc | JNK2 | MAPK9 | 78 | 62.5 |

HD: Host Defense ® Lion's Mane (*Hericium erinaceus*) product (Fungi Perfecti)

Figure 13:
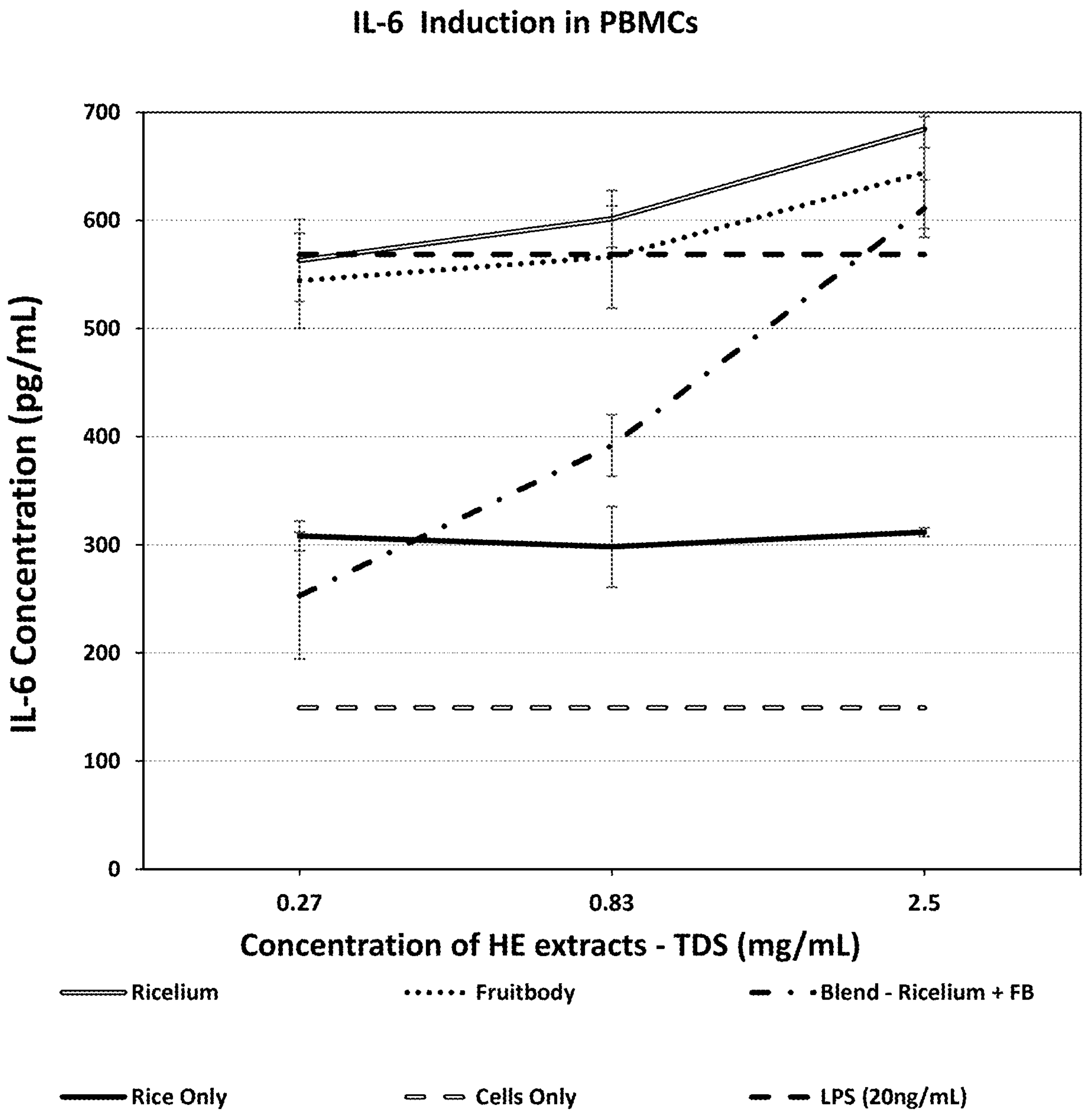
FIG. 13 shows the ability of FP H. *erinaceus* extracts to increase interleukin-6 (IL-6) production in peripheral blood mononuclear cells (PBMCs).
Figure 14:
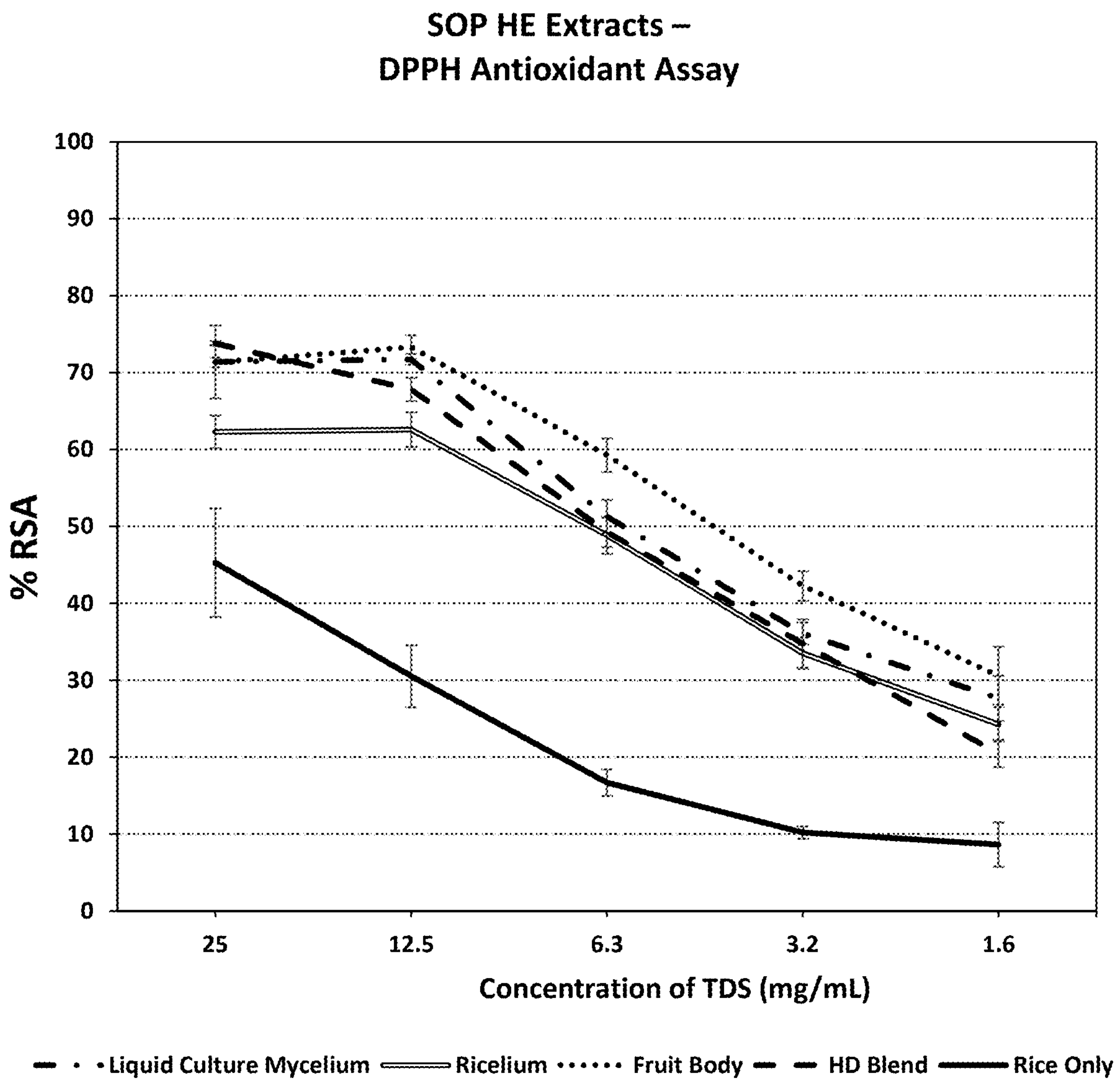
FIG. 14 shows that FP H. *erinaceus* extracts demonstrate radical scavenging activity in the DPPH assay, indicating they have antioxidant activity.
Figure 15:
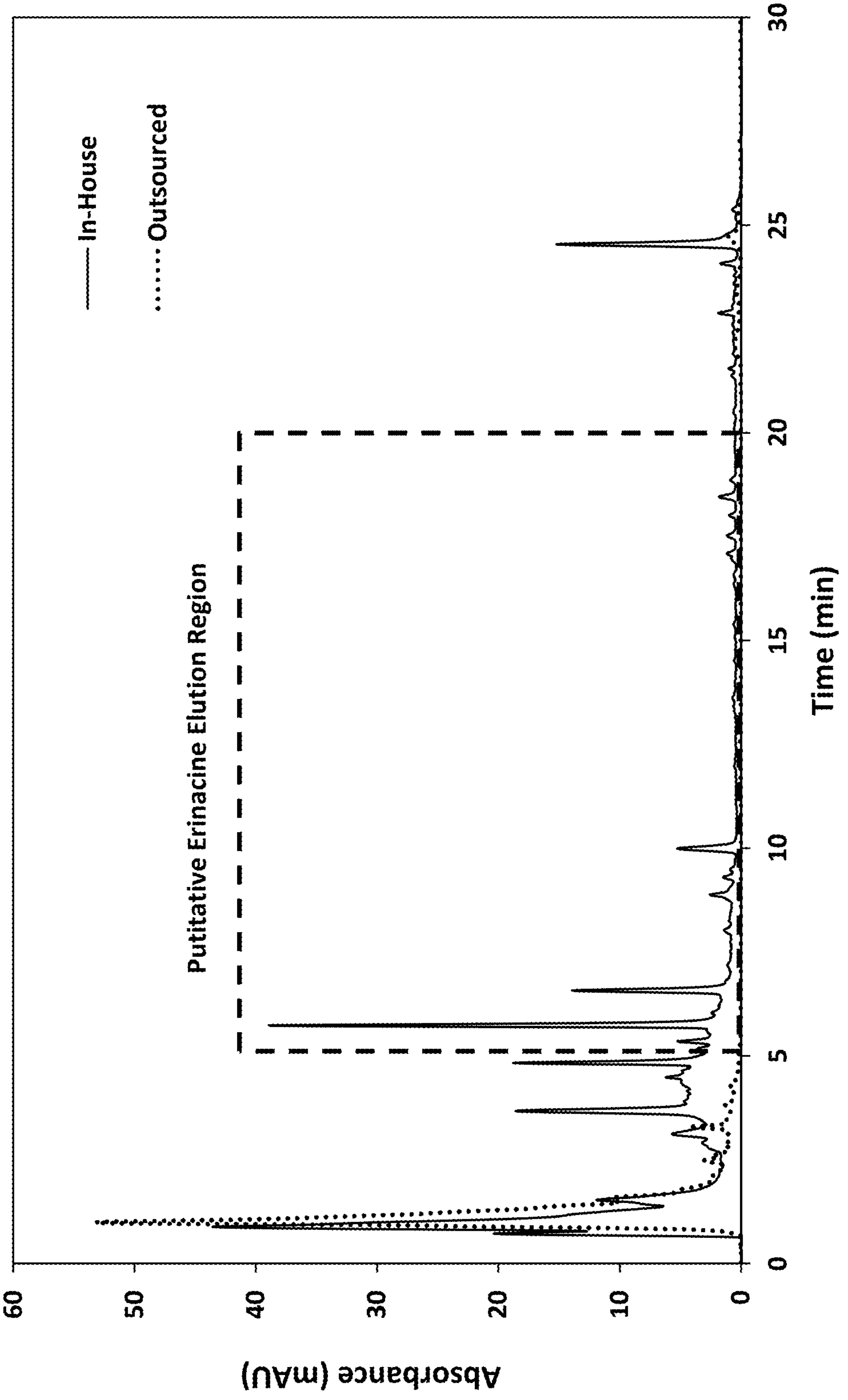
FIG. 15 shows SM1-91-C, suspended in MeOH, filtered through a polypropylene 0.22 μM filter (in-house) and suspended in DMEM, filtered through a cellulose acetate 0.22 μM Filter (Neurofit preparation; outsourced). Solubilizing and sterilizing the sample in this manner eliminates a lot of the complexity in the ethyl acetate fraction, including the putative erinacine peaks.

Collectively, MAPK binding data suggest that FP HE extracts impact neural health on several broad levels. Of the top MAPKs impacted by HE extracts, the JNKs play a role in cell degeneration, while the ROCKs play a role in cell survival. Accordingly, FP HE extracts may play an immunomodulatory role in influencing immune system homeostasis (FIG. 13).

Contrary to results from neurite outgrowth cellular assays, higher extract concentrations in MAPK binding assays tended to elicit a stronger response. At 250 μg/mL, the EtOAc had a strong impact on the binding of TRKB, a well-characterized, high affinity receptor of brain-derived neurotrophic factor (BDNF), further broadening the scope at which FP HE extracts modulate neural activity.

Ultimately, findings from the MAPK binding assays strengthen the mechanisms by which FP HE extracts influence neurogenic activity. In addition to morphology-based cellular assays in several cell lines, there is now evidence that FP extracts are driving neurite growth through diverse, classical neurogenic pathways related to neurotrophic factors including both NGF and BDNF.

Figure 16:
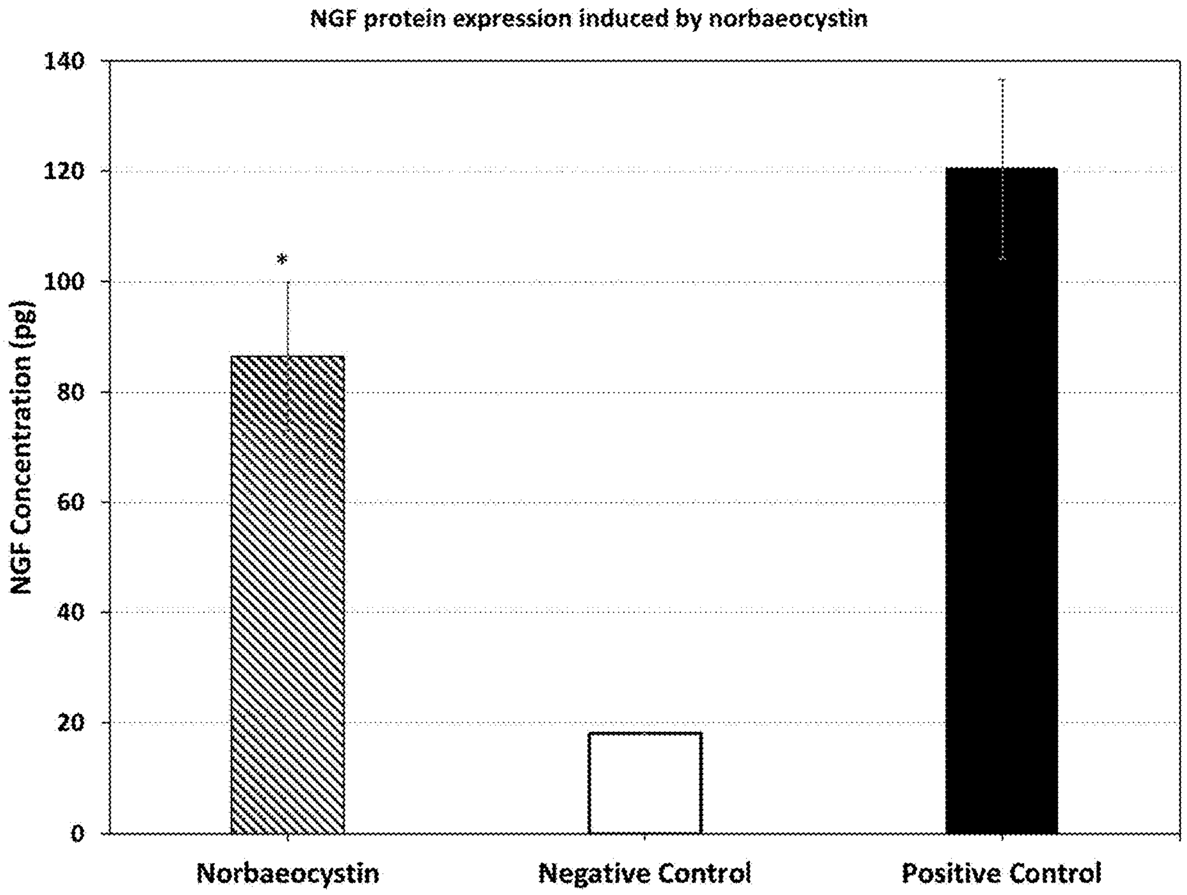
FIG. 16 shows induction of NGF protein induced by norbaeocystin in human 1321 N1 cells (n=3; $p<0.05$).

The ability of psilocybin analogs to stimulate neurite outgrowth is demonstrated in several cell models. Accordingly, preliminary research has started to reveal the mechanisms by which psilocybin analogs may confer neurotrophic benefits that facilitate neurite outgrowth. Human 1321N1 brain cells treated with norbaeocystin have increased expression of NGF protein when compared to a vehicle control (FIG. 16).

Example 5

Figure 17:
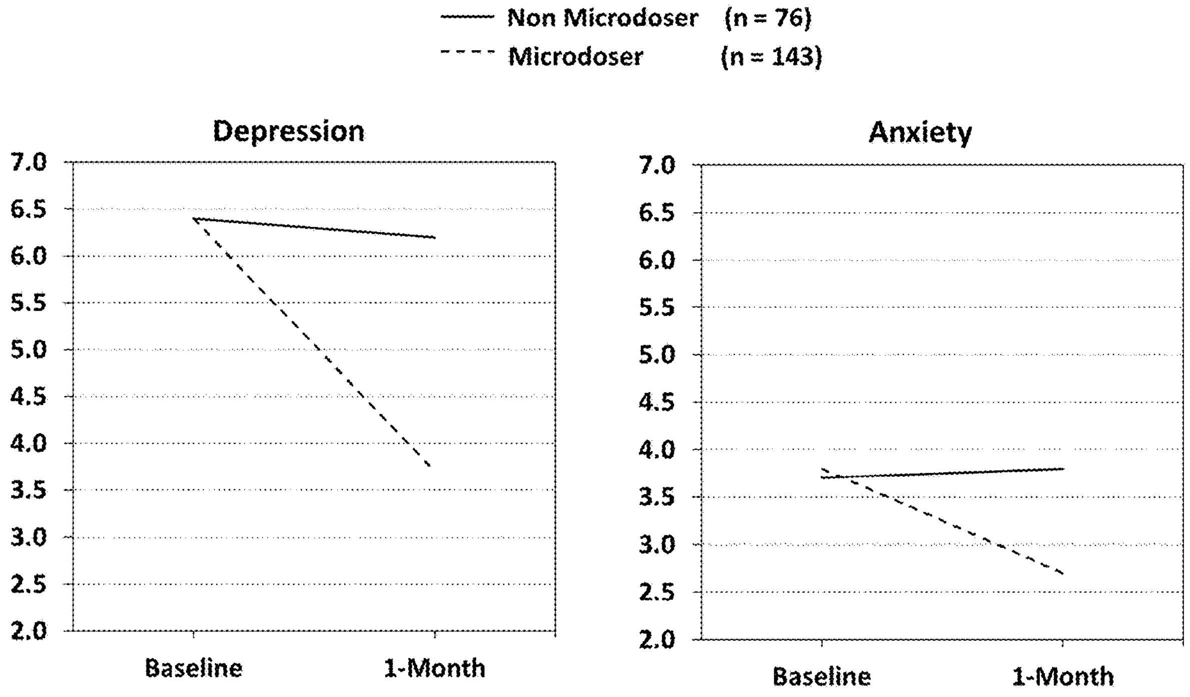
FIG. 17 shows Depression Anxiety and Stress Scale (DASS 21)—Range 0-42. $F(1,217)=12.44$, $p<0.001$, $r1^2=0.05$, $F(1,217)=3.99$, $p<0.05$, $r2=0.02$.
Figure 18:
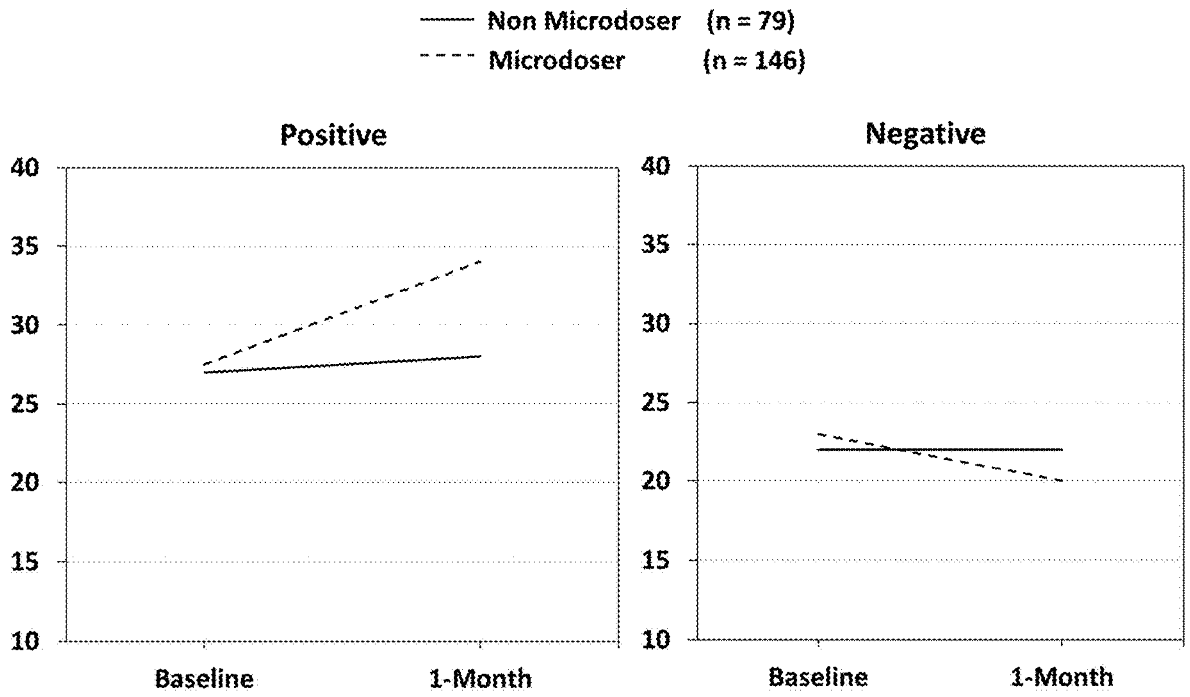
FIG. 18 shows Positive and Negative Affect Scale (PANAS)—Range 10-50. $F(1,223)=35.12$, $p<0.00001$, $rn^2=0.13$, $F(1,223)=13.90$, $p<0.001$, $rn^2=0.06$.
Figure 19:
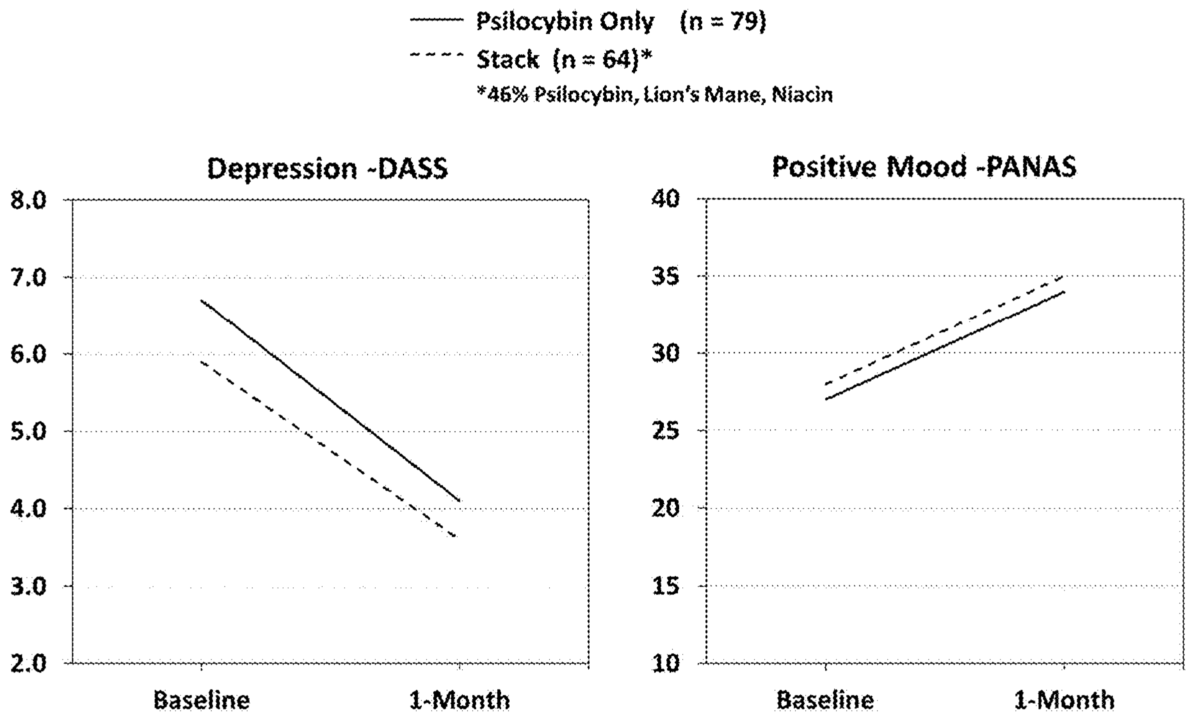
FIG. 19 shows that there are no differences in stacking versus psilocybin alone at 4 weeks—All $F(1,141)<1$, $p>0.5$.

Microdosing with dried psilocybin mushrooms (presumption: Psilocybe *cubensis*) in humans was used to study the effects of psilocybin mushrooms on depression, anxiety, and mood. The data was collected using anonymous self-reporting through a phone app (microdose.me). 16% of respondents reported using a low dose (<0.10 grams), 72% of respondents reported using a medium dose (0.10-0.30 grams), and 12% of respondents reported using a high dose (>30 grams). The large study sample included 8703 participants at baseline with 3,486 psilocybin users, 447 LSD users, 117 other (46.5% were microdosers). A subsample of the large sample included 159 participants that started microdosing psilocybin with 1-month FU (28% female) and 83 participants that were non-microdosers (19% female). Among microdosers, 22% dosed<2×/wk, 47% dosed 2-4×/wk, and 29% dosed>4×/wk. Microdosing was correlated with decreased depression and anxiety as compared to non-microdosers (FIG. 17) and increased positive mood as compared to non-microdosers (FIG. 18). Stacking psilocybin mushrooms with Lion's Mane mushrooms did not increase the effect on depression or positive mood as compared to psilocybin mushrooms alone (FIG. 19). Positive effects were equivalent among those who stacked with Lion's Mane (with and without niacin) and those who did not stack. However, the data was collected after 4 weeks of administration and data has shown that Lion's Mane, when used in clinical studies, increased cognition at 8, 12 and 16 weeks. Therefore, the psilocybin and Lion's Mane stack may work synergistically to treat depression and anxiety and increase positive mood when used in combination for greater than 4 weeks. Overall, microdosing psilocybin was associated with reduced depression and improved mood at 1 month. Effects for depression were in the medium range: $r2=0.05/d=0.5$, whereas SSRIs are in the $d=0.3$ range. It is notable that this is a non-clinical population. Effects for positive mood were large—$\eta 2=0.13/d=0.8$.

Example 6

Pochonia chlamydosporia is a fungal egg parasite of root-knot and cyst nematodes. It colonizes in the roots of several plant species and can induce plant defense mechanisms and local resistance in fungal-nematode-plant interactions. It has also been shown that Pochonia chlamydosporia can produce ketamine. Ferreira et al., Parasites & Vectors, 13:527 (2020). Pochonia chlamydosporia will be cocultured with psilocybin-containing mushroom mycelia. Alternatively, Pochonia chlamydosporia will be cultured alone on a substrate such as a rice substrate and its mycelium will be inactivated or killed. Then, psilocybin-containing mushrooms will be cultivated upon the inactivated, ketamine producing mycelium and substrate. These growing conditions may produce novel alkaloids or medicines that may be used for treating or preventing neuronal injuries, neurodegeneration, neurological diseases, congenital or organic cognitive impairment, learning disabilities, autism spectrum disorder, psychiatric and mood disorders, cognitive enhancement, physical or motor neuron enhancement, or general improvement of mental health, inter alia.

The cultivated Pochonia chlamydosporia and/or psilocybin-containing mushrooms are frozen and ground and extracted in water for 2 h at room temperature. The extract is filtered through Whatman filter via gravity. The filtrate is lyophilized to dryness. Ethanol extracts are made from the same mycelium. The mycelium is frozen, but not ground, and extracted in 70% ethanol for 1 week at room temperature. The extract is filtered through an 80-mesh sieve and lyophilized to dryness. A portion of the ethanol extract is rotovapped to dryness and the residue is resuspended in 1:1 water:ethyl acetate. The water/ethyl acetate extract is washed 3 times with ethyl acetate, the combined organic fractions dried over $MgSO_4$, filtered, rotovapped, and then lyophilized.

Additionally, Pochonia species and Psilocybe species (or other psilocybin producing fungi) can be co-cultured together in fermentation or on solid ("semi-solid media") to create a quorum of two organisms whose active principle ingredients-such as ketamine or ketamine analogs from Pochnia and psilocybin/psilocin and psilocybin/psilocin analogues—may be expressed, and subsequently harvested to create a unique combination.

At least 30 mg of psilocybin (0.5-1 mg/kg) is a strong dose, while 70 mg of ketamine 1.5 mg/kg (0.5-2.0 mg/kg) is a similarly strong psychedelic dose.

Experiments are conducted to evaluate the neurotrophic effects of several purified tryptamines, H. erinaceum extracts combined with selected extracts of Pochonia chlamydosporia. The experiments analyze the Pochonia chlamydosporia growth medium (rice, oat, straw, sawdust, or combinations thereof), the days of cultivation, the extract solvent (water, ethanol, or ethyl acetate), and the final concentration of the extract. The following compositions are tested (Table 13):

TABLE 13

| Test Compositions |
|---|
| *Pochonia chlamydosporia* mycelium, rice 12 d, $H_2O$ |
| *Pochonia chlamydosporia* mycelium, oat 12 d, $H_2O$ |
| *Pochonia chlamydosporia* mycelium, straw 12 d, $H_2O$ |
| *Pochonia chlamydosporia* mycelium, sawdust 12 d, $H_2O$ |
| *Pochonia chlamydosporia* mycelium, rice 12 d, EtOH |
| *Pochonia chlamydosporia* mycelium, oat 12 d, EtOH |
| *Pochonia chlamydosporia* mycelium, straw 12 d, EtOH |
| *Pochonia chlamydosporia* mycelium, sawdust 12 d, EtOH |
| *Pochonia chlamydosporia* mycelium, rice 12 d, EtOAc |
| *Pochonia chlamydosporia* mycelium, oat 12 d, EtOAc |
| *Pochonia chlamydosporia* mycelium, straw 12 d, EtOAc |
| *Pochonia chlamydosporia* mycelium, sawdust 12 d, EtOAc |
| *Pochonia chlamydosporia* mycelium, rice 21 d, $H_2O$ |
| *Pochonia chlamydosporia* mycelium, oat 21 d, $H_2O$ |
| *Pochonia chlamydosporia* mycelium, straw 21 d, $H_2O$ |
| *Pochonia chlamydosporia* mycelium, sawdust 21 d, $H_2O$ |
| *Pochonia chlamydosporia* mycelium, rice 21 d, EtOH |
| *Pochonia chlamydosporia* mycelium, oat 21 d, EtOH |
| *Pochonia chlamydosporia* mycelium, straw 21 d, EtOH |
| *Pochonia chlamydosporia* mycelium, sawdust 21 d, EtOH |
| *Pochonia chlamydosporia* mycelium, rice 21 d, EtOAc |
| *Pochonia chlamydosporia* mycelium, oat 21 d, EtOAc |
| *Pochonia chlamydosporia* mycelium, straw 21 d, EtOAc |
| *Pochonia chlamydosporia* mycelium, sawdust 21 d, EtOAc |
| *Pochonia chlamydosporia* mycelium, rice 98 d, $H_2O$ |
| *Pochonia chlamydosporia* mycelium, oat 98 d, $H_2O$ |
| *Pochonia chlamydosporia* mycelium, straw 98 d, $H_2O$ |
| *Pochonia chlamydosporia* mycelium, sawdust 98 d, $H_2O$ |
| *Pochonia chlamydosporia* mycelium, rice 98 d, EtOH |
| *Pochonia chlamydosporia* mycelium, oat 98 d, EtOH |
| *Pochonia chlamydosporia* mycelium, straw 98 d, EtOH |
| *Pochonia chlamydosporia* mycelium, sawdust 98 d, EtOH |
| *Pochonia chlamydosporia* mycelium, rice 98 d, EtOAc |
| *Pochonia chlamydosporia* mycelium, oat 98 d, EtOAc |
| *Pochonia chlamydosporia* mycelium, straw 98 d, EtOAc |
| *Pochonia chlamydosporia* mycelium, sawdust 98 d, EtOAc |
| *Pochonia chlamydosporia* mycelium, rice 198 d, $H_2O$ |
| *Pochonia chlamydosporia* mycelium, oat 198 d, $H_2O$ |
| *Pochonia chlamydosporia* mycelium, straw 198 d, $H_2O$ |
| *Pochonia chlamydosporia* mycelium, sawdust 198 d, $H_2O$ |
| *Pochonia chlamydosporia* mycelium, rice 198 d, EtOH |
| *Pochonia chlamydosporia* mycelium, oat 198 d, EtOH |
| *Pochonia chlamydosporia* mycelium, straw 198 d, EtOH |
| *Pochonia chlamydosporia* mycelium, sawdust 198 d, EtOH |
| *Pochonia chlamydosporia* mycelium, rice 198 d, EtOAc |

TABLE 13-continued

| Test Compositions |
|---|
| *Pochonia chlamydosporia* mycelium, oat 198 d, EtOAc |
| *Pochonia chlamydosporia* mycelium, straw 198 d, EtOAc |
| *Pochonia chlamydosporia* mycelium, sawdust 198 d, EtOAc |
| *Pochonia chlamydosporia* mycelium + psilocybin-containing mycelium, rice 12 d, $H_2O$ |
| *Pochonia chlamydosporia* mycelium + psilocybin-containing mycelium, oat 12 d, $H_2O$ |
| *Pochonia chlamydosporia* mycelium + psilocybin-containing mycelium, straw 12 d, $H_2O$ |
| *Pochonia chlamydosporia* mycelium + psilocybin-containing mycelium, sawdust 12 d, $H_2O$ |
| *Pochonia chlamydosporia* mycelium + psilocybin-containing mycelium, rice 12 d, EtOH |
| *Pochonia chlamydosporia* mycelium + psilocybin-containing mycelium, oat 12 d, EtOH |
| *Pochonia chlamydosporia* mycelium + psilocybin-containing mycelium, straw 12 d, EtOH |
| *Pochonia chlamydosporia* mycelium + psilocybin-containing mycelium, sawdust 12 d, EtOH |
| *Pochonia chlamydosporia* mycelium + psilocybin-containing mycelium, rice 12 d, EtOAc |
| *Pochonia chlamydosporia* mycelium + psilocybin-containing mycelium, oat 12 d, EtOAc |
| *Pochonia chlamydosporia* mycelium + psilocybin-containing mycelium, straw 12 d, EtOAc |
| *Pochonia chlamydosporia* mycelium + psilocybin-containing mycelium, sawdust 12 d, EtOAc |
| *Pochonia chlamydosporia* mycelium + psilocybin-containing mycelium, rice 21 d, $H_2O$ |
| *Pochonia chlamydosporia* mycelium + psilocybin-containing mycelium, oat 21 d, $H_2O$ |
| *Pochonia chlamydosporia* mycelium + psilocybin-containing mycelium, straw 21 d, $H_2O$ |
| *Pochonia chlamydosporia* mycelium + psilocybin-containing mycelium, sawdust 21 d, $H_2O$ |
| *Pochonia chlamydosporia* mycelium + psilocybin-containing mycelium, rice 21 d, EtOH |
| *Pochonia chlamydosporia* mycelium + psilocybin-containing mycelium, oat 21 d, EtOH |
| *Pochonia chlamydosporia* mycelium + psilocybin-containing mycelium, straw 21 d, EtOH |
| *Pochonia chlamydosporia* mycelium + psilocybin-containing mycelium, sawdust 21 d, EtOH |
| *Pochonia chlamydosporia* mycelium + psilocybin-containing mycelium, rice 21 d, EtOAc |
| *Pochonia chlamydosporia* mycelium + psilocybin-containing mycelium, oat 21 d, EtOAc |
| *Pochonia chlamydosporia* mycelium + psilocybin-containing mycelium, straw 21 d, EtOAc |
| *Pochonia chlamydosporia* mycelium + psilocybin-containing mycelium, sawdust 21 d, EtOAc |
| *Pochonia chlamydosporia* mycelium + psilocybin-containing mycelium, rice 98 d, $H_2O$ |
| *Pochonia chlamydosporia* mycelium + psilocybin-containing mycelium, oat 98 d, $H_2O$ |
| *Pochonia chlamydosporia* mycelium + psilocybin-containing mycelium, straw 98 d, $H_2O$ |
| *Pochonia chlamydosporia* mycelium + psilocybin-containing mycelium, sawdust 98 d, $H_2O$ |
| *Pochonia chlamydosporia* mycelium + psilocybin-containing mycelium, rice 98 d, EtOH |
| *Pochonia chlamydosporia* mycelium + psilocybin-containing mycelium, oat 98 d, EtOH |
| *Pochonia chlamydosporia* mycelium + psilocybin-containing mycelium, straw 98 d, EtOH |
| *Pochonia chlamydosporia* mycelium + psilocybin-containing mycelium, sawdust 98 d, EtOH |
| *Pochonia chlamydosporia* mycelium + psilocybin-containing mycelium, rice 98 d, EtOAc |
| *Pochonia chlamydosporia* mycelium + psilocybin-containing mycelium, oat 98 d, EtOAc |
| *Pochonia chlamydosporia* mycelium + psilocybin-containing mycelium, straw 98 d, EtOAc |
| *Pochonia chlamydosporia* mycelium + psilocybin-containing mycelium, sawdust 98 d, EtOAc |
| *Pochonia chlamydosporia* mycelium + psilocybin-containing mycelium, rice 198 d, $H_2O$ |
| *Pochonia chlamydosporia* mycelium + psilocybin-containing mycelium, oat 198 d, $H_2O$ |
| *Pochonia chlamydosporia* mycelium + psilocybin-containing mycelium, straw 198 d, $H_2O$ |
| *Pochonia chlamydosporia* mycelium + psilocybin-containing mycelium, sawdust 198 d, $H_2O$ |
| *Pochonia chlamydosporia* mycelium + psilocybin-containing mycelium, rice 198 d, EtOH |
| *Pochonia chlamydosporia* mycelium + psilocybin-containing mycelium, oat 198 d, EtOH |
| *Pochonia chlamydosporia* mycelium + psilocybin-containing mycelium, straw 198 d, EtOH |
| *Pochonia chlamydosporia* mycelium + psilocybin-containing mycelium, sawdust 198 d, EtOH |
| *Pochonia chlamydosporia* mycelium + psilocybin-containing mycelium, rice 198 d, EtOAc |
| *Pochonia chlamydosporia* mycelium + psilocybin-containing mycelium, oat 198 d, EtOAc |
| *Pochonia chlamydosporia* mycelium + psilocybin-containing mycelium, straw 198 d, EtOAc |
| *Pochonia chlamydosporia* mycelium + psilocybin-containing mycelium, sawdust 198 d, EtOAc |
| Inactivated *Pochonia chlamydosporia* mycelium + psilocybin-containing mycelium, rice 12 d, $H_2O$ |
| Inactivated *Pochonia chlamydosporia* mycelium + psilocybin-containing mycelium, oat 12 d, $H_2O$ |
| Inactivated *Pochonia chlamydosporia* mycelium + psilocybin-containing mycelium, straw 12 d, $H_2O$ |
| Inactivated *Pochonia chlamydosporia* mycelium + psilocybin-containing mycelium, sawdust 12 d, $H_2O$ |
| Inactivated *Pochonia chlamydosporia* mycelium + psilocybin-containing mycelium, rice 12 d, EtOH |
| Inactivated *Pochonia chlamydosporia* mycelium + psilocybin-containing mycelium, oat 12 d, EtOH |
| Inactivated *Pochonia chlamydosporia* mycelium + psilocybin-containing mycelium, straw 12 d, EtOH |
| Inactivated *Pochonia chlamydosporia* mycelium + psilocybin-containing mycelium, sawdust 12 d, EtOH |
| Inactivated *Pochonia chlamydosporia* mycelium + psilocybin-containing mycelium, rice 12 d, EtOAc |
| Inactivated *Pochonia chlamydosporia* mycelium + psilocybin-containing mycelium, oat 12 d, EtOAc |
| Inactivated *Pochonia chlamydosporia* mycelium + psilocybin-containing mycelium, straw 12 d, EtOAc |
| Inactivated *Pochonia chlamydosporia* mycelium + psilocybin-containing mycelium, sawdust 12 d, EtOAc |
| Inactivated *Pochonia chlamydosporia* mycelium + psilocybin-containing mycelium, rice 21 d, $H_2O$ |
| Inactivated *Pochonia chlamydosporia* mycelium + psilocybin-containing mycelium, oat 21 d, $H_2O$ |
| Inactivated *Pochonia chlamydosporia* mycelium + psilocybin-containing mycelium, straw 21 d, $H_2O$ |
| Inactivated *Pochonia chlamydosporia* mycelium + psilocybin-containing mycelium, sawdust 21 d, $H_2O$ |
| Inactivated *Pochonia chlamydosporia* mycelium + psilocybin-containing mycelium, rice 21 d, EtOH |
| Inactivated *Pochonia chlamydosporia* mycelium + psilocybin-containing mycelium, oat 21 d, EtOH |
| Inactivated *Pochonia chlamydosporia* mycelium + psilocybin-containing mycelium, straw 21 d, EtOH |
| Inactivated *Pochonia chlamydosporia* mycelium + psilocybin-containing mycelium, sawdust 21 d, EtOH |
| Inactivated *Pochonia chlamydosporia* mycelium + psilocybin-containing mycelium, rice 21 d, EtOAc |
| Inactivated *Pochonia chlamydosporia* mycelium + psilocybin-containing mycelium, oat 21 d, EtOAc |
| Inactivated *Pochonia chlamydosporia* mycelium + psilocybin-containing mycelium, straw 21 d, EtOAc |
| Inactivated *Pochonia chlamydosporia* mycelium + psilocybin-containing mycelium, sawdust 21 d, EtOAc |
| Inactivated *Pochonia chlamydosporia* mycelium + psilocybin-containing mycelium, rice 98 d, $H_2O$ |
| Inactivated *Pochonia chlamydosporia* mycelium + psilocybin-containing mycelium, oat 98 d, $H_2O$ |
| Inactivated *Pochonia chlamydosporia* mycelium + psilocybin-containing mycelium, straw 98 d, $H_2O$ |

TABLE 13-continued

| Test Compositions |
|---|
| Inactivated *Pochonia chlamydosporia* mycelium + psilocybin-containing mycelium, sawdust 98 d, $H_2O$ |
| Inactivated *Pochonia chlamydosporia* mycelium + psilocybin-containing mycelium, rice 98 d, EtOH |
| Inactivated *Pochonia chlamydosporia* mycelium + psilocybin-containing mycelium, oat 98 d, EtOH |
| Inactivated *Pochonia chlamydosporia* mycelium + psilocybin-containing mycelium, straw 98 d, EtOH |
| Inactivated *Pochonia chlamydosporia* mycelium + psilocybin-containing mycelium, sawdust 98 d, EtOH |
| Inactivated *Pochonia chlamydosporia* mycelium + psilocybin-containing mycelium, rice 98 d, EtOAc |
| Inactivated *Pochonia chlamydosporia* mycelium + psilocybin-containing mycelium, oat 98 d, EtOAc |
| Inactivated *Pochonia chlamydosporia* mycelium + psilocybin-containing mycelium, straw 98 d, EtOAc |
| Inactivated *Pochonia chlamydosporia* mycelium + psilocybin-containing mycelium, sawdust 98 d, EtOAc |
| Inactivated *Pochonia chlamydosporia* mycelium + psilocybin-containing mycelium, rice 198 d, $H_2O$ |
| Inactivated *Pochonia chlamydosporia* mycelium + psilocybin-containing mycelium, oat 198 d, $H_2O$ |
| Inactivated *Pochonia chlamydosporia* mycelium + psilocybin-containing mycelium, straw 198 d, $H_2O$ |
| Inactivated *Pochonia chlamydosporia* mycelium + psilocybin-containing mycelium, sawdust 198 d, $H_2O$ |
| Inactivated *Pochonia chlamydosporia* mycelium + psilocybin-containing mycelium, rice 198 d, EtOH |
| Inactivated *Pochonia chlamydosporia* mycelium + psilocybin-containing mycelium, oat 198 d, EtOH |
| Inactivated *Pochonia chlamydosporia* mycelium + psilocybin-containing mycelium, straw 198 d, EtOH |
| Inactivated *Pochonia chlamydosporia* mycelium + psilocybin-containing mycelium, sawdust 198 d, EtOH |
| Inactivated *Pochonia chlamydosporia* mycelium + psilocybin-containing mycelium, rice 198 d, EtOAc |
| Inactivated *Pochonia chlamydosporia* mycelium + psilocybin-containing mycelium, oat 198 d, EtOAc |
| Inactivated *Pochonia chlamydosporia* mycelium + psilocybin-containing mycelium, straw 198 d, EtOAc |
| Inactivated *Pochonia chlamydosporia* mycelium + psilocybin-containing mycelium, sawdust 198 d, EtOAc |
| *Pochonia chlamydosporia* fruiting body, $H_2O$ |
| *Pochonia chlamydosporia* fruiting body, EtOH |
| *Pochonia chlamydosporia* fruiting body, EtOAc |
| *Pochonia chlamydosporia* + baeocystin 0.3 µg/mL |
| *Pochonia chlamydosporia* + baeocystin 1 µg/mL |
| *Pochonia chlamydosporia* + norbaeocystin 0.3 µg/mL |
| *Pochonia chlamydosporia* + norbaeocystin 1 µg/mL |
| *Pochonia chlamydosporia* + norpsilocin 0.3 µg/mL |
| *Pochonia chlamydosporia* + norpsilocin 1 µg/mL |
| *Pochonia chlamydosporia* fruiting body + psilocybin-containing fruiting body, $H_2O$ |
| *Pochonia chlamydosporia* fruiting body + psilocybin-containing fruiting body, EtOH |
| *Pochonia chlamydosporia* fruiting body + psilocybin-containing fruiting body, EtOAc |
| *Pochonia chlamydosporia* + psilocybin-containing mycelium + baeocystin 0.3 µg/mL |
| *Pochonia chlamydosporia* + psilocybin-containing mycelium + baeocystin 1 µg/mL |
| *Pochonia chlamydosporia* + psilocybin-containing mycelium + norbaeocystin 0.3 µg/mL |
| *Pochonia chlamydosporia* + psilocybin-containing mycelium + norbaeocystin 1 µg/mL |
| Pochonia chlamydosporia + psilocybin-containing mycelium + norpsilocin 0.3 µg/mL |
| *Pochonia chlamydosporia* + psilocybin-containing mycelium + norpsilocin 1 µg/mL |
| Inactivated *Pochonia chlamydosporia* + psilocybin-containing mycelium + baeocystin 0.3 µg/mL |
| Inactivated *Pochonia chlamydosporia* + psilocybin-containing mycelium + baeocystin 1 µg/mL |
| Inactivated *Pochonia chlamydosporia* + psilocybin-containing mycelium + norbaeocystin 0.3 µg/mL |
| Inactivated *Pochonia chlamydosporia* + psilocybin-containing mycelium + norbaeocystin 1 µg/mL |
| Inactivated *Pochonia chlamydosporia* + psilocybin-containing mycelium + norpsilocin 0.3 µg/mL |
| Inactivated *Pochonia chlamydosporia* + psilocybin-containing mycelium + norpsilocin 1 µg/mL |

The compositions are tested for effects on neurite outgrowth and lengthening, MAPK signaling, NGF expression, depression, anxiety, and mood. The composition may be used in a microdosing regimen.

Example 7

This research has revealed distinct roles of psilocybin analogs in benefiting neurological health. ELISA assays in human 1321N1 brain cells found that norbaeocystin induces the expression of nerve growth factor (NGF) protein while norpsilocin induces the expression of the anti-inflammatory cytokine IL-10. Moreover, Ly et al. found that psychedelic compounds are unable to induce the expression of BDNF transcript, while we have observed strong induction of BDNF transcript by lion's mane extract. See Ly et al., "Psychedelics Promote Structural and Functional Neural Plasticity," *Cell Rep.* 23: 3170-3182 (2018). Collectively, this suggests that the combination of psilocybin analogs with lion's mane benefits brain health in diverse and complementary mechanisms.

Neuroinflammatory consequences of COVID-19 infection, and that of other neuroinflammatory viruses, causes a wide range of negative effects on human health and mental well-being. Since health and mental health are inextricably interrelated, there is a great need to resolve adverse effects to the nervous system in general. In addition, activation of 5-$HT_{2A}$receptors produces potent anti-inflammatory effects in animal models and are believed to block TNF-a induced inflammation. See Flanagan and Nichols, "Psychedelics and anti-inflammatory agents" *Inter. Rev. Psychiatry* 30(4): 363-375 (2018). Thus, the compositions described herein may have synergistic benefits in reducing inflammation, increasing neurogenesis, and ameliorating mental health disorders or issues.

Further, high doses of tryptamines, particularly aeruginascin, 4-hydroxy-N,N,N-trimethyltryptamine, or bufotenidine, may be useful for anesthesic or neuroanesthetic applications. These compounds are associated with the phenomenon "Wood Lover Paralysis," a temporary muscle weakness or paralysis that sometimes occurs several hours after consuming certain types of psilocybin mushrooms grown on decaying wood.

The unique combination, or norpsilocin alone, will have a significant impact on the improvement of mental health and resolution or amelioration of a wide range of mental diseases. Such improvements include increase in intelligence, cognition, mental state of being, mood, overcoming depression, overcoming PTSD, enhancing coordination, hearing, seeing or vision. Moreover, the combinations in this invention may positively impact and improve the neurological health of those suffering from Alzheimer's, multiple sclerosis, and other diseases that are detrimental to human health as a consequence of neuroinflammation.

The methods and compositions that includes the combination of norbaeocystin to induce the expression of nerve growth factor (NGF) protein and norpsilocin to induce the expression of the anti-inflammatory cytokine IL-10.

The psilocybin analogs described herein have unique binding characteristics with 5-HT receptors and can work synergistically to have greater than the expected cumulative effects.

What is claimed:

1. A method for treating, alleviating, or ameliorating one or more symptoms associated with a mood disorder, the method comprising administering a pharmaceutical dosage form comprising:

0.1 mg to 10 mg of psilocin, psilocybin, salts thereof, or combinations thereof; and one or more pharmaceutically acceptable excipients selected from carriers, fillers, binders, disintegrants, preservatives, or antioxidants.

2. The method of claim 1, wherein the pharmaceutical dosage form comprises 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5, mg, 6 mg, 7 mg, 8 mg, 9 mg, or 10 mg of psilocybin or psilocin.

3. The method of claim 1, wherein the wherein the psilocin, psilocybin, salts thereof, or combinations thereof are:

(a) pure compounds;

(b) from mushroom species comprising psilocybin, psilocin, salts thereof, or combinations thereof; or (c) from extracts of mushroom species comprising psilocybin, psilocin, salts thereof;

combinations thereof.

4. The method of claim 1, wherein the pharmaceutical dosage form further comprises 10 μg to 200 mg of niacin.

5. The method of claim 1 further comprising acidifying agents, alkalizing agents, antifoaming agents, sweetening agents, buffering agents, chelating agents, coating agents, emulsifying agents, solubilizing agents, flavoring agents, coloring agents, humectants, or a combination thereof.

6. The method of claim 1, wherein the administration is at a regular interval until the subject in need thereof does not require administration.

7. The method of claim 1, wherein the pharmaceutical dosage form is administered 1 to 6 times per day.

8. The method of claim 1, wherein the mood disorder comprises depression, major depressive disorder, treatment resistant depression, persistent depression, manic depression or bipolar disorder, depressive psychosis, perinatal depression, premenstrual dysphoric disorder, seasonal depression, situational depression, panic disorder, or a combination thereof.

9. The method of claim 1, wherein the psilocybin or psilocin bind to a neurotropin receptor.

10. The method of claim 1, wherein the pharmaceutical dosage form releases one or more neurotropins.

11. The method of claim 1, wherein the pharmaceutical dosage form enhances neuronal plasticity.

12. A method for treating, alleviating, or ameliorating one or more symptoms associated with a psychiatric disorder, the method comprising: administering to the subject a pharmaceutical dosage form comprising:

0.1 mg to 10 mg of psilocin, psilocybin, salts thereof, or combinations thereof; and one or more pharmaceutically acceptable excipients selected from carriers, fillers, binders, disintegrants, preservatives, or antioxidants.

13. The method of claim 12, wherein the wherein the psilocin, psilocybin, salts thereof, or combinations thereof are:

(a) pure compounds;

(b) from mushroom species comprising psilocybin, psilocin, salts thereof, or combinations thereof; or (c) from extracts of mushroom species comprising psilocybin, psilocin, salts thereof;

combinations thereof.

14. The method of claim 12, wherein the pharmaceutical dosage form further comprises 10 μg to 200 mg of niacin.

15. The method of claim 12, further comprising acidifying agents, alkalizing agents, antifoaming agents, sweetening agents, buffering agents, chelating agents, coating agents, emulsifying agents, solubilizing agents, flavoring agents, coloring agents, humectants, or a combination thereof.

16. The method of claim 12, wherein the administration is at a regular interval until the subject in need thereof does not require administration.

17. The method of claim 12, wherein the pharmaceutical dosage form is administered 1 to 6 times per day.

18. The method of claim 12, wherein the psychiatric disorder comprises anxiety, substance abuse disorders, attention deficit/hyperactivity disorder, sleep disorders, eating disorders, schizophrenia, personality disorders, or a combination thereof.

19. The method of claim 12, wherein the psilocybin or psilocin bind to a neurotropin receptor.

20. The method of claim 12, wherein the pharmaceutical dosage form releases one or more neurotropins.

* * * * *